United States Patent
Miracco

(10) Patent No.: US 11,384,352 B2
(45) Date of Patent: Jul. 12, 2022

(54) RNA AFFINITY PURIFICATION

(71) Applicant: ModernaTX, Inc., Cambridge, MA (US)

(72) Inventor: Edward J. Miracco, Arlington, MA (US)

(73) Assignee: ModernaTX, Inc., Cambridge, MA (US)

( * ) Notice: Subject to any disclaimer, the term of this patent is extended or adjusted under 35 U.S.C. 154(b) by 296 days.

(21) Appl. No.: 16/468,838

(22) PCT Filed: Dec. 13, 2017

(86) PCT No.: PCT/US2017/065962
§ 371 (c)(1),
(2) Date: Jun. 12, 2019

(87) PCT Pub. No.: WO2018/111967
PCT Pub. Date: Jun. 21, 2018

(65) Prior Publication Data
US 2020/0071689 A1    Mar. 5, 2020

Related U.S. Application Data

(60) Provisional application No. 62/433,352, filed on Dec. 13, 2016.

(51) Int. Cl.
*C12N 15/10* (2006.01)
*C12N 9/22* (2006.01)
*C12N 11/14* (2006.01)

(52) U.S. Cl.
CPC ........... *C12N 15/1006* (2013.01); *C12N 9/22* (2013.01); *C12N 11/14* (2013.01); *C12Y 301/26003* (2013.01)

(58) Field of Classification Search
None
See application file for complete search history.

(56) References Cited

U.S. PATENT DOCUMENTS

| | | |
|---|---|---|
| 5,256,555 A | 10/1993 | Milburn et al. |
| 6,814,964 B2 | 11/2004 | Virtanen et al. |
| 8,710,200 B2 | 4/2014 | Schrum et al. |
| 8,754,062 B2 | 6/2014 | De Fougerolles et al. |
| 8,822,663 B2 | 9/2014 | Schrum et al. |
| 8,999,380 B2 | 4/2015 | Bancel et al. |
| 9,163,246 B2 | 10/2015 | Barnes |
| 9,221,891 B2 | 12/2015 | Bancel et al. |
| 9,283,287 B2 | 3/2016 | Bancel et al. |
| 9,303,079 B2 | 4/2016 | Bancel et al. |
| 9,464,124 B2 | 10/2016 | Bancel et al. |
| 9,512,456 B2 | 12/2016 | Wang et al. |
| 9,533,047 B2 | 1/2017 | de Fougerolles et al. |
| 9,597,380 B2 | 3/2017 | Chakraborty et al. |
| 9,868,691 B2 | 1/2018 | Benenato et al. |
| 9,872,900 B2 | 1/2018 | Ciaramella et al. |
| 10,064,934 B2 | 9/2018 | Ciaramella et al. |
| 10,064,935 B2 | 9/2018 | Ciaramella et al. |
| 10,124,055 B2 | 11/2018 | Ciaramella et al. |
| 10,207,010 B2 | 2/2019 | Besin et al. |
| 10,232,055 B2 | 3/2019 | Kariko et al. |
| 10,273,269 B2 | 4/2019 | Ciaramella |
| 10,286,086 B2 | 5/2019 | Roy et al. |
| 10,385,088 B2 | 8/2019 | Fraley et al. |
| 10,449,244 B2 | 10/2019 | Ciaramella et al. |
| 10,465,190 B1 | 11/2019 | Chen et al. |
| 10,493,143 B2 | 12/2019 | Ciaramella et al. |
| 10,526,629 B2 | 1/2020 | Rabideau et al. |
| 10,653,712 B2 | 5/2020 | Hoge |
| 10,653,767 B2 | 5/2020 | Ciaramella et al. |
| 10,695,419 B2 | 6/2020 | Ciaramella et al. |
| 10,857,105 B2 | 12/2020 | Benenato et al. |
| 10,925,958 B2 | 2/2021 | Ciaramella |
| 11,045,540 B2 | 6/2021 | Ciaramella |
| 2003/0165849 A1 | 9/2003 | Zhang et al. |
| 2005/0042621 A1 | 2/2005 | Cole et al. |
| 2005/0287540 A1 | 12/2005 | Murphy et al. |
| 2008/0220471 A1 | 9/2008 | Davis et al. |
| 2011/0143397 A1* | 6/2011 | Kariko ............... C07K 14/4712 435/70.3 |
| 2013/0102034 A1 | 4/2013 | Schrum et al. |
| 2013/0111615 A1 | 5/2013 | Kariko et al. |

(Continued)

FOREIGN PATENT DOCUMENTS

| | | |
|---|---|---|
| EP | 2092064 | 9/2010 |
| WO | WO 2008/077592 A1 | 7/2008 |

(Continued)

OTHER PUBLICATIONS

Blaszczyk, J. et al. 2004. Noncatalytic assembly of ribonuclease III with double-stranded RNA. Structure 12: 457-466; specif, pp. 457, 458, 463, 464.*

Li, H. et al. 1996. Defining the enzyme binding domain of a ribonuclease III processing signal. Ethylation interference and hydroxyl radical footprinting using catalytically inactive RNase III mutants. The EMBO Journal 15(6): 1421-1433; specif, p. 1421.*

Singh, R. et al. May/Jun. 2015. Complete genome sequence of an evolved Thermogoga maritima isolate. Genome Announcements. Journals.ASM.org 3(3): 1-2. With Gen Bank accession #CP010967 as supplemental p. 3; specif, pp. 1,3.*

(Continued)

*Primary Examiner* — Olivia M. Wise
*Assistant Examiner* — Sharon M. Papciak
(74) *Attorney, Agent, or Firm* — Wolf, Greenfield & Sacks, P.C.

(57) ABSTRACT

Provided herein, in some embodiments, are methods of purifying a nucleic acid preparation. The methods may comprise contacting a nucleic acid preparation comprising messenger ribonucleic acid with an RNase III enzyme that is immobilized on a solid support and binds to double-stranded RNA contaminants.

18 Claims, 8 Drawing Sheets
Specification includes a Sequence Listing.

(56) References Cited

U.S. PATENT DOCUMENTS

| | | |
|---|---|---|
| 2013/0197068 A1 | 8/2013 | Kariko et al. |
| 2013/0236974 A1 | 9/2013 | De Fougerolles |
| 2013/0245103 A1 | 9/2013 | De Fougerolles et al. |
| 2013/0259923 A1 | 10/2013 | Bancel et al. |
| 2014/0142290 A1 | 5/2014 | Madden et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0378538 A1 | 12/2014 | Bancel |
| 2015/0051268 A1 | 2/2015 | Bancel et al. |
| 2015/0056253 A1 | 2/2015 | Bancel et al. |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2015/0368625 A1 | 12/2015 | Segall-Shapiro et al. |
| 2015/0376581 A1 | 12/2015 | Brakmann et al. |
| 2016/0024140 A1 | 1/2016 | Issa et al. |
| 2016/0024141 A1 | 1/2016 | Issa et al. |
| 2016/0032261 A1 | 2/2016 | Sobek et al. |
| 2016/0032273 A1 | 2/2016 | Shahrokh et al. |
| 2016/0038612 A1 | 2/2016 | Hoge et al. |
| 2016/0243221 A1 | 8/2016 | Hoge et al. |
| 2017/0043037 A1 | 2/2017 | Kariko et al. |
| 2017/0202979 A1 | 7/2017 | Chakraborty et al. |
| 2017/0204152 A1 | 7/2017 | Nelson et al. |
| 2017/0130255 A1 | 10/2017 | Wang et al. |
| 2018/0000953 A1 | 1/2018 | Almarsson et al. |
| 2018/0002393 A1 | 1/2018 | Bancel et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0318409 A1 | 11/2018 | Valiante et al. |
| 2018/0369374 A1 | 12/2018 | Frederick et al. |
| 2018/0371047 A1 | 12/2018 | Ticho et al. |
| 2019/0002890 A1 | 1/2019 | Martini et al. |
| 2019/0008938 A1 | 1/2019 | Ciaramella et al. |
| 2019/0085368 A1 | 3/2019 | Bancel et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0275170 A1 | 9/2019 | Benenato et al. |
| 2019/0298657 A1 | 10/2019 | Martini et al. |
| 2019/0298658 A1 | 10/2019 | Benenato |
| 2019/0300906 A1 | 10/2019 | Martini et al. |
| 2019/0314292 A1 | 10/2019 | Benenato et al. |
| 2019/0336452 A1 | 11/2019 | Brader |
| 2019/0351040 A1 | 11/2019 | Valiante et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0069794 A1 | 3/2020 | Ciaramella et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129608 A1 | 4/2020 | Ciaramella et al. |
| 2020/0129615 A1 | 4/2020 | Ciaramella et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2021/0046173 A1 | 2/2021 | Ciaramella et al. |
| 2021/0163919 A1 | 6/2021 | Issa et al. |
| 2021/0187097 A1 | 6/2021 | Ciaramella et al. |

FOREIGN PATENT DOCUMENTS

| | | | |
|---|---|---|---|
| WO | WO 2011/156539 A2 | 12/2011 | |
| WO | WO 2013/003475 A1 | 1/2013 | |
| WO | WO 2013/050609 A1 | 4/2013 | |
| WO | WO 2013/102203 A1 | 7/2013 | |
| WO | WO 2014/140211 A1 | 9/2014 | |
| WO | WO 2014/152966 A1 | 9/2014 | |
| WO | WO-2014160243 A1 * | 10/2014 | ........... C07K 14/505 |
| WO | WO 2016/164762 A1 | 10/2016 | |
| WO | WO 2016/172346 A1 | 10/2016 | |
| WO | WO 2016/201377 A1 | 12/2016 | |
| WO | WO 2017/015457 A1 | 1/2017 | |
| WO | WO 2017/153936 | 3/2017 | |
| WO | WO 2017/066789 A1 | 4/2017 | |
| WO | WO 2017/070601 A1 | 4/2017 | |
| WO | WO 2017/127750 A1 | 7/2017 | |
| WO | WO 2017/201333 A1 | 11/2017 | |
| WO | WO 2018/096179 A1 | 5/2018 | |
| WO | WO 2018/157009 A1 | 8/2018 | |
| WO | WO 2018/232355 A1 | 12/2018 | |
| WO | WO 2018/232357 A1 | 12/2018 | |
| WO | WO 2019/005540 A1 | 1/2019 | |
| WO | WO 2019/036683 A1 | 2/2019 | |
| WO | WO 2020/006242 A1 | 1/2020 | |
| WO | WO 2020/056370 A1 | 3/2020 | |
| WO | WO 2020/061284 A1 | 3/2020 | |
| WO | WO 2020/061295 A1 | 3/2020 | |
| WO | WO 2020/061367 A1 | 3/2020 | |
| WO | WO 2020/097291 A1 | 5/2020 | |
| WO | WO 2020/172239 A1 | 8/2020 | |
| WO | WO 2020/185811 A1 | 9/2020 | |
| WO | WO 2020/190750 A1 | 9/2020 | |
| WO | WO 2020/243561 A1 | 12/2020 | |
| WO | WO 2021/030533 A1 | 2/2021 | |
| WO | WO 2021/050864 A1 | 3/2021 | |
| WO | WO 2021/055811 A1 | 3/2021 | |

OTHER PUBLICATIONS

Butterer, A. et al. 2012. Using immobilized enzymes to reduce RNase contamination in RNase mapping of transfer RNAs by mass spectrometry. Analytical and Bioanalytical Chemistry 402: 2701-2711; specif, p. 2701.*

Mohamad, N.R. et al. Feb. 2015. An overview kof technologies for immobilization of enzymes and surface analysis techniques for immobilized enzymes. Biotechnology & Biotechnological Equipment 29(2): 205-220; specif, pp. 205, 206, 207, 209.*

U.S. Appl. No. 16/036,318, filed Jul. 16, 2018, Ciaramella et al.
U.S. Appl. No. 16/144,394, filed Sep. 27, 2018, Ciaramella et al.
U.S. Appl. No. 17/204,801, filed Mar. 17, 2021, Ciaramella et al.
U.S. Appl. No. 15/748,773, filed Jan. 30, 2018, Ciaramella et al.
U.S. Appl. No. 15/753,293, filed Feb. 17, 2018, Smith.
U.S. Appl. No. 15/767,587, filed Apr. 11, 2018, Ciaramella.
U.S. Appl. No. 16/833,409, filed Mar. 27, 2020, Ciaramella.
U.S. Appl. No. 15/767,600, filed Apr. 11, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 16/853,973, filed Apr. 21, 2020, Ciaramella et al.
U.S. Appl. No. 16/850,519, filed Apr. 16, 2020, Ciaramella et al.
U.S. Appl. No. 16/897,859, filed Jun. 10, 2020, Ciaramella et al.
U.S. Appl. No. 16/898,268, filed Jun. 10, 2020, Ciaramella et al.
U.S. Appl. No. 16/599,661, filed Oct. 11, 2019, Besin et al.
U.S. Appl. No. 16/333,330, filed Mar. 14, 2019, Hoge et al.
U.S. Appl. No. 16/864,566, filed May 1, 2020, Ciaramella et al.
U.S. Appl. No. 16/897,734, filed Jun. 10, 2020, Ciaramella et al.
U.S. Appl. No. 16/001,765, filed Jun. 6, 2018, Marquardt et al.
U.S. Appl. No. 17/127,949, filed Dec. 18, 2020, Ciaramella.
U.S. Appl. No. 16/467,142, filed Jun. 6, 2019, Ciaramella et al.

(56) References Cited

OTHER PUBLICATIONS

U.S. Appl. No. 16/603,111, filed Oct. 4, 2019, Brito et al.
U.S. Appl. No. 16/482,844, filed Aug. 1, 2019, Valiante et al.
U.S. Appl. No. 16/496,135, filed Sep. 20, 2019, Narayanan et al.
U.S. Appl. No. 16/483,012, filed Aug. 1, 2019, Mauger et al.
U.S. Appl. No. 16/657,122, filed Oct. 18, 2019, Rabideau et al.
U.S. Appl. No. 17/350,662, filed Jun. 17, 2021, Rabideau et al.
U.S. Appl. No. 16/362,366, filed Mar. 22, 2019, Ciaramella.
U.S. Appl. No. 16/493,986, filed Sep. 13, 2019, Ciaramella et al.
U.S. Appl. No. 16/494,130, filed Sep. 13, 2019, Ciaramella et al.
U.S. Appl. No. 16/494,103, filed Sep. 13, 2019, Ciaramella et al.
U.S. Appl. No. 17/245,973, filed Apr. 30, 2021, Ciaramella.
U.S. Appl. No. 16/494,988, filed Sep. 17, 2019, Ciaramella et al.
U.S. Appl. No. 17/155,592, filed Jan. 22, 2021, Ciaramella et al.
U.S. Appl. No. 16/639,269, filed Feb. 14, 2020, Issa et al.
U.S. Appl. No. 16/639,305, filed Feb. 14, 2020, Issa et al.
U.S. Appl. No. 16/765,285, filed May 19, 2020, Ciaramella et al.
U.S. Appl. No. 16/302,607, filed Nov. 16, 2018, Benenato et al.
U.S. Appl. No. 16/623,069, filed Dec. 16, 2019, Hoge et al.
U.S. Appl. No. 16/639,403, filed Feb. 14, 2020, Hoge et al.
U.S. Appl. No. 16/848,318, filed Apr. 14, 2020, Ciaramella et al.
U.S. Appl. No. 16/965,589, filed Jul. 28, 2020, Ciaramella et al.
U.S. Appl. No. 17/255,949, filed Dec. 23, 2020, Zhong et al.
U.S. Appl. No. 17/277,423, filed Mar. 18, 2021, Almarsson et al.
U.S. Appl. No. 17/277,452, filed Mar. 18, 2021, Hennessy et al.
U.S. Appl. No. 17/276,112, filed Mar. 12, 2021, Martini et al.
U.S. Appl. No. 17/291,947, filed May 6, 2021, Ashburn et al.
U.S. Appl. No. 17/325,883, filed May 20, 2021, Dousis et al.
U.S. Appl. No. 16/788,182, filed Feb. 11, 2020, Panther et al.
U.S. Appl. No. 16/794,318, filed Feb. 19, 2020, Mauger et al.
U.S. Appl. No. 17/145,164, filed Jan. 8, 2021, Giessel et al.
U.S. Appl. No. 17/000,201, filed Aug. 21, 2020, Stewart-Jones et al.
U.S. Appl. No. 17/000,215, filed Aug. 21, 2020, Stewart-Jones et al.
PCT/US2017/065962, Mar. 7, 2018, International Search Report and Written Opinion.
International Search Report and Written Opinion for International Application No. PCT/US2017/065962, dated Mar. 7, 2018.
[No Author Listed], GenBank Accession No. AGL50032.1, Ribonuclease III [Thermotoga maritima MSB8], Dec. 11, 2013.
Andrews-Pfannkoch, C. et al., Hydroxyapatite-mediated separation of double-stranded DNA, single-stranded DNA, and RNA genomes from natural viral assemblages. Appl Environ Microbiol. Aug. 2010;76(15):5039-45. Epub Jun. 11, 2010.
Azarani et al., RNA analysis by ion-pair reversed-phase high performance liquid chromatography. Nucleic Acids Res. Jan. 15, 2001;29(2):E7. doi: 10.1093/nar/29.2.e7.
Blaszczyk et al., Noncatalytic assembly of ribonuclease III with double-stranded RNA. Structure. Mar. 2004;12(3):457-66. doi: 10.1016/j.str.2004.02.004.
Bonham et al., An assessment of the antisense properties of RNase H-competent and steric-blocking oligomers. Nucleic Acids Res. Apr. 11, 1995; 23(7): 1197-1203.
Dickman., Ion Pair Reverse-Phase Chromatography: A Versatile Platform for the Analysis of RNA. Chromatography Today. 2011; 22-26.
Easton et al., Rapid, nondenaturing RNA purification using weak anion-exchange fast performance liquid chromatography. RNA. Mar. 2010;16(3):647-53. Epub Jan. 25, 2010.
Edelmann et al., Production of pure and functional RNA for in vitro reconstitution experiments. Methods. Feb. 2014;65(3):333-41. doi: 10.1016/j.ymeth.2013.08.034. Epub Sep. 8, 2013.
Foster et al., Abstract 5614: Novel mRNA purification method with RnaseIII improves efficacy of RNA chimeric antigen receptor T cells. Proceedings of the American Association for Cancer Research Annual Meeting 2017; Apr. 15, 2017; Washington, DC. Philadelphia (PA): AACR; Cancer Res 2017;77(13 Suppl): Abstract nr 5614.
Georgopoulos et al., Use of high-performance liquid chromatographic fractionation of large RNA molecules in the assay of group I intron ribozyme activity. J Chromatogr A. Jan. 28, 2000;868(1):109-14.
Hartmann et al., Handbook of RNA Biochemistry, Second Edition, "Part I RNA Synthesis and Detection." 2014. p. 1-27.
Huber et al., Analysis of nucleic acids by on-line liquid chromatography—Mass spectrometry (Mass Spectrometry Reviews 2001, 20, pp. 310-343).
Kingston, 'Preparation of poly (A)+ RNA', Current protocols in molecular biology. 1993, vol. 21, No. 1, pp. 4.51-4.5.3.
Knudsen et al., Antisense properties of duplex- and triplex-forming PNAs. Nucleic Acids Res. Feb. 1, 1996; 24(3): 494 500.
Lapham, J. et al., RNase H cleavage for processing of in vitro transcribed RNA for NMR studies and RNA ligation, RNA. Mar. 1996;2(3):289-96.
Lee et al., Separation and determination of polyethylene glycol fatty acid esters in cosmetics by a reversed-phase HPLC/ELSD. Taianta. Feb. 15, 2008;74(5):1615-20. doi: 10.1016/j.talanta.2007.10.020. Epub Oct. 18, 2007.
Mellits, K.H. et al., Removal of double-stranded contaminants from RNA transcripts: synthesis of adenovirus VA RNAI from a T7 vector. Nucleic Acids Res. Sep. 25, 1990;18(18):5401-6.
Nwokeoji et al., Purification and characterisation of dsRNA using ion pair reverse phase chromatography and mass spectrometry. J Chromatogr A. Feb. 10, 2017;1484:14-25. doi: 10.1016/j.chroma.2016.12.062. Epub Dec. 21, 2016.
Slater, The purification of poly(a)-containing RNA by affinity chromatography. Methods Mol Biol. 1985;2:117-20. doi: 10.1385/0-89603-064-4:117.
Wang et al., Purification of the messenger ribonucleic acid for the lipoprotein of the *Escherichia coli* outer membrane. Biochemistry. Oct. 2, 1979;18(20):4270-7.
Weissman et al., HPLC purification of in vitro transcribed long RNA. Methods Mol Biol. 2013;969:43-54. doi: 10.1007/978-1-62703-260-5_3.
Wysoczynski et al., Reversed-phase ion-pair liquid chromatography method for purification of duplex DNA with single base pair resolution. Nucleic Acids Res. Nov. 2013;41(20):e194. doi: 10.1093/nar/gkt815. Epub Sep. 5, 2013.
Zhang et al., Ion-pair reversed-phase chromatography of short double-stranded deoxyribonucleic acid in silicon micro-pillar array columns: retention model and applications. J Chromatogr A. Jun. 14, 2013;1294:1-9. doi: 10.1016/j.chroma.2013.04.002. Epub Apr. 8, 2013.

* cited by examiner

|  |  | α1 |  | α2 | α2' |  |  |
|---|---|---|---|---|---|---|---|

```
               α1           α2    α2'
Aa-RNase III     ....MKMLE QLEKKLGYTF KDKSLLEKAL THVSYS.... ...KK..EHY   36
Tm-RNase III     MNESERKIVE EFQKETGINF KNEELLFRAL CHSSYANEQN QAGRKDVESN  50
Ec-RNase III     MN...PIVIN RLQRKLGYTF NHQELLQQAL THRSAS.... ...SK...HN  37

α3              α4           α5
Aa-RNase III     ETLEFLGDAL VNFFIVDLLV QYSPNKREGF LSPLKAYLIS EEFFNLLAQK   86
Tm-RNase III     EKLEFLGDAV LELFVCEILY KKYPEAEVGD LARVKSAAAS EEVLAMVSRK  100
Ec-RNase III     ERLEFLGDSI LSYVIANALY HRFPRVDEGD MSRMRATLVR GNTLAELARE   87
                       1 2

3_10    α5'   3_10      α6                α7
Aa-RNase III    LELHKFIRIK RG..KIN... .ETIIGDFFE AWAAVYIDS GRDANFTREL  130
Tm-RNase III    MNLGKFLFLG KGEENTGGRD RDSILADFE ALAAIYLDQ GYEK..IKEL  148
Ec-RNase III    FELGECLRLG PGELKSGGFR RESILADVFE ALIGGVFLDS DIQT..VEKL  135
                             3                4

α7              α8             β1    3_10
Aa-RNase III    FYKLFKEDIL SAIKEGRVKK DYKTILQEIT QKRWKERPEY RLISVEGPHH  180
Tm-RNase III    FEQEF.EFYI EKIMKGEMLF DYKTALQEIV QSEHKVPPEY ILVRTEKNDG  197
Ec-RNase III    ILNWY.QTRL DEISPGDKQK QPKTRLQEYL QGRHLPLPTY LVVQVRGEAH  184
                                       5 6

β2      β3         α9
Aa-RNase III    KKKFIVEAKI K..EYRTLGE CKSKKEAEQR AA.EELIKLL HESL        221
Tm-RNase III    DRIFVVEVRV NG.KTIATGK GRTKKEAEKE AARIAYEKIL KERS        240
Ec-RNase III    DQEFTIHCQV SGLSEPVVGT GSSRRKAEQA AAEQALKKLE LE..        226
                                      7
```

Fig. 6

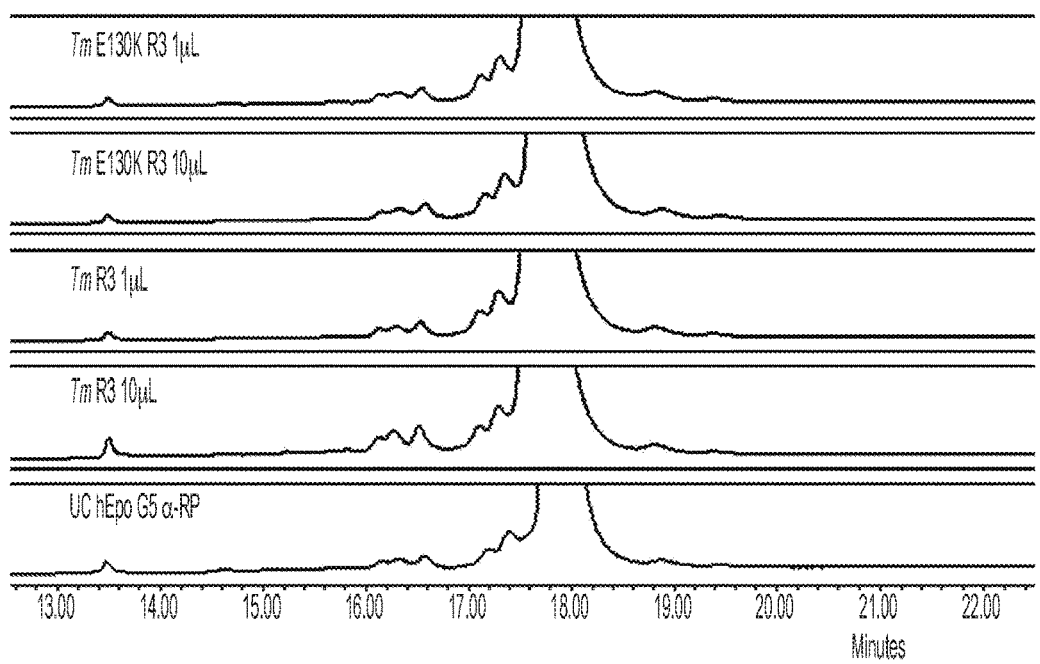

Fig. 7

RNA AFFINITY PURIFICATION

RELATED APPLICATIONS

This application is a national stage filing under 35 U.S.C. § 371 of international application number PCT/US2017/065962, filed Dec. 13, 2017, which was published under PCT Article 21(2) in English and claims the benefit under 35 U.S.C. § 119(e) of U.S. provisional application No. 62/433,352, filed Dec. 13, 2016, each of which is incorporated by reference herein in its entirety.

BACKGROUND

High-quality ribonucleic acid (RNA) is required for many different biomolecular and therapeutic applications; however, RNA synthesis reactions (e.g., in vitro transcription reactions) often generate contaminating double-stranded RNA (dsRNA) fragments that are difficult to separate from reaction mixtures containing a full-length, single-stranded RNA (ssRNA) product of interest.

SUMMARY

Provided herein are systems, compositions, and affinity purification methods for removing dsRNA contaminants from a nucleic acid preparation that includes a ssRNA (e.g., messenger RNA (mRNA)) product of interest. The affinity purification methods of the present disclosure are based, at least in part, on experimental results showing that immobilized ribonuclease III (RNase III) and immobilized catalytically inactive RNase III variants, as provided herein, bind specifically to dsRNA, without non-specific degradation of the ssRNA (e.g., mRNA) of interest.

Thus, some aspects of the present disclosure provide methods of purifying a nucleic acid (e.g., RNA) preparation that comprise contacting a nucleic acid preparation comprising messenger ribonucleic acid (mRNA) (e.g., an in vitro-transcribed mRNA) with an RNase III enzyme that is immobilized on a solid support (e.g., a resin). Typically, such a nucleic acid preparation comprises contaminating double-stranded RNA, therefore, affinity purification methods, as provided herein, may be performed under conditions that result in binding of the RNase III enzyme to double-stranded RNA.

In some embodiments, the RNase III enzyme is catalytically inactive. In some embodiments, the RNase III enzyme (e.g., a catalytically inactive RNase III enzymes) is a thermostable (e.g., *Thermotoga maritima*) RNase III enzyme.

In some embodiments, the RNase III enzyme comprises an amino acid sequence identified by SEQ ID NO: 3 (wild-type *Thermotoga maritima* RNase III (TmR3)). The RNase III enzyme may comprise, for example, an amino acid sequence having a modification at an amino acid position corresponding to E130 of the sequence identified by SEQ ID NO: 3. In some embodiments, the RNase in enzyme comprises an amino acid sequence identified by SEQ ID NO: 4 (variant *Thermotoga maritima* RNase III (E130K)).

Other aspects of the present disclosure provide methods that comprise performing an in vitro transcription reaction in the presence of a template nucleic acid (e.g., DNA) to produce an in vitro transcription product (e.g., RNA, such as mRNA), and contacting the in vitro transcription product with a RNase III enzyme (e.g., a catalytically inactive RNase III enzyme) that is immobilized on a solid support (e.g., a resin, such as a carboxy-reactive resin or an amino-reactive resin).

Further provided herein are compositions comprising RNA purified according to methods that comprise contacting a nucleic acid preparation comprising mRNA with an RNase III enzyme that is immobilized on a solid support. In some embodiments, the composition (e.g., comprising the purified RNA) is substantially free of double-stranded RNA.

Also provided herein are compositions containing RNA prepared according to a method that comprises performing an in vitro transcription reaction in the presence of a template nucleic acid (e.g., DNA) to produce an in vitro transcription product (e.g., mRNA); and contacting the in vitro transcription product with an RNase III enzyme that is immobilized on a solid support. In some embodiments, the composition is substantially free of double-stranded RNA.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

(FIG. 2C), 45° C. (FIG. 2B), or 65° C. (FIG. 2D), and the mixtures were analyzed on a size exclusion column. Non-specific degradation products were observed at all temperatures, with most degraded fragments of the mRNA observed at 65° C.

(FIG. 3C), 45° C. (FIG. 3B), or 65° C. (FIG. 3D), and the mixtures were analyzed on a size exclusion column. Non-specific degradation products were observed at room temperature, 45° C., and 65° C., with most degraded fragments of the mRNA observed at 65° C.

(FIG. 4C), 45° C. (FIG. 4B), or 65° C. (FIG. 4D) and the mixtures were analyzed on a size exclusion column. Non-specific degradation products were observed at all temperatures, with most degraded fragments of the mRNA observed at 65° C.

(FIG. 5C), 45° C. (FIG. 5B), or 65° C. (FIG. 5D) and the mixtures were analyzed on a size exclusion column. Non-specific degradation products were observed at 37° C. and 65° C., with most degraded fragments of the mRNA observed at 65° C.

FIG. 6 shows a sequence alignment of the RNase III protein sequences from *Aquifex aeolicus* (top sequence, SEQ ID NO: 5), *Thermotoga maritima* (middle sequence, SEQ ID NO: 3) and *Escherichia coli* (bottom sequence, SEQ ID NO: 1).

FIG. 7 shows spectrums from a reverse-phase HPLC used to detect non-specific RNase contamination in a purified TmR3-E130K mutant. 20 μg of human erythropoietin (hEPO) mRNA containing a 5' cap analog 7mG(5)ppp(5') NlmpNp (G5) was incubated in reactions mixtures containing the designated purified enzymes at room temperature for 1 hour, and the mixtures were analyzed on a size exclusion column. No detectable non-specific RNase was present.

DETAILED DESCRIPTION

Figure 1:
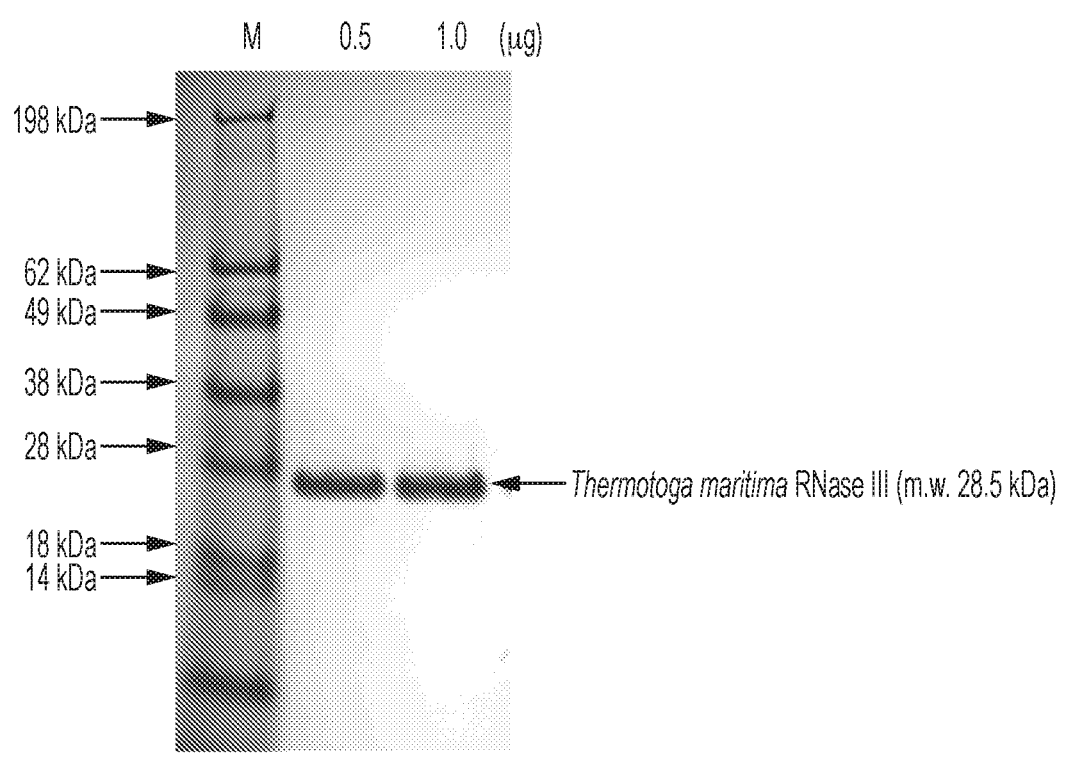
FIG. 1 shows a Coomassie blue stained polyacrylamide gel. *Thermotoga maritima* RNase III (TmR3) was expressed and purified by Ni-NTA affinity column to >99% purity. Different amounts (0.5 µg or 1 µg) of the purified TmR3 were resolved on the polyacrylamide gel. The molecular weight of TmR3 is 28.5 kDa.
Figure 2A:
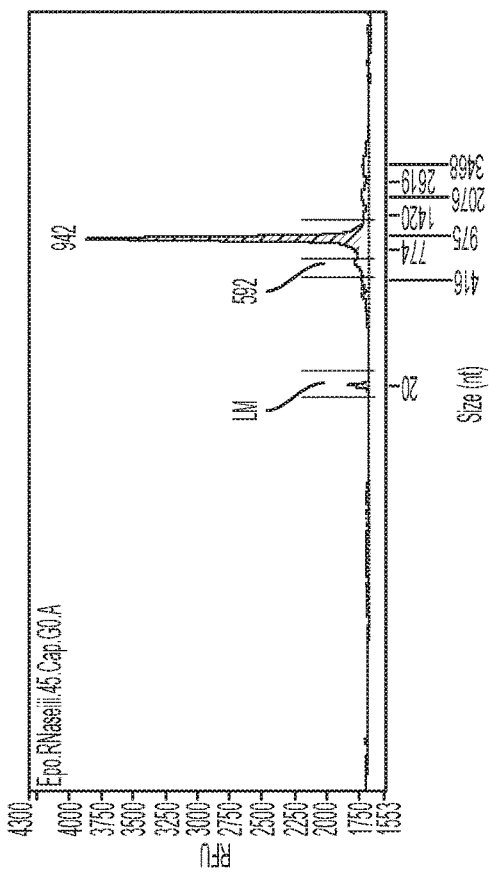
FIGS. 2A-2D show spectrums from a size-exclusion experiment used to analyze the degradation of mRNAs by TmR3 at different temperatures. A human erythropoietin (hEpo) mRNA containing a natural 5' cap (G0) was incubated in reaction mixtures containing purified TmR3 at room temperature (FIG. 2A), 37° C.
Figure 2B:
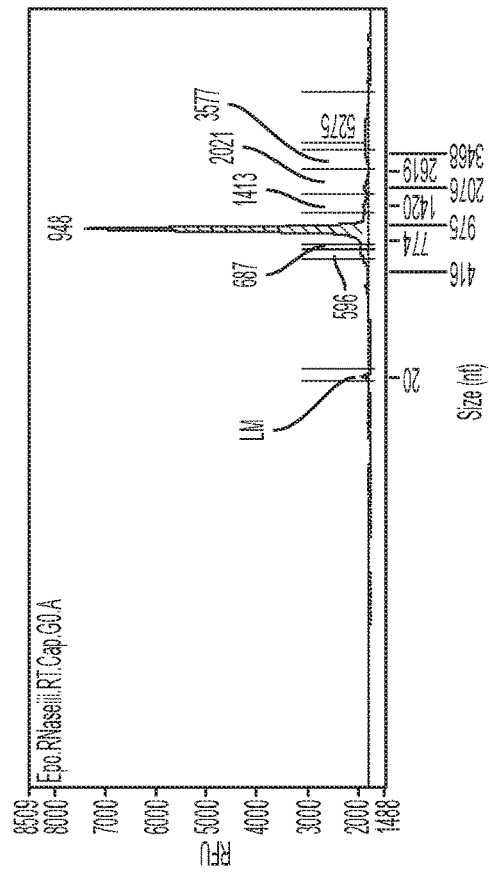
Figure 2C:
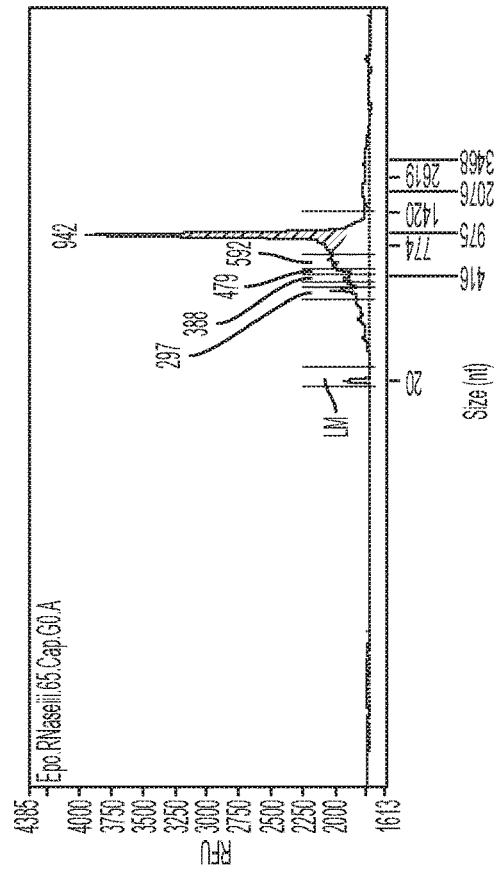
Figure 2D:
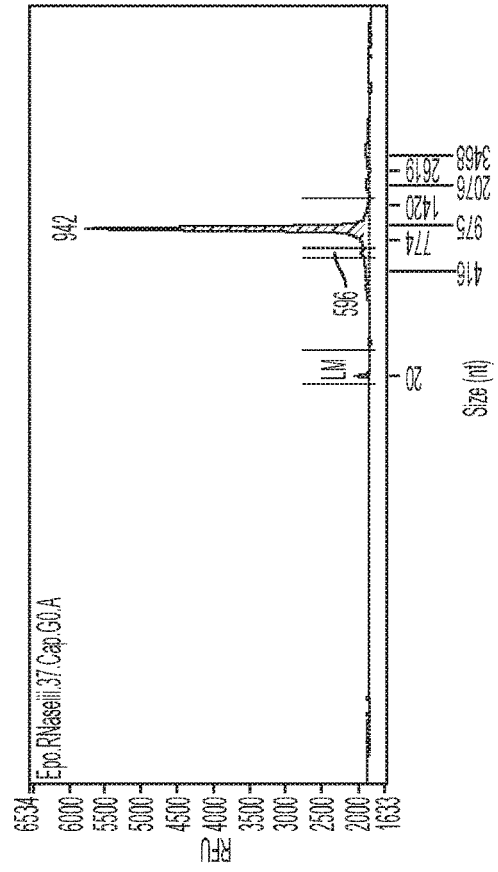
Figure 3B:
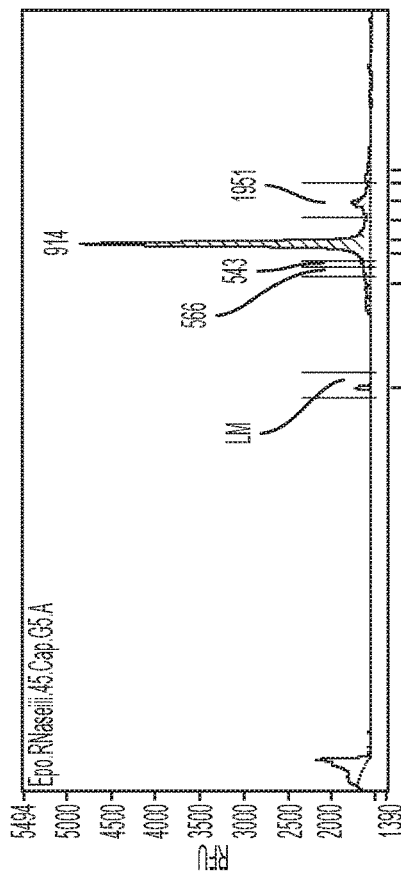
FIGS. 3A-3D show spectrums from a size-exclusion experiment designed to analyze the degradation of mRNAs by TmR3 at different temperatures. A human erythropoietin (hEPO) mRNA containing a 5' cap analog 7mG(5')ppp(5')NlmpNp (G5) was incubated in reaction mixtures containing purified TmR3 at room temperature (FIG. 3A), 37° C.
Figure 3D:
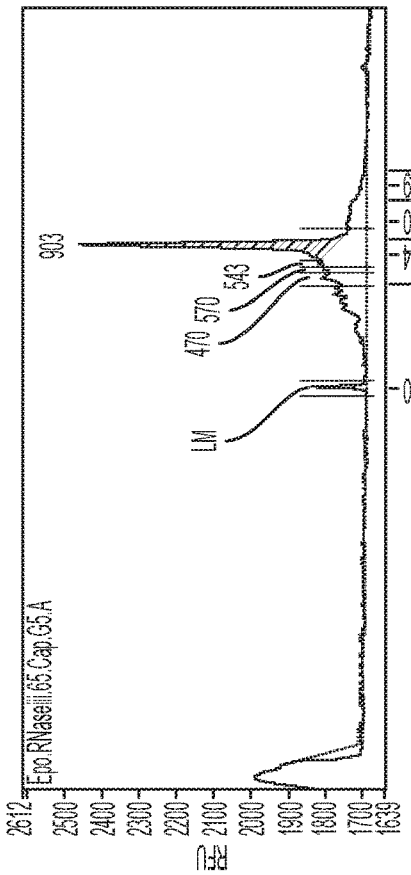
Figure 3A:
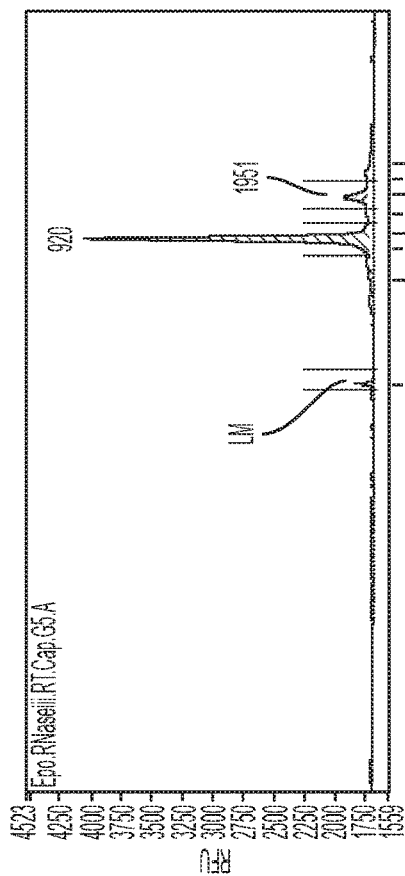
Figure 3C:
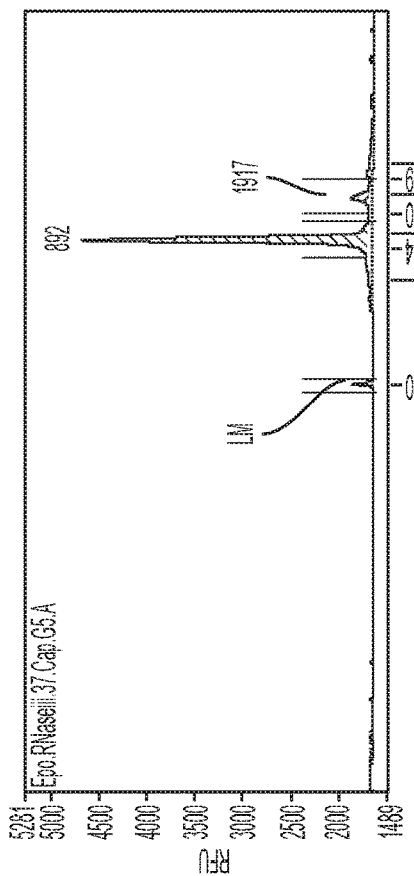
Figure 4A:
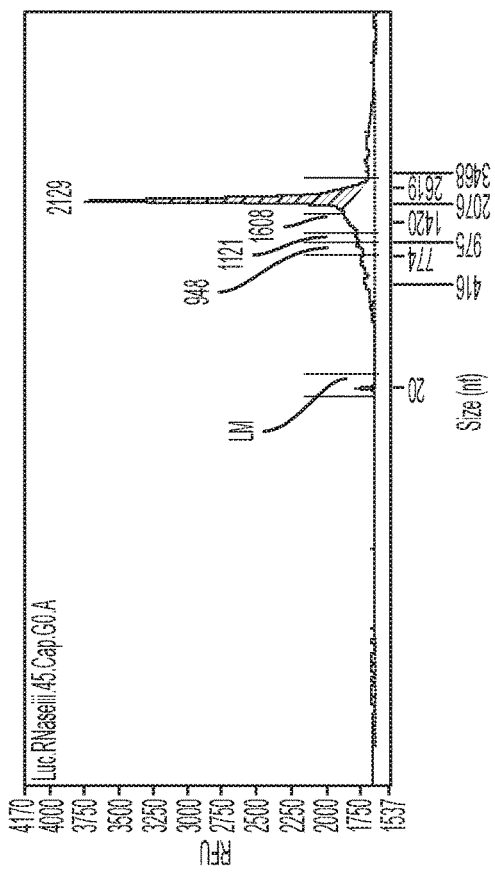
FIGS. 4A-4D show spectrums from a size-exclusion experiment designed to analyze the degradation of mRNAs by TmR3 at different temperatures. A luciferase (Luc) mRNA containing a natural 5' Cap (G0) was incubated with purified TmR3 at room temperature (FIG. 4A), 37° C.
Figure 4B:
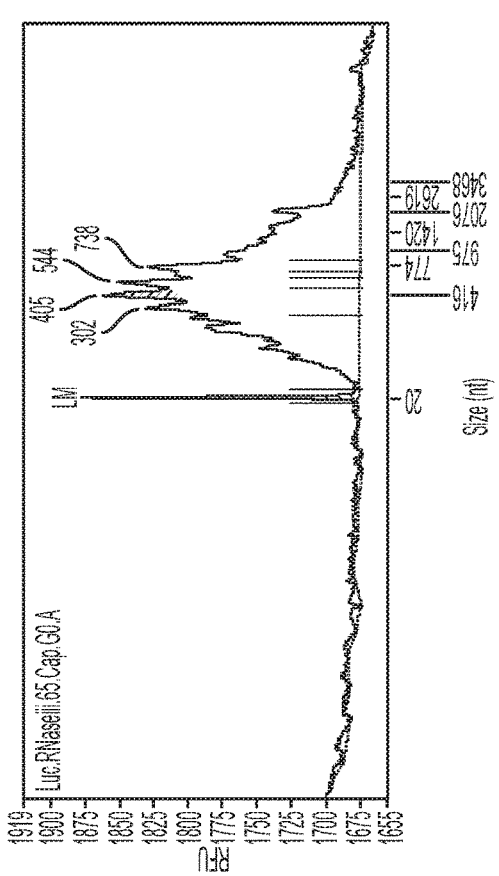
Figure 4C:
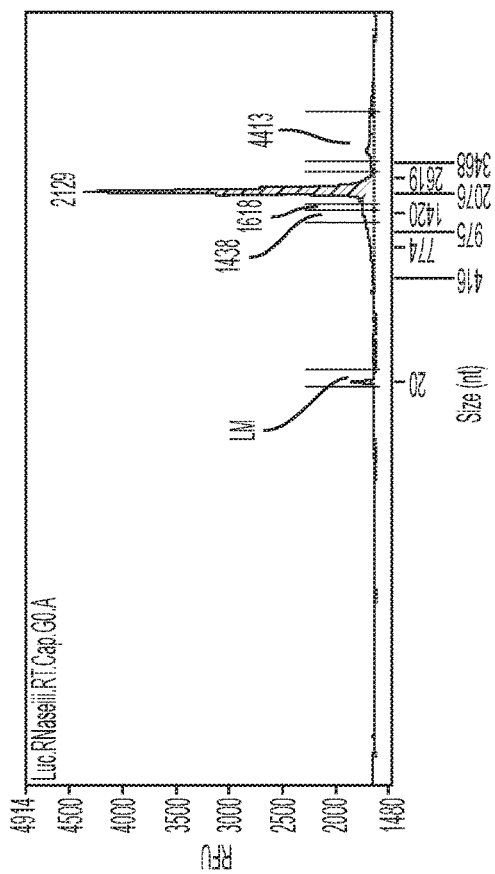
Figure 4D:
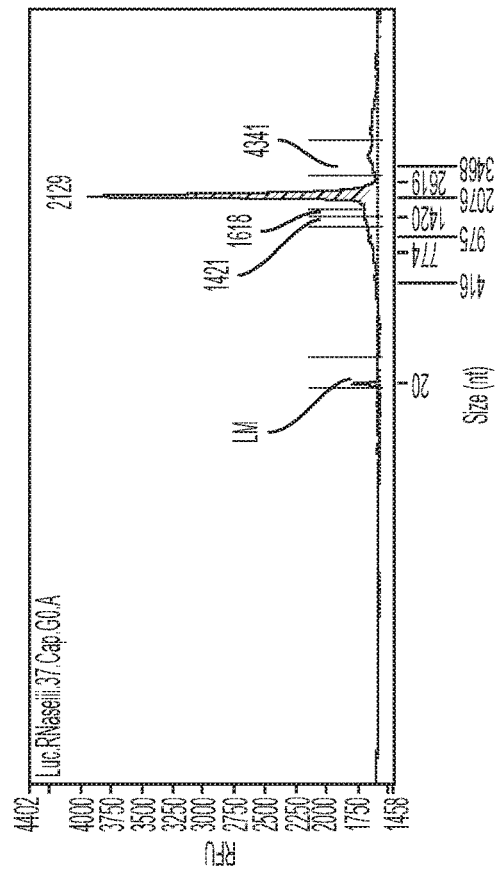
Figure 5A:
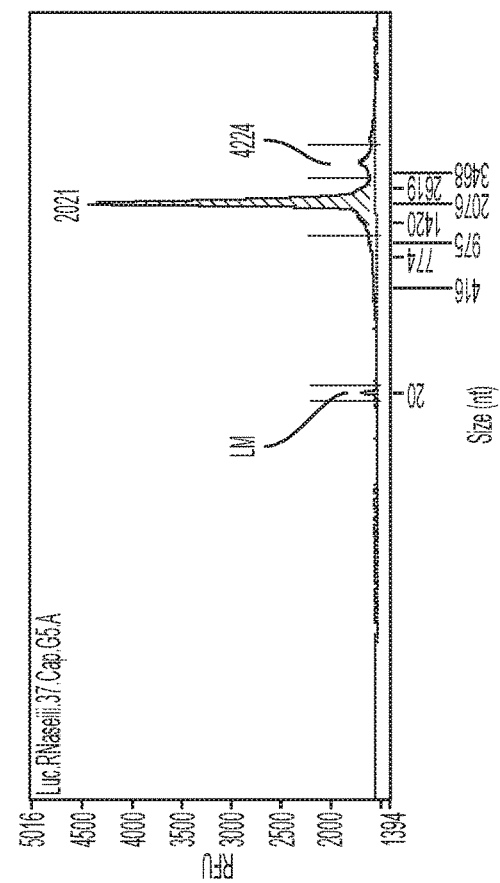
FIGS. 5A-5D show spectrums from a size-exclusion experiment designed to analyze the degradation of mRNAs by TmR3 at different temperatures. A luciferase (Luc) mRNA containing a 5' cap analog 7mG(5')ppp(5')NlmpNp (G5) was incubated in reaction mixtures containing purified TmR3 at room temperature (FIG. 5A), 37° C.
Figure 5C:
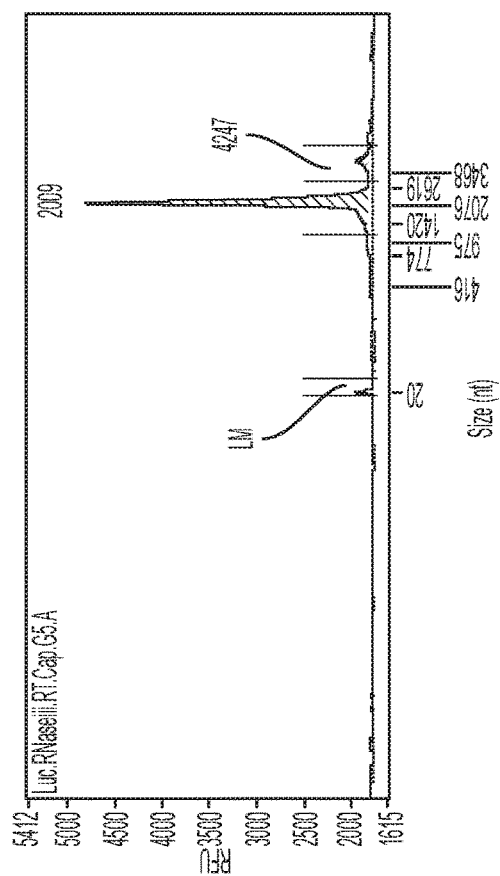
Figure 5B:
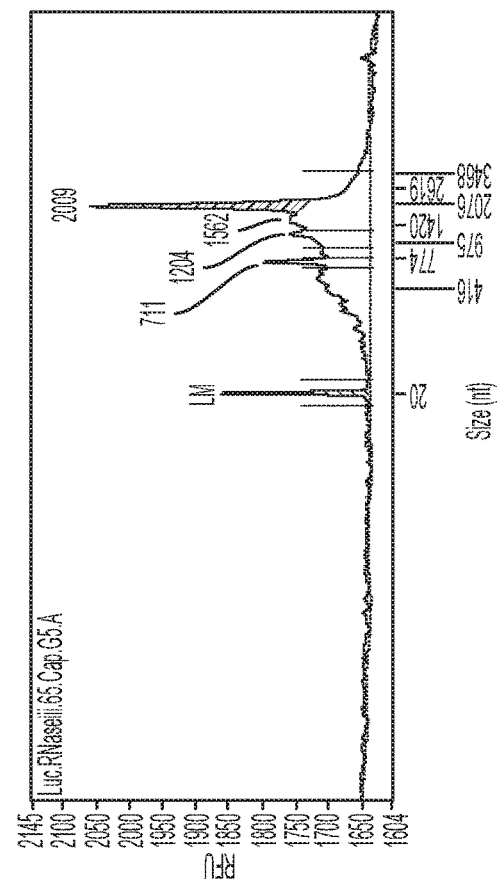
Figure 5D:
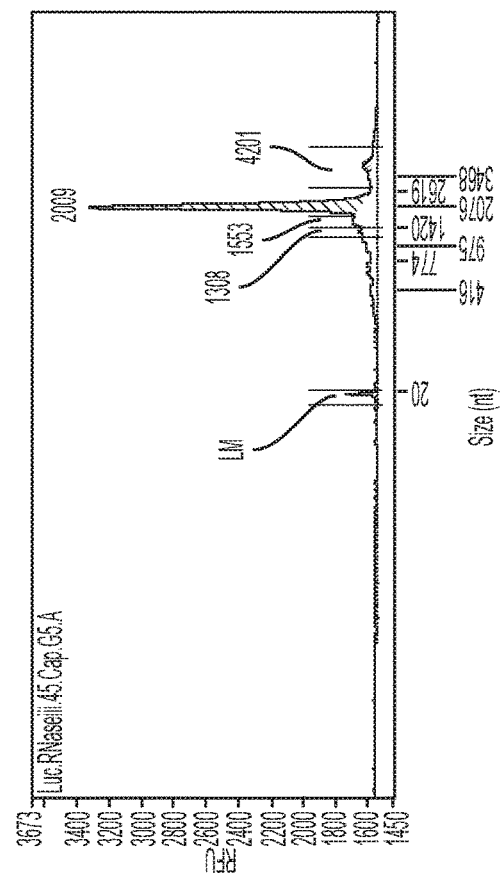

The product of ribonucleic acid (RNA) synthesis reactions, such as in vitro transcription (IVT) reactions, often contains some amount of contaminating RNA, including double-stranded RNA. Such contaminants can adversely impact downstream molecular and therapeutic application, for example. Provided herein are methods of removing specifically dsRNA contaminants from a RNA preparation. More generally, the present disclosure provides methods of purifying a nucleic acid preparation. The methods may comprise, for example, contacting a nucleic acid preparation with a RNase III enzyme that is immobilized on a solid support.

Affinity Purification Using RNase III Enzymes

RNA synthesis reactions, such as in vitro transcription reactions, typically produce an end product preparation that includes a mixture of different nucleic acid species. Purification of the intended single-stranded species is typically required prior to its use in any particular application (e.g., therapeutic application). Thus, affinity purification methods as provided herein are typically used to purify a "nucleic acid preparation," which is simply a solution comprising nucleic acid, for example, a mixture of different nucleic acid species (e.g., full-length and truncated ssRNA, dsRNA, dsDNA, etc.). In some embodiments, a nucleic acid preparation is the end product of an in vitro transcription reaction (for example, using bacteriophage T7 RNA polymerase (e.g., as described in Donzeet et al., Nucleic Acids Res 30:e46, 2002; and Yu et al., *Proc Natl Acad Sci USA* 99:6047-6052, 2002)). RNA (e.g., mRNA) preparations produced by IVT often contain contaminants, such as nucleic acid contaminants (e.g., DNA template) and protein contaminants (e.g., T7 RNA polymerase). Methods of removing DNA contaminants (e.g., via digestion of the DNA by DNases) or protein contaminants (e.g., via pheno-chloroform precipitation) from an RNA preparation are known. Additional contaminate include truncated fragments of the ssRNA (e.g., mRNA) of interest generated by the T7 RNA polymerase. In some instances, these truncated fragments contain complementary species and form double-stranded RNA (dsRNA) species (e.g., as described in Kariko et al., *Nucleic Acids Research*, 2011, Vol. 39, No. 21, e142, 2009). It is difficult to separate such dsRNA contaminants from the desired ssRNA because the dsRNA contaminants and the ssRNA have very similar biochemical and biophysical properties.

Provided herein are affinity purification methods that use immobilized RNase III, and in some embodiments, immobilized catalytically inactive RNase III variants, that specifically bind to (and thus capture) dsRNA species from a RNA preparation, without non-specific degradation of the intended ssRNA (e.g., mRNA) product, as discussed in greater detail herein. The affinity purification methods makes use of specific binding interactions between RNase III and double-stranded RNA. RNase III (or a catalytically inactive variant thereof) is chemically immobilized or "coupled" to a solid support so that when a nucleic acid preparation is passed over the solid support (e.g., column), dsRNA molecules become bound to the RNase III. The "flow through" fraction is essentially free of dsRNA contaminants.

Thus, a nucleic acid preparation may be "purified" using affinity purification methods of the present disclosure, optionally in combination with other purification methods that remove DNA and protein contaminants. "Purification," generally, refers to a process (one or more steps) of isolating one particular species (e.g., mRNA) or a subgroup of species from a larger group of species (e.g., a combination of RNA, DNA and protein). A purification process results in enrichment of the RNA of interest.

In some embodiments, purification can be partial (e.g., as in fractionation). In some embodiments, purification yields RNA of interest that is substantially free of other, chemically dissimilar types of molecules. For example, nucleic acids are purified from mixtures comprising proteins, lipids, carbohydrates, etc. In some embodiments, purification results in a RNA of interest that is in pure form, i.e., free or substantially free from all other substances, whether chemically similar or not. Being "substantially free of" a substance (e.g., protein, carbohydrates, lipids, and other nucleic acids) means the RNA of interest comprises less than 20%, less than 10%, less than 18%, less than 17%, less than 16%, less than 15%, less than 14%, less than 135, less than 12%, less than 11%, less than 10%, less than 9%, less than 8%, less than 7%, less than 6%, less than 5%, less than 4%, less than 3%, less than 2%, less than 1%, less than 0.5%, less than 0.1%, or less than 0.01% of the substance by weight or by molarity. In some embodiments, to reach its pure form, a RNA of interest may be subjected to more than one purification process (in addition to the affinity purification methods of as provided herein).

RNase III Enzymes. Riponuclease III (RNase III) is an endoribonuclease that binds to and cleaves double stranded RNA. The enzyme is expressed in many organisms and is highly conserved (e.g., Mian et al., *Nucleic Acids Res.*, 1997, 25, 3187-95). RNase III species cloned to date contain an RNase III signature sequence and vary in size from 25 to 50 kDa. Multiple functions have been ascribed to RNase III. In both *Escherichia coli* and *Saccharomyces cerevisiae*, RNase III is involved in the processing of pre-ribosomal RNA (pre-rRNA) (e.g., Elela et al., *Cell,* 1996, 85, 115-24). RNase III is also involved in the processing of small molecular weight nuclear RNAs (snRNAs) and small molecular weight nucleolar RNAs (snoRNAs) in *S. cerevisiae* (e.g., Chanfreau et al., *Genes Dev.* 1996, 11, 2741-51; Qu et al., *Mol. Cell. Biol.* 1996, 19, 1144-58). In *E. coli*, RNase III is involved in the degradation of some mRNA species (e.g., Court et al., *Control of messenger RNA stability,* 1993, Academic Press, Inc, pp. 71-116).

There are several types of *Drosophila* and *Caenorhabditis elegans* RNase III enzymes. The canonical RNase III contains a single RNase III signature motif and a double-stranded RNA binding domain (dsRBD; e.g. RNC-_CAEEL). Drosha (Filippov et al. (2000) Gene 245: 213-221) is a *Drosophila* enzyme that contains two RNase III motifs and a dsRBD (CeDrosha in *C. elegans*). Another type of RNase III enzyme contains two RNase III signatures and an amino terminal helicase domain (e.g. *Drosophila* CG4792, CG6493, *C. elegans* K12H4.8) and may be RNAi nucleases (Bass (2000) Cell 101: 235-238). Enzymes from each *Drosophila* and *Caenorhabditis elegans* type produce discrete ~22 nucleotide (nt) RNAs from dsRNA substrates. Some RNase III enzymes specifically bind to dsRNA molecules without cleaving the dsRNA (e.g., Blaszczyk et al., *Structure*, vol. 12, 457-466, 2004).

RNase III enzymes that may be used in accordance with the present disclosure include RNase III enzymes that specifically bind to dsRNA. A RNase III enzyme may be a bacterial enzyme or a eukaryotic (e.g., mammalian) enzyme. In some embodiments, a RNase III is an *E. coli* RNase III (EcR3). In some embodiments, a RNase III is a *T. maritima* RNase III. In some embodiments, a RNase III is an *Aquifex aeolicus* RNase III (AaR3). In some embodiments, a RNase III is a human RNase III.

Immobilized RNase III. RNase III enzymes and catalytically inactive variants thereof are immobilized on a solid support and then contacted with a nucleic acid preparation containing, for example, a mixture of single-stranded and double-stranded DNA. Immobilized RNase III, when in contact with double-stranded RNA (dsRNA) binds to (captures) the dsRNA such that the dsRNA remains associated with the solid support. RNase III is considered "immobilized" on a solid support when the enzyme is covalently or non-covalently attached to the support such that the enzyme does not dissociate from the support when contacted with a pH neutral buffered solution.

A solid support may be a substance with a surface to which a RNase III enzyme or variant can be attached such that the polypeptide becomes immobilized with respect to the solid support. A solid support of the present disclosure may be fabricated from one or more suitable materials, for example, plastics or synthetic polymers (e.g., polyethylene, polypropylene, polystyrene, polyamide, polyurethane, phenolic polymers, and/or nitrocellulose), naturally derived polymers (e.g., latex rubber, polysaccharides, and/or polypeptides), composite materials, ceramics, silica or silica-based materials, carbon, metals or metal compounds (e.g., comprising gold, silver, steel, aluminum, or copper), inorganic glasses, silica, and a variety of other suitable materials. Non-limiting examples of potentially suitable configurations include resins (e.g., agarose resin), beads (e.g., magnetic beads), tubes nanotubes), plates, disks, dipsticks, chips, microchips, coverslips, or the like.

Surface compositions that may be used to immobilize RNase III or a variant thereof (e.g., catalytically inactive RNase III) are available. For example, the surface of the support may comprise reactive functional groups that form covalent bonds with RNase III or a variant thereof. In some embodiments, the functional groups are chemical functionalities. That is, the binding surface may be derivatized such that a chemical functionality is presented at the binding surface, which can react with a chemical functionality on polypeptide to be attached, resulting in immobilization. Examples of functional groups for attachment that may be useful include, but are not limited to, amino-reactive groups, carboxyl-reactive groups, epoxide groups, maleimide groups, oxo groups, and thiol groups. Functional groups can be attached, either directly or indirectly through the use of a linker, the combination of which is sometimes referred to as a "crosslinker." Crosslinkers for attaching proteins to a support member are known in the art; for example, homo-or hetero-bifunctional crosslinkers as are well known (e.g., see 1994 Pierce Chemical Company catalog, technical section on crosslinkers, pages 155-200, or "Bioconjugate Techniques" by Greg T. Hermanson, Academic Press, 1996). Non-limiting example of crosslinkers include alkyl groups (including substituted alkyl groups and alkyl groups containing heteroatom moieties), esters, amide, amine, epoxy groups and ethylene glycol and derivatives. A linker may also be a sulfone group, forming a sulfonamide. In some embodiments, the functional group is a light-activated functional group. That is, the functional group can be activated by light to attach the capture component to the capture object surface. One example is PhotoLink™ technology available from SurModics, Inc. in Eden Prairie, Minn. The examples provided herein on the solid support and the surface composition are not meant to be limiting. Any solid support that are known in the art to be suitable for immobilization of polypeptides may be used in accordance with the present disclosure. Immobilization of RNase III to a solid support is carried out under conditions that maintains the structure and activity of RNase III. One skilled in the art is familiar with such conditions.

Exemplary RNase III Enzymes. Any RNase III or variant thereof (e.g., catalytically inactive variant) that binds specifically to dsRNA may be used in accordance with the present disclosure. Non-limiting examples of RNase III enzymes and catalytically inactivate RNase III variants are listed in Table 1.

TABLE 1

Examples of RNase III Enzymes

| Host | Amino Acid Sequence |
|---|---|
| *Escherichia coli* (wild type) | MNPIVINRLQRKLGYTFNHQELLQQALTHRSASSKH NERLEFLGDSILSYVIANALYHRFPRVDEGDMSRMR ATLVRGNTLAELAREFELGECLRLGPGELKSGGFRR ESILADTVEALIGGVFLDSDIQTVEKLILNWYQTRLD EISPGDKQKDPKTRLQEYLQGRHLPLPTYLVVQVRG EAHDQEFTIHCQVSGLSEPVVGTGSSRRKAEQAAAE QALKKLELE (SEQ ID NO: 1) |

TABLE 1-continued

Examples of RNase III Enzymes

| Host | Amino Acid Sequence |
|---|---|
| Escherichia coli (E117K) | MNPIVINRLQRKLGYTFNHQELLQQALTHRSASSKH NERLEFLGDSILSYVIANALYHRFPRVDEGDMSRMR ATLVRGNTLAELAREFELGECLRLGPGELKSGGFRR ESILADTVKALIGGVFLDSDIQTVEKLILNWYQTRLD EISPGDKQKDPKTRLQEYLQGRHLPLPTYLVVQVRG EAHDQEFTIHCQVSGLSEPVVGTGSSRRKAEQAAAE QALKKLELE (SEQ: ID NO: 2) |
| Thermotoga maritima (wild type) | MNESERKIVEEFQKETGINFKNEELLFRALCHSSYAN EQNQAGRKDVESNEKLEFLGDAVLELFVCEILYKKY PEAEVGDLARVKSAAASEEVLAMVSRKMNLGKFLF LGKGEEKTGGRDRDSILADAFKALLAAIYLDQGYEK IKELFEQEFEFYIEKIMKGEMLFDYKTALQEIVQSEH KVPPEYILVRTEKNDGDRIFVVEVRVNGKTIATGKG RTKKEAEKEAARIAYEKLLKERS (SEQ ID NO: 3) |
| Thermotoga maritima (E130K) | MNESERKIVEEFQKETGINFKNEELLFRALCHSSYAN EQNQAGRKDVESNEKLEFLGDAVLELFVCEILYKKY PEAEVGDLARVKSAAASEEVLAMVSRKMNLGKFLF LGKGEEKTGGRDRDSILADAFKALLAAIYLDQGYEK IKELFEQEFEFYIEKIMKGEMLFDYKTALQEIVQSEH KVPPEYILVRTEKNDGDRIFVVEVRVNGKTIATGKG RTKKEAEKEAARIAYEKLLKERS (SEQ ID NO: 4) |
| Aquifex aeolicus (wild type) | MKMLEQLEKKLGYTFKDKSLLEKALTHVSYSKKEH YETLEFLGDALVNFFIVDLLVQYSPNKREGFLSPLKA YLISEEFFNLLAQKLELHKFIRIKRGKINETIIGDVF EALWAAVYIDSGRDANFTRELFYKLFKEDILSAIKEG RVKKDYKTILQEITQKRWKERPEYRLISVEGPHHKKK FIVEAKIKEYRTLGEGKSKKEAEQRAAEELIKLLEES E (SEQ ID NO: 5) |
| Aquifex aeolicus (E110K) | MKMLEQLEKKLGYTFKDKSLLEKALTHVSYSKKEH YETLEFLGDALVNTFFIVDLLVQYSPNKREGFLSPLK AVLISEEFFNLLAQKLELHKFIRIKRGKINETIIGDV FKALWAAVYIDSGRDANFTRELFYKLFKEDILSAIKE GRVKKDYKTILQEITQKRWKERPEYRLISVEGPHHKK KFIVEAKIKEYRTLGEGKSKKEAEQRAAEELIKLLEE SE (SEQ ID NO: 6) |

*Escherichia coli* RNase III. In some embodiments, a RNase III used in the affinity purification methods as provided herein comprises the amino acid sequence identified by SEQ ID NO: 1. In some embodiments, a RNase III comprises an amino acid sequence that is at least 80% identical to the amino acid sequence identified by SEQ ID NO: 1. For example, a RNase III may comprise an amino acid sequence that is at least 80%, at least 85%, at least 90%, at least 95%, or at least 99% identical to the amino acid sequence identified by SEQ ID NO: 1. In some embodiments, a RNase III comprises an amino acid sequence that is 80%, 85%, 90%, 95%, 96%, 97%, 98%, or 99% identical to the amino acid sequence identified by SEQ ID NO: 1.

In some embodiments, a RNase III used in the affinity purification methods as provided herein comprises the amino acid sequence identified by SEQ ID NO: 1 having an amino acid substitution mutation at position E117. In some embodiments, a RNase III comprises an amino acid sequence that is at least 80% identical to the amino acid sequence identified by SEQ ID NO: 1 having a lysine (K) at position 117 (E117K). For example, a RNase III may comprise an amino acid sequence that is at least 80%, at least 85%, at least 90%, at least 95%, or at least 99% identical to the amino acid sequence identified by SEQ ID NO: 1 having a lysine (K) at position 117 (E117K). In some embodiments, a RNase III comprises an amino acid sequence that is 80%, 85%, 90%, 95%, 96%, 97%, 98%, or 99% identical to the amino acid sequence identified by SEQ ID NO: 1 having a lysine (K) at position 117 (E117K). In some embodiments, the RNase III used in the affinity purification methods as provided herein comprises the amino acid sequence identified by SEQ ID NO: 2.

*Thermotoga maritima* RNase III. In some embodiments, a RNase III used in the affinity purification methods as provided herein comprises the amino acid sequence identified by SEQ ID NO: 3. In some embodiments, a RNase III comprises an amino acid sequence that is at least 80% identical to the amino acid sequence identified by SEQ ID NO: 3. For example, a RNase III may comprise an amino acid sequence that is at least 80%, at least 85%, at least 90%, at least 95%, or at least 99% identical to the amino acid sequence identified by SEQ ID NO: 3. In some embodiments, a RNase III comprises an amino acid sequence that is 80%, 85%, 90%, 95%, 96%, 97%, 98%, or 99% identical to the amino acid sequence identified by SEQ ID NO: 3.

In some embodiments, a RNase III used in the affinity purification methods as provided herein comprises the amino acid sequence identified by SEQ ID NO: 3 having an amino acid substitution mutation at position E130. In some embodiments, a RNase ill comprises an amino acid sequence that is at least 80% identical to the amino acid sequence identified by SEQ ID NO: 3 having a lysine (K) at position 130 (E130K). For example, a RNase III may comprise an amino acid sequence that is at least 80%, at least 85%, at least 90%, at least 95%, or at least 99% identical to the amino acid sequence identified by SEQ ID NO: 3 having a lysine (K) at position 130 (E130K). In some embodiments, a RNase III comprises an amino acid sequence that is 80%, 85%, 90%, 95%, 96%, 97%, 98%, or 99% identical to the amino acid sequence identified by SEQ ID NO: 3 having a lysine (K) at position 130 (E130K). In some embodiments, the RNase III used in the affinity purification methods as provided herein comprises the amino acid sequence identified by SEQ ID NO: 4.

*Aquifex aeolicus* RNase III. In some embodiments, a RNase III used in the affinity purification methods as provided herein comprises the amino acid sequence identified by SEQ ID NO: 5. In some embodiments, a RNase III comprises an amino acid sequence that is at least 80% identical to the amino acid sequence identified by SEQ ID NO: 5. For example, a RNase III may comprise an amino acid sequence that is at least 80%, at least 85%, at least 90%, at least 95%, or at least 99% identical to the amino acid sequence identified by SEQ ID NO: 5. In some embodiments, a RNase III comprises an amino acid sequence that is 80%, 85%, 90%, 95%, 96%, 97%, 98%, or 99% identical to the amino acid sequence identified by SEQ ID NO: 5.

In some embodiments, a RNase III used in the affinity purification methods as provided herein comprises the amino acid sequence identified by SEQ ID NO: 5 having an amino acid substitution mutation at position E110. In some embodiments, a RNase III comprises an amino acid sequence that is at least 80% identical to the amino acid sequence identified by SEQ ID NO: 5 having a lysine (K) at position 110 (E110K). For example, a RNase III may comprise an amino acid sequence that is at least 80%, at least 85%, at least 90%, at least 95%, or at least 99% identical to the amino acid sequence identified by SEQ ID NO: 5 having a lysine (K) at position 110 (E110K). In some embodiments, a RNase III comprises an amino acid sequence that is 80%, 85%, 90%, 95%, 96%, 97%, 98%, or 99% identical to the amino acid sequence identified by SEQ ID NO: 5 having a lysine (K) at position 110 (E110K). In some embodiments, the RNase III used in the affinity purification methods as provided herein comprises the amino acid sequence identified by SEQ NO: 6.

Thermostable RNase III

Affinity purification method performed at elevated temperatures (e.g., greater than 70° C.) may reduce the formation of intramolecular (secondary) structure within ssRNA (e.g., mRNA). Thus, in some embodiments, a thermostable RNase III (e.g., *Thermotoga maritima* RNase III) may be used to remove dsRNA from a nucleic acid (e.g., IVT RNA) preparation.

"Thermostability" refers to the quality of enzymes to resist denaturation at high relative temperature. For example, if an enzyme is denatured (inactivated) at a temperature of 42° C., an enzyme having similar activity (e.g., exonuclease activity) is considered "thermostable" if it does not denature at 42° C. An enzyme (e.g., RNase III) is considered thermostable if the enzyme (a) retains activity (e.g., at least 50% activity) after temporary exposure to high temperatures that denature other non-thermostable enzymes or (b) functions at a high rate (e.g., greater than 50%) after temporary exposure to a medium to high temperature where non-thermostable enzymes function at low rates.

In some embodiments, a thermostable RNase III (e.g., *Thermotoga maritima* RNase III) retains greater than 50% activity (e.g., dsRNA binding and/or cleavage activity) following temporary exposure to high relative temperature (e.g., higher than 70° C. for *Thermotoga maritima* RNase III) that would otherwise denature a similar non-thermostable RNase III. In some embodiments, a thermostable RNase III retains 50-100% activity following temporary exposure to high relative temperature (e.g., at least 70, 80, 90, or 95° C.) that would otherwise denature a similar non-thermostable RNase III. For example, a thermostable RNase III may retain 50-90%, 50-85%, 50-80%, 50-75%© 50-70%, 50-65%, 50-60%, or 50-55% activity following temporary exposure to high relative temperature that would otherwise denature a similar non-thermostable RNase III. In some embodiments, a thermostable RNase III retains 25%, 30%, 35%, 40%, 45%, 50%, 55%, 60%, 65%, 70%, 75%, 80%, 85%, 90%, 95%, 98%, 99%, or 100% activity following temporary exposure to high relative temperature that would otherwise denature a similar non-thermostable RNase III. In some embodiments, the activity of a thermostable RNase III after temporary exposure medium to high temperature is greater than (e.g., 25%, 30%, 35%, 40%, 45%, 50%, 55%, 60%, 65%, 70%, 75%, 80%, 85%, 95%, 98%, 99%, or 100% greater than) the activity of a similar non-Thermostable RNase III.

Thermostable RNase III may remain active (able to bind and/or cleave dsRNA) at a temperatures of 40° C. to 95° C., or higher. In some embodiments, thermostable RNase III remain active at a temperature of 40-95° C., 40-90° C., 40-85° C., 40-80° C., 40-70° C., 40-60° C., 40-50° C., 40-45° C., 45-95° C., 45-90° C., 45-80° C., 45-70° C., 45-60° C., 45-50° C., 50-95° C., 50-90° C., 50-80° C., 50-70° C., 50-60° C., 60-95° C., 60-90° C., 60-80° C., 60-70° C., 70-95° C., 70-90° C., or 70-80° C. For example, thermostable RNase III may remain active at a temperature of 40° C., 41° C., 42° C., 43° C., 44° C., 45° C., 46° C., 47° C., 48° C., 49° C., 50° C., 51° C., 52° C., 53° C., 54° C., 55° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., or 100° C.

Thermostable RNase III may remain active at high relative temperatures for 15 minutes to 48 hours, or longer. For example, thermostable RNase III may remain active at high relative temperatures for 1, 2, 3, 4, 5, 6, 7, 8, 9, 10, 11, 12, 13, 14, 15, 16, 17, 18, 19, 20, 24, 36, 42, or 48 hours.

Methods of measuring the activity (e.g., dsRNA binding and/or cleavage) activity of RNase III is known to those skilled in the art. For example, the dsRNA binding activity may be monitored by an electrophoretic mobility shift assay (EMSA), using radioactive isotope (e.g., $^{32}$P) or fluorescent dye labeled dsRNA substrates, and the dsRNA cleavage activity may be monitored by the emergence of RNA cleavage products.

Catalytically Inactive RNase III

Some aspects of the present disclosure provide catalytically-inactive RNase III variants that may be used for the affinity purification methods. Use of catalytically-inactive RNase III variants in the affinity purification methods prevent/reduce the occurrence of non-specific cleavage of ssRNA (e.g., mRNA) of interest. A "catalytically inactive" form of RNase III is one the specifically binds to but does not cleave double-stranded RNA. Catalytically inactive forms of RNase III, therefore, may have at least one mutation (relative to wild-type RNase III) that impairs the endonucleolytic activity of the enzyme. Non-limiting examples of catalytically inactive RNase III enzymes are listed in Table 1. Thus, in some embodiments, a RNase III used in the affinity purification methods as provided herein is an *Escherichia coli* RNase III variant comprising the amino acid sequence of SEQ ID NO: 1 having a lysine (K) residue at position 117 (e.g., SEQ ID NO: 2; E117K). In some embodiments, a RNase III used in the affinity purification methods as provided herein is an *Thermotoga maritima* RNase III variant comprising the amino acid sequence of SEQ ID NO: 3 having a lysine (K) residue at position 130 (e.g., SEQ ID NO: 4; E130K). In some embodiments, a RNase III used in the affinity purification methods as provided herein is an *Aquifex aeolicus* RNase III variant comprising the amino acid sequence of SEQ ID NO: 5 having a lysine (K) residue at position 130 (e.g., SEQ ID NO: 6; E110K). Other catalytically inactive RNase III variants may be used in accordance with the present disclosure, provided the variants bind specifically to double-stranded RNA.

RNase III Homologs and Fragments

RNase III homologs and fragments are also within the scope of the present disclosure. Thus, provided herein are RNase III fragments (polypeptide sequences at least one amino acid residue shorter than a reference full-length RNase in enzyme sequence but otherwise identical) having a length of 10, 20, 30, 40, 50, 60, 70, 80, 90, 100 or greater than 100 amino acids. Any RNase III polypeptide that includes a stretch of 20, 30, 40, 50, 60, 70, 80, 90, or 100 amino acids that are 40%, 50%, 60%, 70%, 80%, 90%, 95%, or 100% identical to any of the RNase III sequences described herein may be utilized in an affinity purification method of the present disclosure, provided the polypeptide binds specifically to dsRNA (without non-specific cleavage of ssRNA).

"Identity" herein refers to the overall relatedness among polypeptides, for example, among RNase III and variants thereof. The percent identity of two polypeptide sequences, for example, can be calculated by aligning the two sequences for optimal comparison purposes (e.g., gaps can be introduced in one or both of a first and a second nucleic acid sequences for optimal alignment and non-identical sequences can be disregarded for comparison purposes). In some embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two amino acid sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. Techniques for determining identity are codified in publicly available computer programs. Exemplary computer software to determine homology between two sequences include, but are not limited to, GCG program package, Devereux, J., et al., *Nucleic Acids Research*, 12(1), 387 (1984)), BLASTP, BLASTN, and FASTA Altschul, S. F. et al., *J. Molec. Biol.*, 215, 403 (1990)).

The term "corresponding to" an amino acid position in a sequence means that when two sequences (e.g., polypeptide sequence) are aligned (e.g., using any of the known sequence alignment programs in the art such as the ones described herein), a certain amino acid residue in one sequence aligns with the an amino acid residue in the other sequence, these two amino acid residues are considered to be "corresponding to" each other. Thus, two amino acid residues that correspond to each other may not necessarily have the same numerical position. For example, catalytically essential glutamic acid (E) is located at position 117 of the amino acid identified by SEQ ID NO: 1 (*E. coli*), corresponding catalytically essential glutamic (E) is located at position 130 of the amino acid identified by SEQ ID NO: 3 (*T. maritima*), and catalytically essential glutamic acid (E) is located at position 110 of the amino acid identified by SEQ ID NO: 5 (*A. aeolicus*).

RNase III enzymes, homologs, fragments and variants may be recombinantly produced and purified. Methods of expressing and purifying RNase III are known. For example, a nucleic acid sequence encoding an RNase III enzyme may be cloned into expression vectors, for the expression of the RNase III protein in a variety of host cells, e.g., bacterial cells, insect cells, or mammalian cells.

Ribonucleic Acid

Affinity purification methods as provided herein are used, in some embodiments, to remove double-stranded RNA (dsRNA) from a preparation containing single-stranded RNA (ssRNA), such as in vitro transcribed mRNA. A "single-stranded RNA" is a polymeric strand of contiguous ribonucleotides. A "double-stranded RNA" is comprised of two polymeric strands of contiguous ribonucleotides bound to each other through complementary ribonucleotide base pairing. Single-stranded RNA includes, without limitation, mRNA, ribosomal RNA (see, e.g., Widmann et al., *Nucleic Acids Res.* 35 (10): 3339-54), transfer RNA (tRNA), tmRNA (see, e.g., Felden et al., *RNA*. 3 (1): 89-103), microRNA (miRNA), short-hairpin RNA (shRNA), and non-coding RNA (ncRNA). In some embodiments, a ssRNA is a messenger RNA (mRNA), such as a therapeutic mRNA. ssRNAs described herein may form intramolecular secondary structures and may be partially double-stranded. A RNA molecule that is partially double-stranded due to intramolecular structures may be considered a "partially double-stranded" or a "partially single-stranded" molecule.

Modified Ribonucleic Acid. RNA molecules of the present disclosure (e.g., therapeutic mRNA molecules), and nucleic acid (e.g., DNA) molecules encoding the RNA molecules, may include a chemical modification (are chemically modified). The terms "chemical modification" and "chemically modified" refer to modification with respect to adenosine (A), guanosine (G), uridine (U), thymidine (T) or cytidine (C) ribonucleosides or deoxyribnucleosides in at least one of their position, pattern, percent or population. Generally, these terms do not refer to the ribonucleotide modifications in naturally occurring 5'-terminal mRNA cap moieties (5' cap). With respect to a polypeptide, the term "modification" refers to a modification relative to the canonical set 20 amino acids. Polypeptides, as provided herein, are also considered "modified" of they contain amino acid substitutions, insertions or a combination of substitutions and insertions.

Polynucleotides (e.g., RNA polynucleotides, such as mRNA polynucleotides), in some embodiments, comprise various (more than one) different modifications. In some embodiments, a particular region of a polynucleotide contains one, two or more (optionally different) nucleoside or nucleotide modifications. In some embodiments, a modified RNA polynucleotide (e.g., a modified mRNA polynucleotide), introduced to a cell or organism, exhibits reduced degradation in the cell or organism, respectively, relative to an unmodified polynucleotide. In some embodiments, a modified RNA polynucleotide (e.g., a modified mRNA polynucleotide), introduced into a cell or organism, may exhibit reduced immunogenicity in the cell or organism, respectively (e.g., a reduced innate response).

Modifications of polynucleotides (e.g. RNA polynucleotides, such as mRNA polynucleotides) include, but are not limited to the following: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine, 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6, N6 (dimethyl)adenine; N6-cis-hydroxy-isopentenyl-adenosine; α-thio-adenosine; 2 (amino)adenine; 2 (aminopropyl)adenine; 2 (methylthio) N6 (isopentenyl)adenine; 2-(alkyl)adenine; 2-(aminoalkyl)adenine; 2-(aminopropyl)adenine; 2-(halo)adenine; 2-(halo)

adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyl adenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrole-cytidine; α-thio-cytidine; 2-(thio)cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl)cytosine; 5-(alkynyl)cytosine; 5-(halo)cytosine; 5-(propynyl) cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; T-Deoxy-T-b-thiomethoxycytidine TP; 2'-O-Methyl-5-(1-propynyl)cytidine TP; 3'-Ethynylcytidine TP; 4'-Azidocytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethyl guanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8 (alkynyl)guanine; 8 (halo)guanine; 8 (thioalkyl)guanine; 8-(alkenyl)guanine; 8-(alkyl)guanine; 8-(alkynyl)guanine; 8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deazaguanosine TP; N2-isobutyl-guanosine TP; 1-methylinosine; Inosine; 1,2'-O-dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl)pseudouridine; 1-methylpseduouridine; 1-methyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uridine; uridine 5-oxyacetic acid; uridine 5-oxyacetic acid methyl ester; 3-(3-Amino-3-carboxypropyl)-Uridine TP; 5-(iso-Pentenylaminomethyl)-2-thioutidine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylamino-carbonylethylenyl)-2 (thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonyiethylenyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio)pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl) pseudo-UTP; 1-Methyl-pseudo-UTP; 2 (thio)pseudouracil; 2' deoxy uridine; 2' fluorouridine; 2-(thio)uracil; 2,4-(dithio)pseudouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl)uracil; 4 (thio)pseudouracil; 4-(thio)pseudouracil; 4-(thio)uracil, 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio)uracil; 5 (methylaminomethyl)-4 (thio) uracil; 5 (propynyl)uracil; 5 (trifluoromethyl)uracil; 5-(2-aminopropyl)uracil; 5-(alkyl)-2-(thio)pseudouracil; 5-(alkyl)-2,4 (dithio)pseudouracil; 5-(alkyl)-4 (thio) pseudouracil; 5-(alkyl)pseudouracil; 5-(alkyl)uracil; 5-(alkynyl)uracil; 5-(allylamino)uracil; 5-(cyanoalkyl)uracil; 5-(dialkylaminoalkyl)uracil; 5-(dimethylaminoalkyl) uracil; 5-(guanidiniumalkyl)uracil; 5-(halo)uracil; 5-(1,3-diazole-1-alkyl)uracil; 5-(methoxy)uracil; 5-(methoxycarbonylmethyl)-2-(thio)uracil, 5-(methoxycarbonyl-methyl)uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio)uracil; 5-(methylaminomethyl)-2,4(dithio)uracil; 5-(methylaminomethyl)-4-(thio) uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; Pseudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±)1(2-Hydroxypropyl)pseudouridine TP; (2R)-1-(2-Hydroxypropyl)pseudouridine TP; (2S)-1-(2-Hydroxypropyl)pseudouridine TP; (E)-5-(2-Bromo-vinyl)ara-uridine TP; (E)-5-(2-Bromo-vinyl)uridine TP; (Z)-5-(2-Bromo-vinyl)ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethylbenzyl)pseudo-UTP; 1-(2,4,6-Trimethyl-phenyl)pseudo-UTP; 1-(2-Amino-2-carboxyethyl)pseudo-UTP; 1-(2-Amino-ethyl)pseudo-UTP; 1-(2-Hydroxyethyl) pseudouridine TP; 1-(2-Methoxyethyl)pseudouridine TP; 1-(3,4-Bis-trifluoromethoxybenzyl)pseudouridine TP; 1-(3,4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-Amino-4-carboxybutyl)pseudo-UTP; 1-(4-Amino-benzyl) pseudo-UTP; 1-(4-Amino-butyl)pseudo-UTP; 1-(4-Aminophenyl)pseudo-UTP; 1-(4-Azidobenzyl)pseudouridine TP; 1-(4-Bromobenzyl)pseudouridine TP; 1-(4-Chlorobenzyl) pseudouridine TP; 1-(4-Fluorobenzyl)pseudouridine TP; 1-(4-Iodobenzyl)pseudouridine TP; 1-(4-Methanesulfonylbenzyl)pseudouridine TP; 1-(4-Methoxybenzyl)pseudouridine TP; 1-(4-Methoxy-benzyl)pseudo-UTP; 1-(4-Methoxyphenyl)pseudo-UTP; 1-(4-Methylbenzyl)pseudouridine TP; 1-(4-Methyl-benzyl)pseudo-UTP; 1-(4-Nitrobenzyl) pseudouridine TP; 1-(4-Nitro-benzyl)pseudo-UTP; 1(4-Nitro-phenyl)pseudo-UTP; 1-(4-Thiomethoxybenzyl) pseudouridine TP; 1-(4-Trifluoromethoxybenzyl) pseudouridine TP; 1-(4-Trifluoromethylbenzyl) pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl} pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TT; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooetylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl) pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptoutidine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2 (2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}] propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine; 1-(aza)-2-(thio)-3-(aza)-phenoxazin-1-yl; 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'fluro-cytidine; 2' methyl, 2'amino, 2'azido, 2'fluro-adenine; 2'methyl, 2'amino, 2'azido, 2'fluro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-2-aminopyridopyrimidin-3-yl; 2-oxo-pyridopyrimidine-3-yl; 2-pyridinone; 3 nitropyrrole; 3-(methyl)-7-(propynyl) isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines; 5-(methyl)isocarbostyrityl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkythydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazin-1-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; O6-substituted purities; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of pseudouridine ($\psi$), N1-methylpseudouridine ($m^1\psi$), N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine. In some embodiments, polynucleotides (e.g., RNA polynucleotides, such as mRNA polynucleotides) include a combination of at least two (e.g., 2, 3, 4 or more) of the aforementioned modified nucleobases.

When the purified ssRNA RNA of the present disclosure is a purified mRNA, it may comprise any additional modifications known to one of skill in the art and as described in US Patent Publications US20120046346 and US20120251618, and PCT Publication WO 2012/019168. Other such components include, for example, a 5' cap, a polyA tail, a Kozak sequence; a 3' untranslated region (3' UTR); a 5' untranslated region (5' UTR); one or more intronic nucleotide sequences capable of being excised from the nucleic acid, or any combination thereof.

In some embodiments, the purified mRNAs of the present disclosure comprises a natural 5' cap. In some embodiments, a 5' cap may be a 5' cap analog, such as, e.g., a 5' diguanosine cap, tetraphosphate cap analogs having a methylene-bis (phosphonate) moiety, cap analogs having a sulfur substitution for a non-bridging oxygen, N7-benzylated dinucleoside tetraphosphate analogs, or anti-reverse cap analogs. In some embodiments, the 5' cap is 7mG(5')ppp(5')NlmpNp. In some embodiments, the 5'cap analog is a 5'diguanosine cap. In some embodiments, the synthetic, modified mRNA of the present disclosure does not comprise a 5' triphosphate.

Both the 5'UTR and the 3'UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing. The 3'-poly(A) tail is typically a stretch of adenine nucleotides added to the 3'-end of the transcribed mRNA. In some embodiments the length of the 3'-poly(A) tail may be an essential element with respect to the stability of the individual mRNA. A poly-A tail may be greater than 30 nucleotides in length, greater than 35 nucleotides in length, at least 40 nucleotides, at least 45 nucleotides, at least 55 nucleotides, at least 60 nucleotide, at least 70 nucleotides, at least 80 nucleotides, at least 90 nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900 nucleotides, at least 1000 nucleotides, or more.

In some embodiments, the purified mRNA of the present disclosure encodes a protein. In some embodiments, the protein is an antigen, e.g., a viral antigen. In some embodiments, the modified mRNA purified using the methods described herein may be used as a mRNA vaccine.

Methods

Method of purifying a nucleic acid (e.g., mRNA) preparation of the present disclosure generally include contacting the nucleic acid preparation with an RNase III enzyme that is immobilized on a solid support.

An affinity purification method may, in some embodiments, include the following steps: (1) incubating a nucleic acid preparation (e.g., a solution containing in vitro-transcribed mRNA) with a solid support to which a RNase III enzyme (e.g., a thermostable RNase III enzyme) or variant thereof (e.g., a catalytically active RNase III) is immobilized under conditions that result in binding of double-stranded RNA (dsRNA) to the immobilized RNase III enzyme; (2) eluting unbound preparation components from the support using appropriate buffers that maintain the binding interaction between the RNase III enzyme and the dsRNA to produce a preparation enriched for single-stranded RNA (ssRNA) (a "ssRNA-enriched preparation"); and (3) optionally performing at least one additional purification process to isolate a ssRNA (e.g., mRNA) from the preparation.

Methods may be performed "under conditions that result in binding of the RNase III enzyme to double-stranded RNA." These conditions are readily determined by a skilled artisan and include, for example, temperature conditions, buffer (e.g., salt and pH) conditions, and reaction/process time.

In some embodiments, an affinity purification method as provided herein is performed using a RNase III enzyme (e.g., identified by SEQ ID NO: 1, 2, 5 or 6) that is optimally active at a temperature of 20° C.-42° C. Thus, in some embodiments, an affinity purification method is performed at 20° C.-42° C. For example, an affinity purification method may be performed at 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C. 42° C., or within a range having endpoints defined by any two of the foregoing temperatures.

In some embodiments, an affinity purification method as provided herein is performed using a RNase III enzyme (e.g., identified by SEQ ID NO: 3 or 4) that is optimally active at a temperature of 40° C.-70° C. Thus, in some embodiments, an affinity purification method is performed at 40° C.-70° C. For example, an affinity purification method may be performed at 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., or within a range having endpoints defined by any two of the foregoing temperatures. In some embodiments, an affinity purification method is performed at a temperature greater than 70° C. For example, an affinity purification method may be performed at 75° C., 80° C., 85° C., 90° C., or 95° C.

Incubation (contact) times may vary. In some embodiments, a nucleic acid preparation (e.g., an IVT preparation) is contacted with RNase III enzyme immobilized on a solid support for 5 minutes to 3 hours, or longer. For example, a nucleic acid preparation may be contacted with RNase III enzyme immobilized on a solid support for 5 minutes, 10 minutes, 15 minutes, 20 minutes, 30 minutes, 45 minutes, 1 hour, 2 hours, 3 hours, or longer.

In some embodiments, affinity purification methods further comprise separating solid phase RNase III-dsRNA complexes from the liquid phase ssRNA-enriched preparation. This separation step(s) depends on the type of solid support used in an affinity purification method. For example, for RNase III immobilized on a resin, the ssRNA-enriched preparation may be separated by centrifugation. For RNase III immobilized on magnetic beads, a magnet may be used to remove the beads from the ssRNA-enriched preparation. Separation of the solid phase from the liquid phase yields ssRNA that is substantially free of dsRNA contaminants. Following or preceding performance of an affinity purification method using a RNase III enzyme (or variant thereof), the nucleic acid preparation may be subjected to one or more additional purification methods to remove DNA and/or protein contaminants. Methods of removing DNA or protein contaminants from a preparation containing RNA are known. The order in which the different purification methods are performed may be varied.

Compositions

The present disclosure also encompasses compositions comprising ssRNA (e.g., mRNA) prepared, for example, via IVT and purified according to the affinity purification methods as provided herein. In some embodiments, the compositions are therapeutic composition. For example, the RNA (e.g., mRNA) purified using the methods of the present disclosure may be used in a vaccine composition to treat or prevent cancer or an infectious disease.

In some embodiments, a composition comprises a RNA (e.g., mRNA) purified by a method of the present disclosure having an open reading frame comprising at least one chemical modification or optionally no nucleotide modification, a 5′ terminal cap that is 7mG(5′)ppp(5′)NlmpNp, and a polyA tail. In some embodiments, 100% of the uracil in the open reading frame have a chemical modification. In some embodiments, a chemical modification is in the 5-position of the uracil. In some embodiments, a chemical modification is a N1-methyl pseudouridine. In some embodiments, 100% of the uracil in the open reading frame have a N1-methyl pseudouridine in the 5-position of the uracil.

In some embodiments, the RNA (e.g., mRNA) purified using the methods of the present disclosure may be formulated in a nanoparticle, such as a lipid particle described, for example, in any one of International Application No. PCT/US16/58327, International Application No. PCT/US16/583140, and International Application No. PCT/US16/58324, each of which was filed Oct. 21, 2016 and is herein incorporated by reference. In some embodiments, the nanoparticle has a mean diameter of 50-200 nm. In some embodiments, the nanoparticle is a lipid nanoparticle. In some embodiments, the lipid nanoparticle comprises a cationic lipid, a PEG-modified lipid, a sterol and a non-cationic lipid. In some embodiments, the lipid nanoparticle comprises a molar ratio of about 20-60% cationic lipid, 0.5-15% PEG-modified lipid, 25-55% sterol, and 25% non-cationic lipid. In some embodiments, a lipid nanoparticle comprises a cationic lipid, a PEG-modified lipid, a sterol and a non-cationic lipid. In some embodiments, a cationic lipid is an ionizable cationic lipid and the non-cationic lipid is a neutral lipid, and the sterol is a cholesterol. In some embodiments, a cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate (L319), (12Z,15Z)—N,N-dimethyl-2-nonylhenicosa-12,15-dien-1-amine (L608), and N,N-dimethyl-1-[(1S,2R)-2-octylcyclopropyl]heptadecan-8-amine (L530).

In some embodiments, a lipid nanoparticle comprises compounds of Formula (I) and/or Formula (II) and encapsulates a RNA (e.g., mRNA) purified using the methods of the present disclosure.

In some embodiments, a nanoparticle comprises compounds of Formula (I):

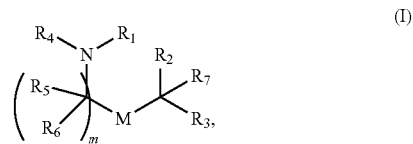

or a salt or isomer thereof, wherein:

$R_1$ is selected from the group consisting of $C_{5-30}$ alkyl, $C_{5-20}$ alkenyl, —R*YR″, —YR″, and —R″M′R′;

$R_2$ and $R_3$ are independently selected from the group consisting of H, $C_{1-14}$ alkyl, $C_{2-14}$ alkenyl, —R*YR″, —YR″, and —R*OR″, or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M′ are independently selected from —C(O)O—, —OC(O)—, —C(O)N(R′)—, —N(R′)C(O)—, —C(O)—, —C(S)—, —C(S)S—, —SC(S)—, —CH(OH)—, —P(O)(OR′)O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R′ is independently selected from the group consisting of $C_{1-18}$ alkyl, $C_{2-18}$ alkenyl, —R*YR″, —YR″, and H;

each R″ is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;
each X is independently selected from the group consisting of F, Cl, Br, and I; and
m is selected from 5, 6, 7, 8, 9, 10, 11, 12, and 13.

In some embodiments, a subset of compounds of Formula (I) includes those in which when $R_4$ is —$(CH_2)_nQ$, —$(CH_2)CHQR$, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)CHQR$, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_4$)N(R)$_2$, and each n is independently selected from 1, 2, 3, 4, and 5; and when Q is a 5- to 14-membered heterocycle and (i) $R_4$ is —$(CH_2)_nQ$ in which n is 1 or 2, or (ii) $R_4$ is —$(CH_2)_nCHQR$ in which n is 1, or (iii) $R_4$ is —CHQR, and —$CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)CHQR$, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{3-6}$ carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which R$_1$ is selected from the group consisting of C$_{5-30}$ alkyl, C$_{5-20}$ alkenyl, —R*YR", —YR", and —R"M'R';

R$_2$ and R$_3$ are independently selected from the group consisting of H, C$_{2-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is —(CH$_2$)Q or —(CH$_2$)$_n$CHQR, where Q is —N(R)$_2$, and n is selected from 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which R$_1$ is selected from the group consisting of C$_{5-30}$ alkyl, C$_{5-20}$ alkenyl, —R*YR", —YR", and —R"M'R';

R$_2$ and R$_3$ are independently selected from the group consisting of C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of —(CH$_2$)$_n$Q, —(CH$_2$)$_n$CHQR, —CHQR, and —CQ(R)$_2$, where Q is —N(R)$_2$, and n is selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{1-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

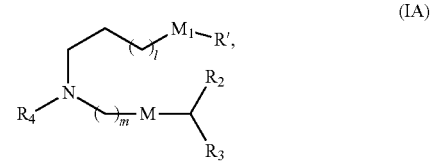

(IA)

or a salt or isomer thereof, wherein l is selected from 1, 2, 3, 4, and 5; m is selected from 5, 6, 7, 8, and 9; M$_1$ is a bond or M'; R$_4$ is unsubstituted C$_{1-3}$ alkyl, or —(CH$_2$)$_n$Q, in which Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and R$_2$ and R$_3$ are independently selected from the group consisting of H, C$_{1-14}$ alkyl, and C$_{2-14}$ alkenyl.

In some embodiments, a subset of compounds of Formula (I) includes those of Formula (II).

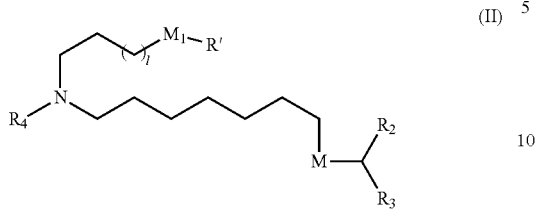

or a salt or isomer thereof, wherein l is selected from 1, 2, 3, 4, and 5; $M_1$ is a bond or M'; $R_4$ is unsubstituted $C_{1-3}$ alkyl, or $-(CH_2)_nQ$, in which n is 2, 3, or 4, and Q is OH, $-NHC(S)N(R)_2$, $-NHC(O)N(R)_2$, $-N(R)C(O)R$, $-N(R)S(O)_2R$, $-N(R)R_8$, $-NHC(=NR_9)N(R)_2$, $-NHC(=CHR_9)N(R)_2$, $-OC(O)N(R)_2$, $-N(R)C(O)OR$, heteroaryl or heterocycloalkyl; M and M' are independently selected from $-C(O)O-$, $-OC(O)-$, $-C(O)N(R')-$, $-P(O)(OR')O-$, $-S-S-$, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IIa), (IIb), (IIc), or (IIe):

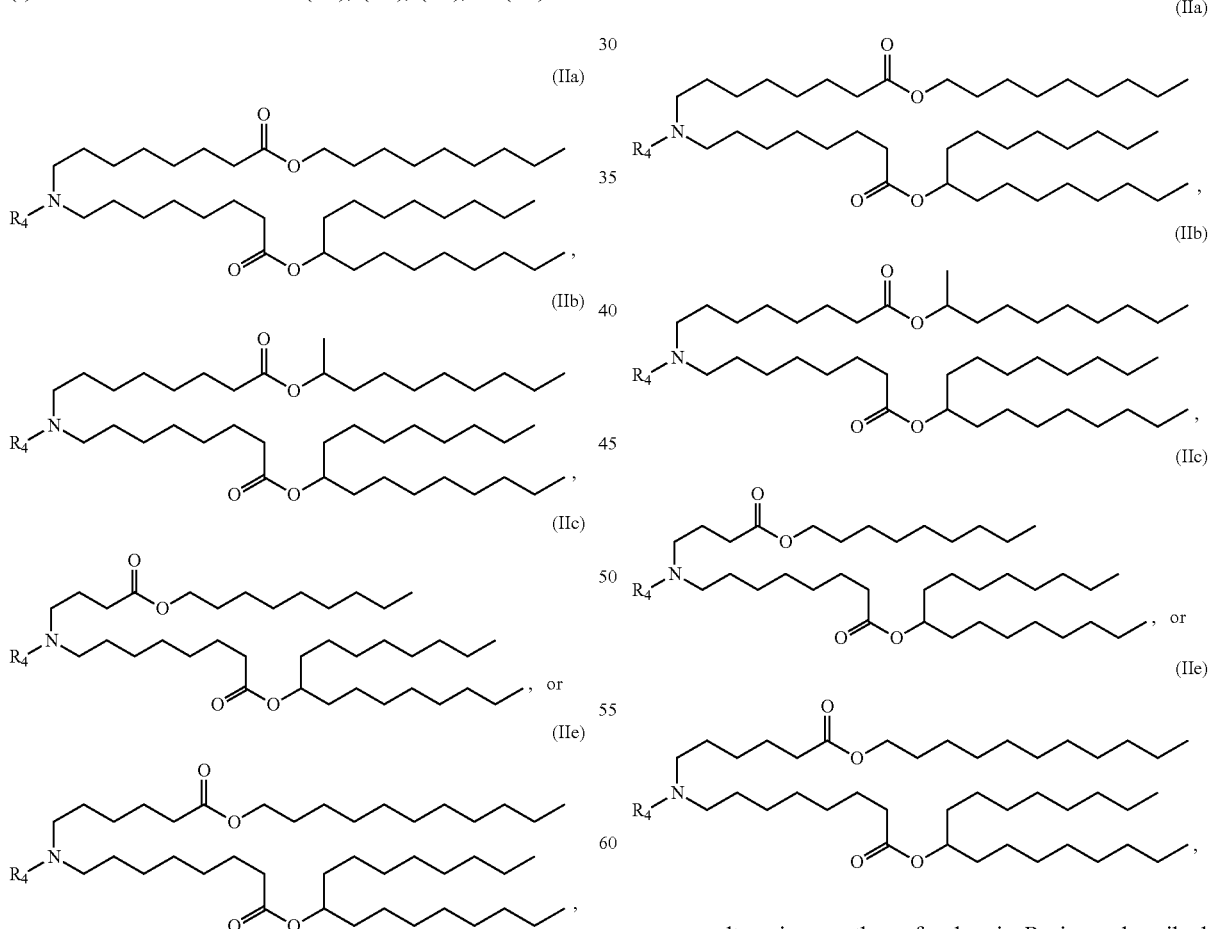

or a salt or isomer thereof, wherein $R_4$ is as described herein.

In some embodiments, a subset of compounds of Formula (I) includes of Formula (IId):

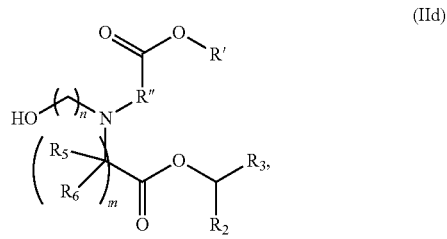

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, a subset of compounds of Formula (I) includes those of Formula (IIa), (IIb), (IIc), or (IIe):

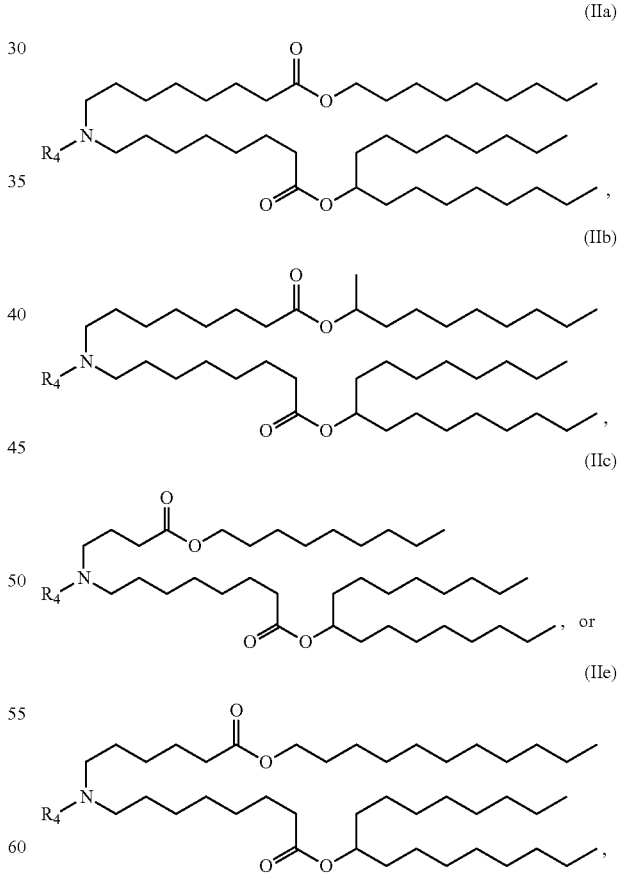

or a salt or isomer thereof, wherein $R_4$ is as described herein.

In some embodiments, a subset of compounds of Formula (I) includes those of Formula (IId):

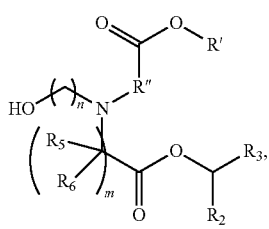
(IId)

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, the compound of Formula (I) is selected from e group consisting of:

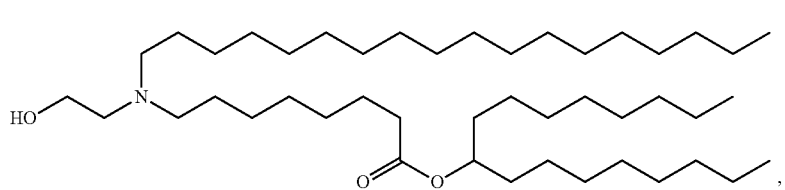
(Compound 1)

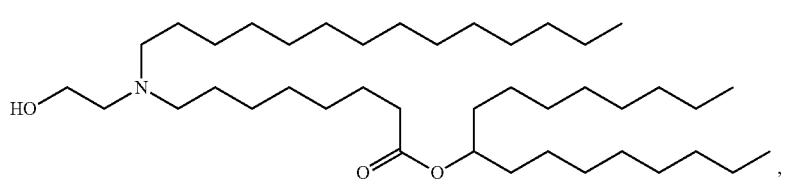
(Compound 2)

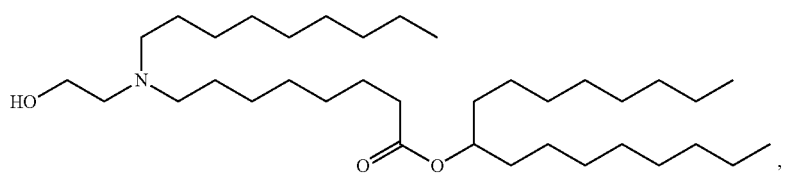
(Compound 3)

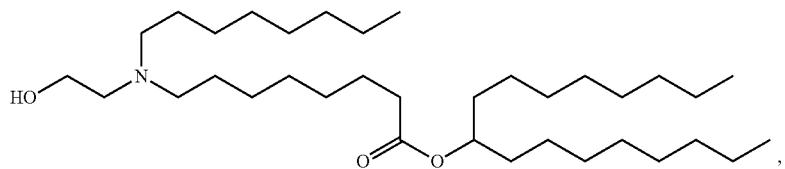
(Compound 4)

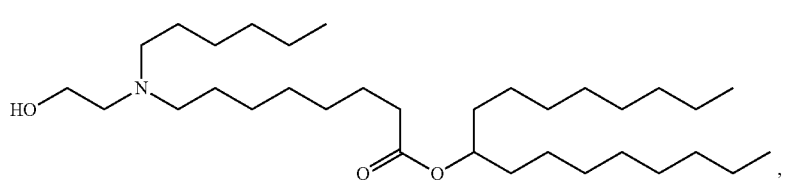
(Compound 5)

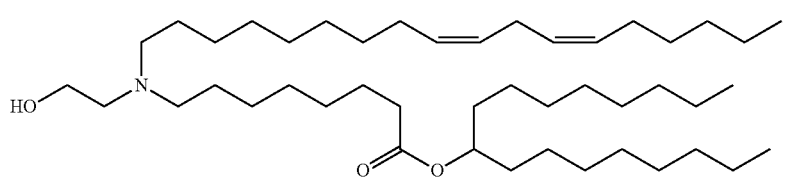
(Compound 6)

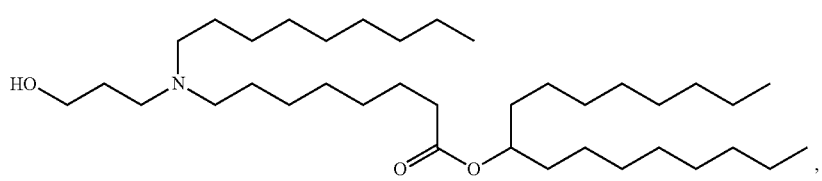
(Compound 7)

-continued
(Compound 8)
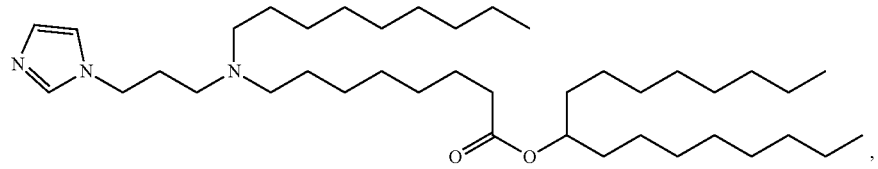,
(Compound 9)
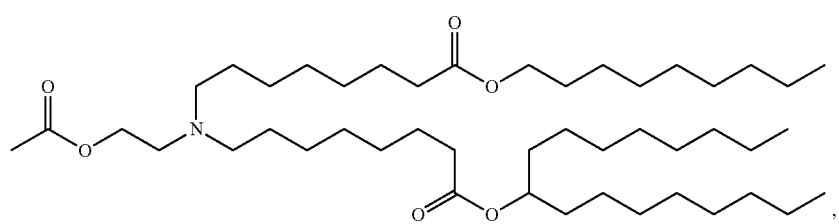,
(Compound 10)
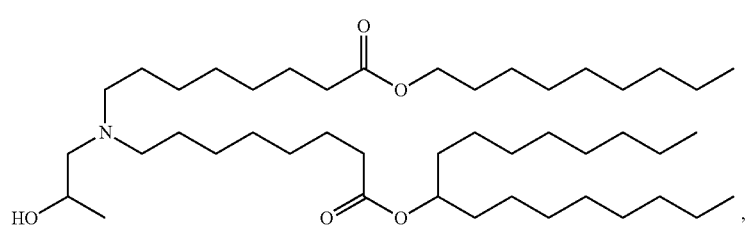,
(Compound 11)
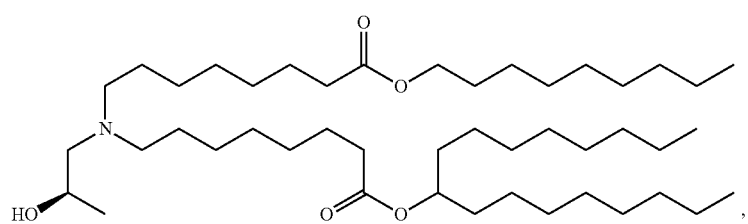,
(Compound 12)
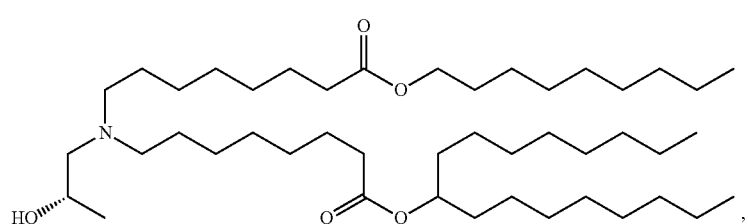,
(Compound 13)
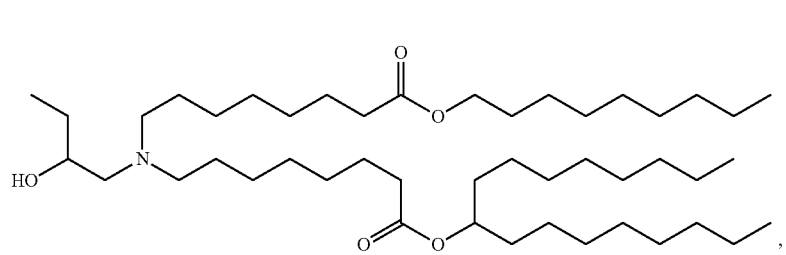,
(Compound 14)
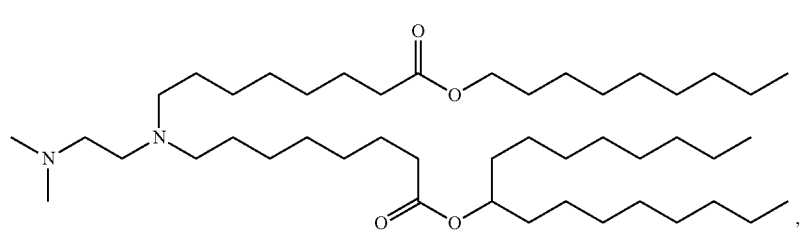, (Compound 15)
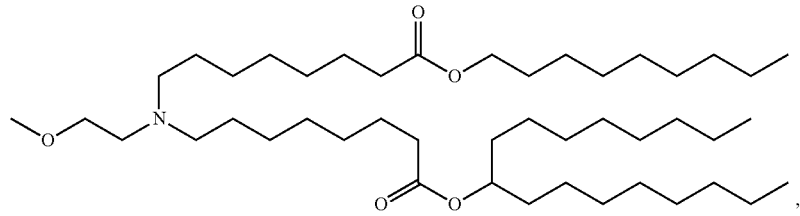
(Compound 16)
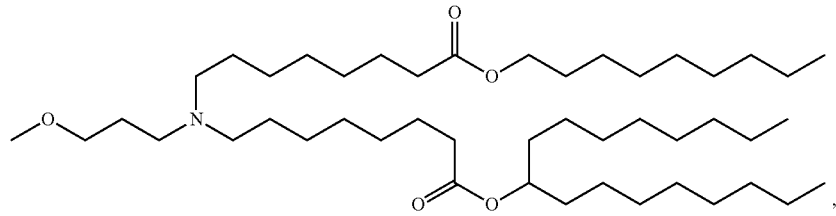
(Compound 17)
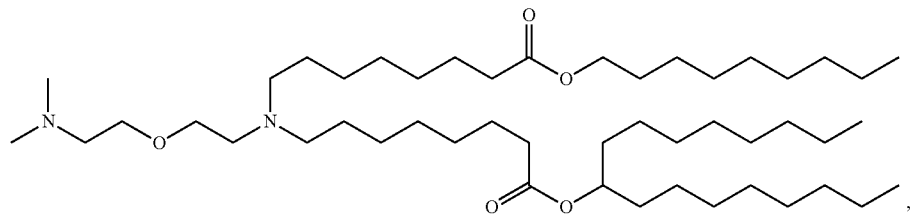
(Compound 18)
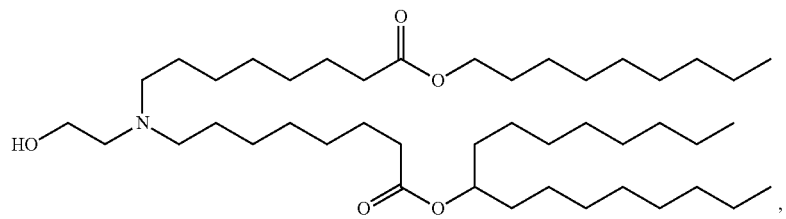
(Compound 19)
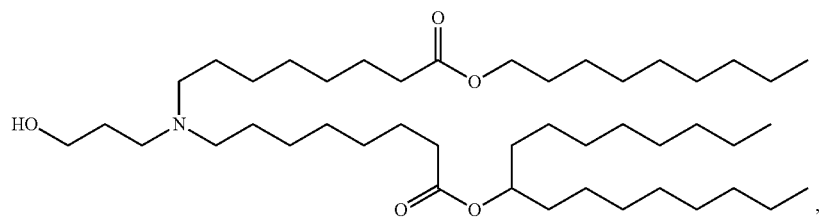
(Compound 20)
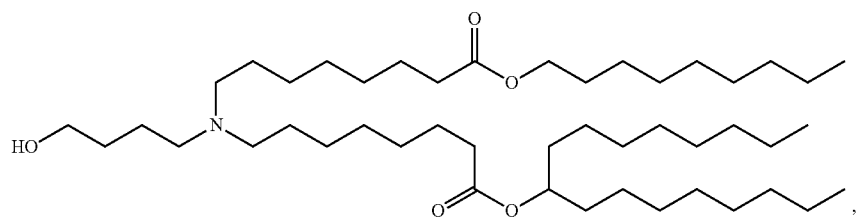
(Compound 21)
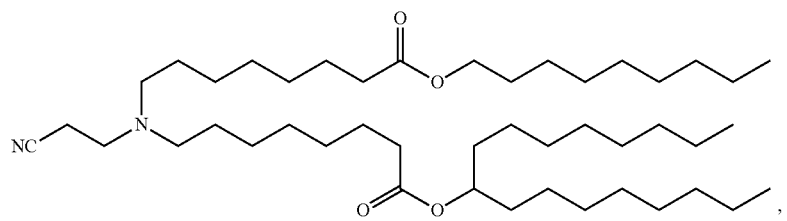

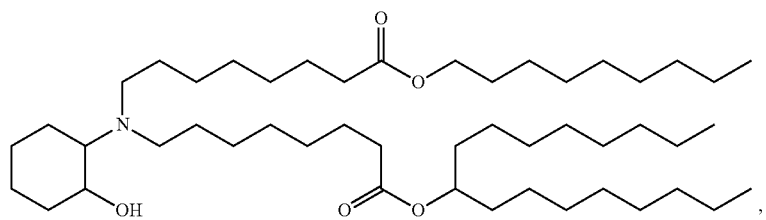
(Compound 22)
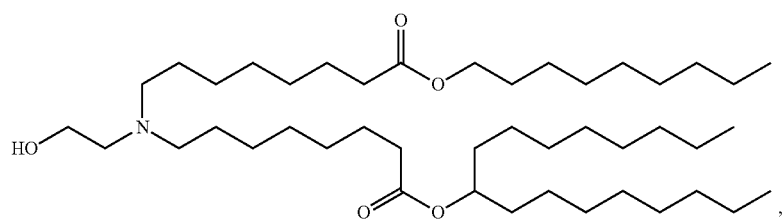
(Compound 23)
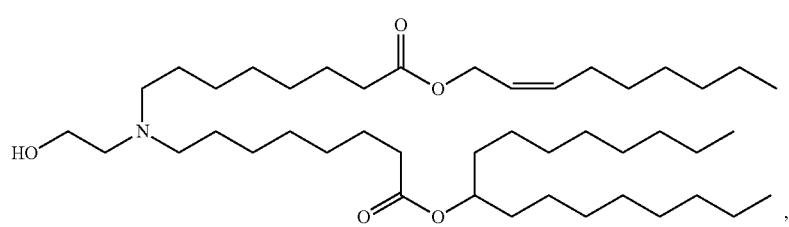
(Compound 24)
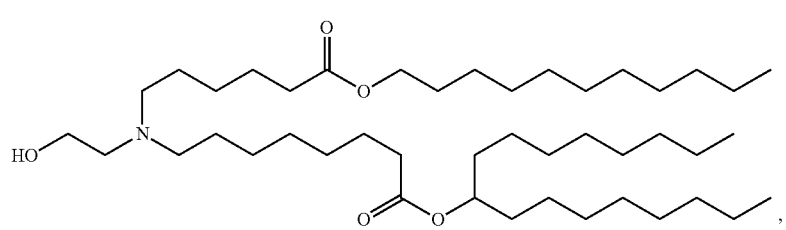
(Compound 25)
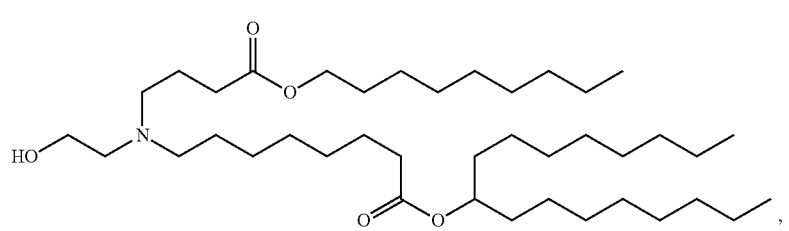
(Compound 26)
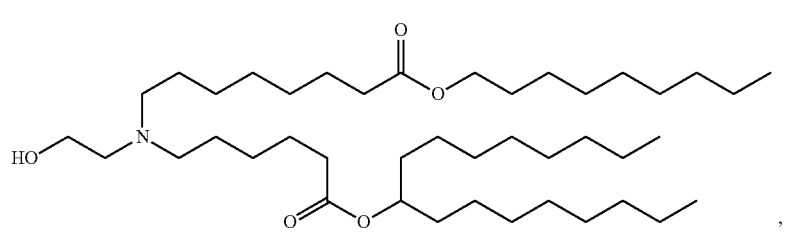
(Compound 27)
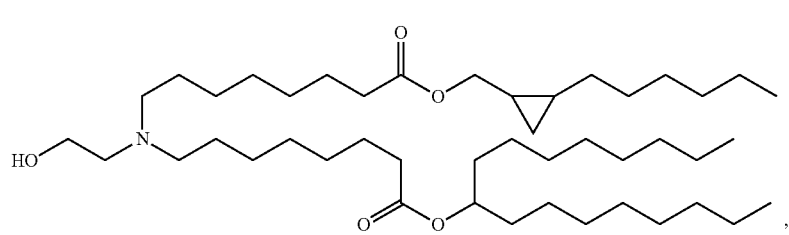
(Compound 28)

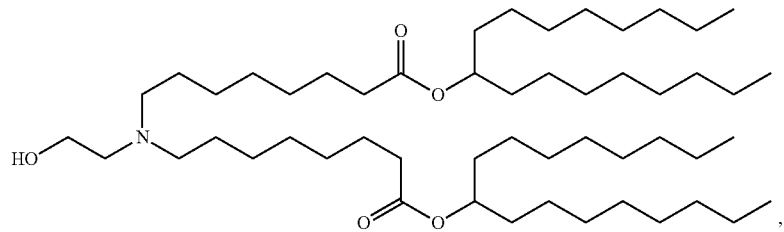
(Compound 29)
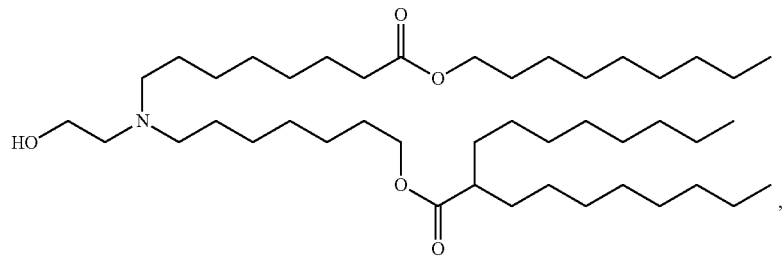
(Compound 30)
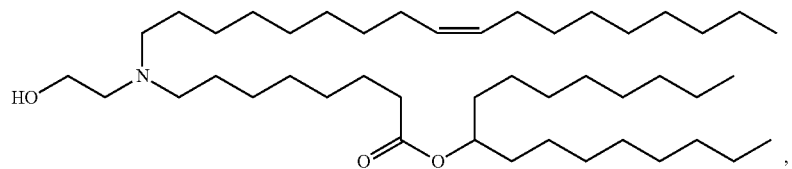
(Compound 31)
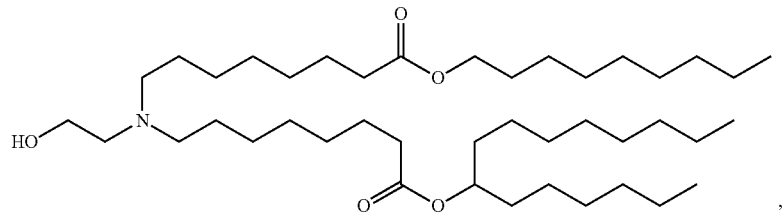
(Compound 32)
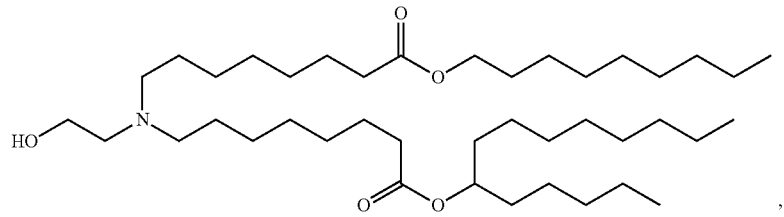
(Compound 33)
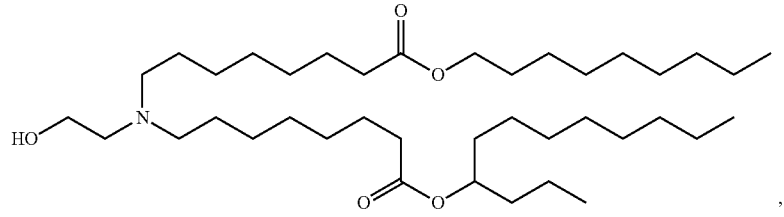
(Compound 34)
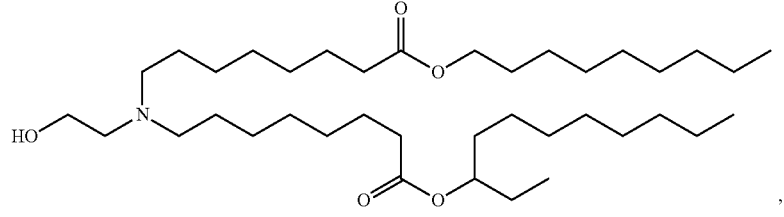
(Compound 35)

-continued
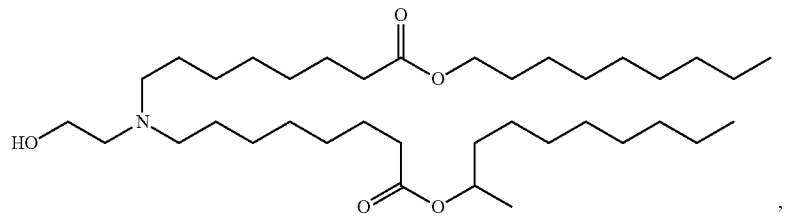
(Compound 36)
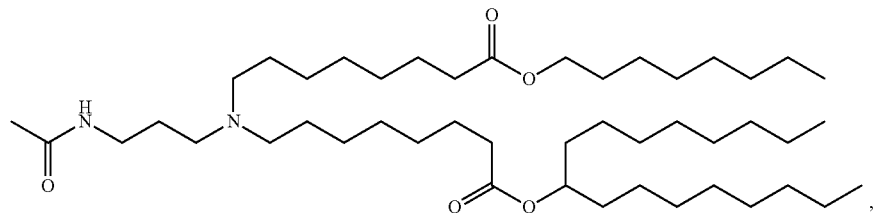
(Compound 37)
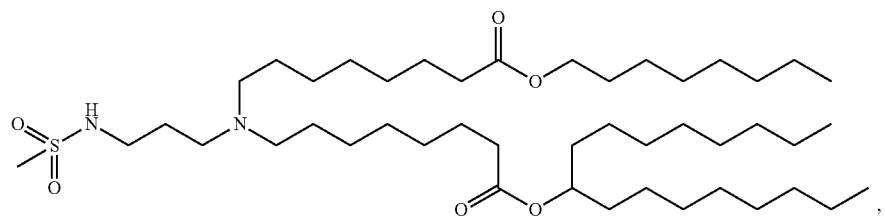
(Compound 38)
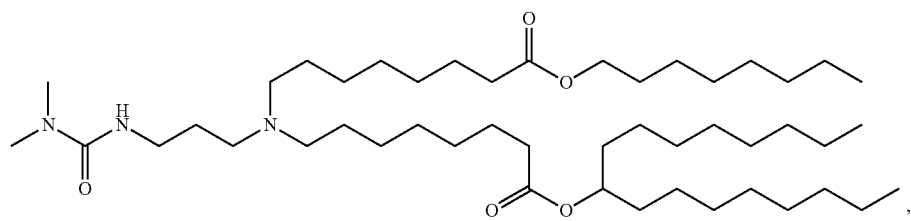
(Compound 39)
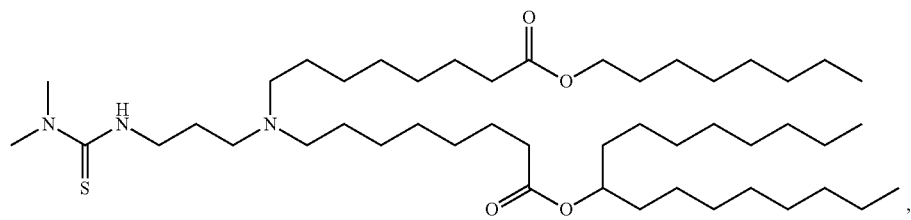
(Compound 40)
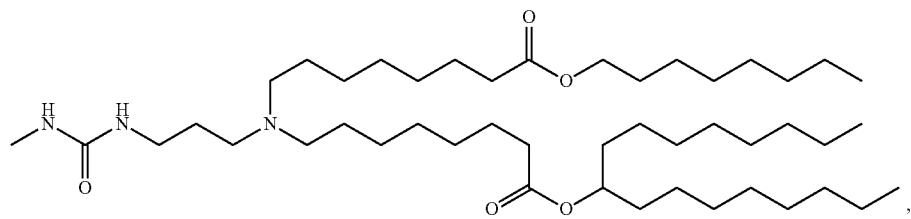
(Compound 41)
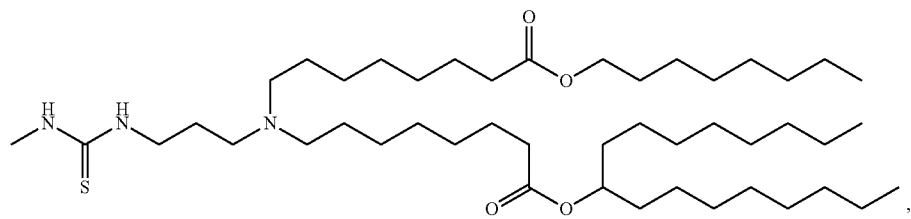
(Compound 42)

-continued
(Compound 43)
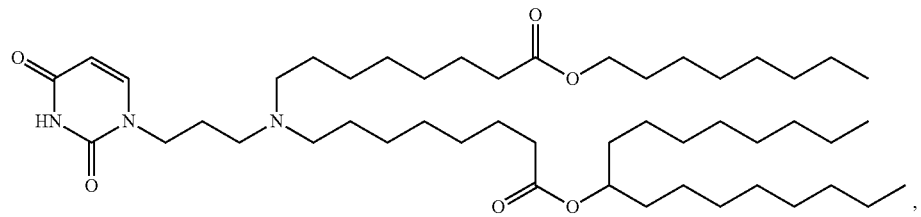
(Compound 44)
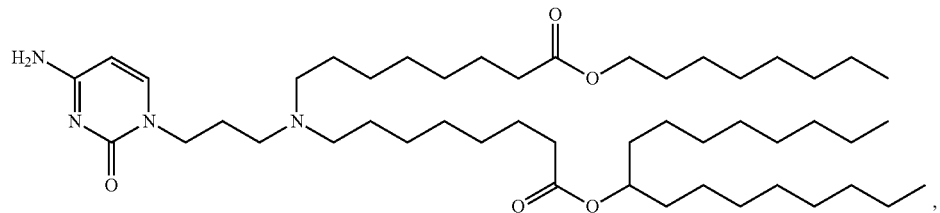
(Compound 45)
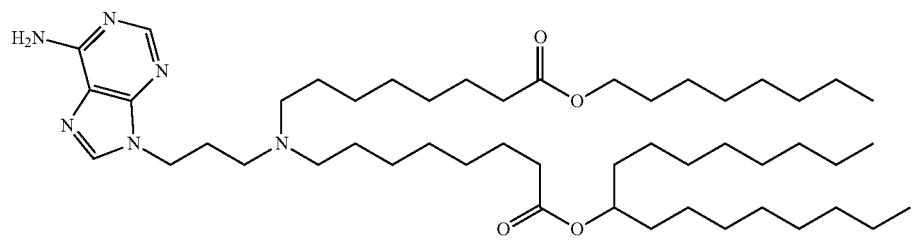
(Compound 46)
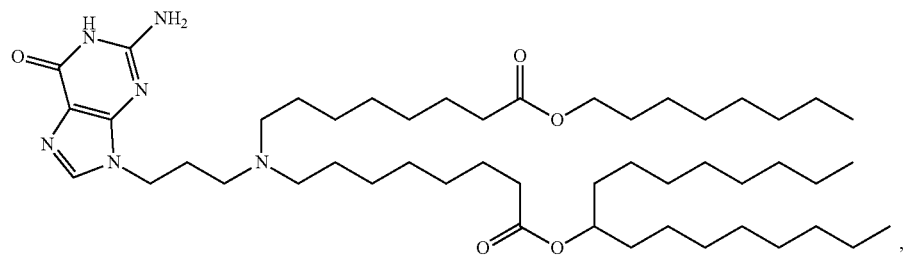
(Compound 47)
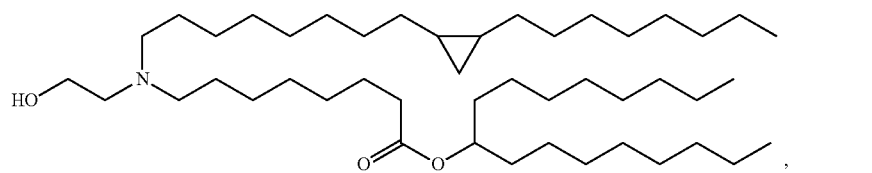
(Compound 48)
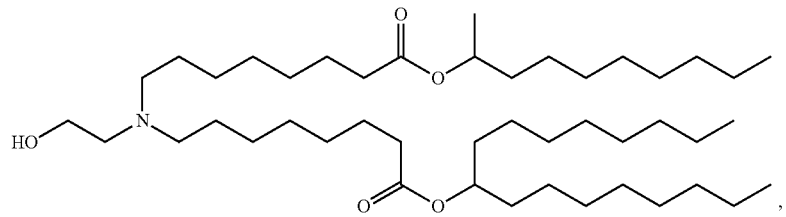
(Compound 49)
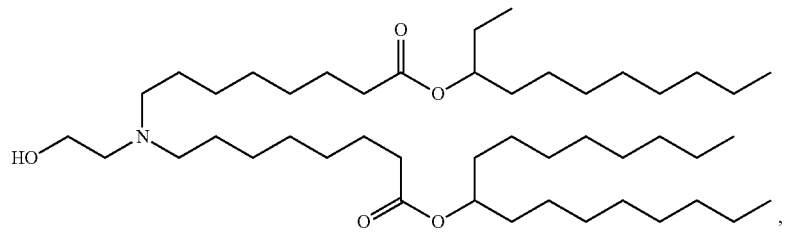

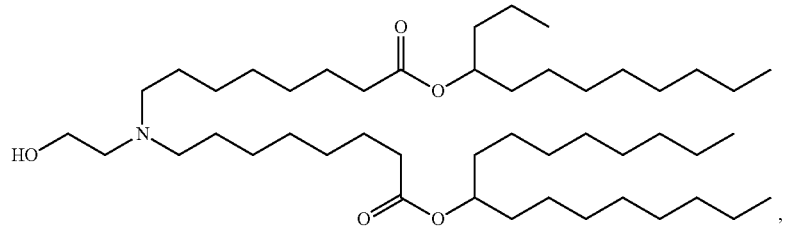
(Compound 50)
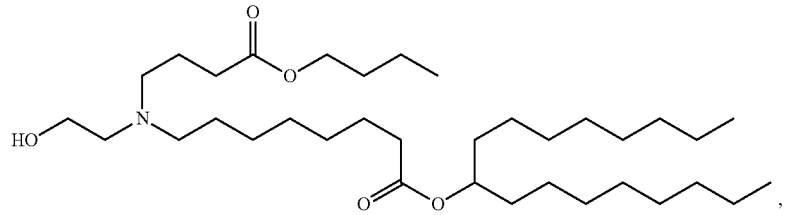
(Compound 51)
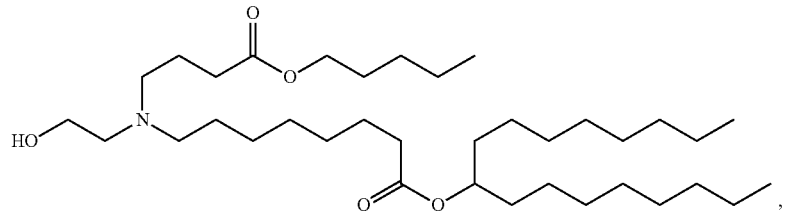
(Compound 52)
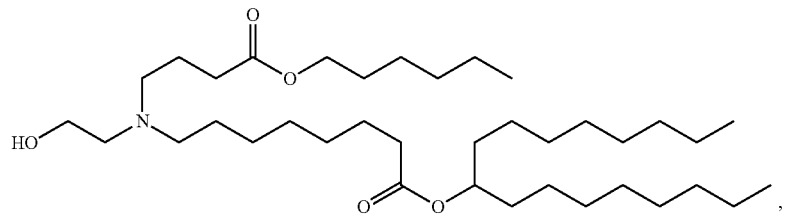
(Compound 53)
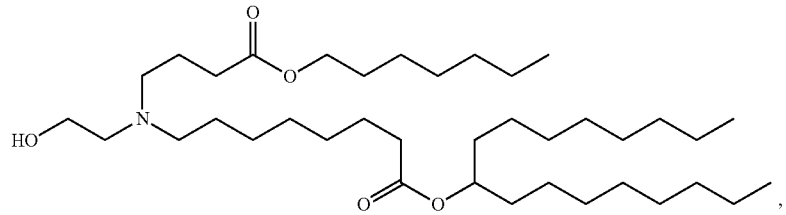
(Compound 54)
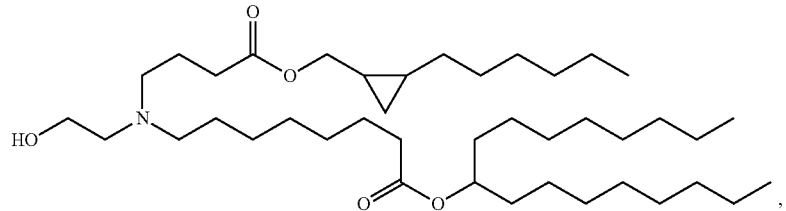
(Compound 55)
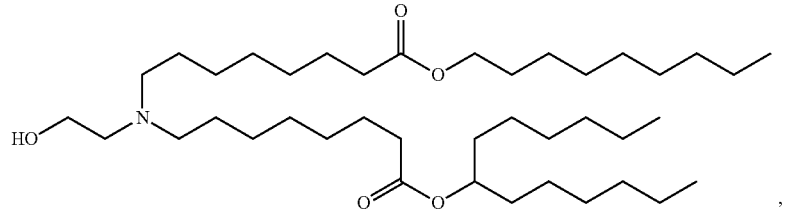
(Compound 56)

-continued
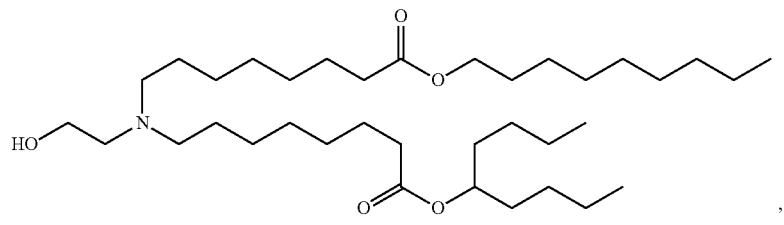
(Compound 57)
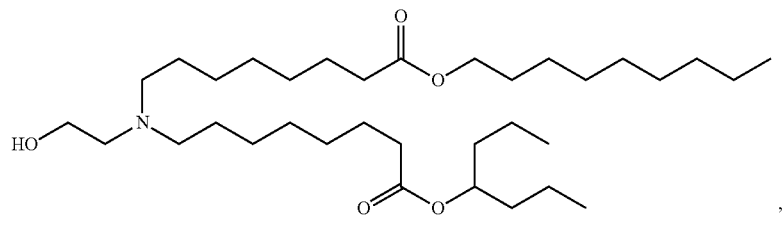
(Compound 58)
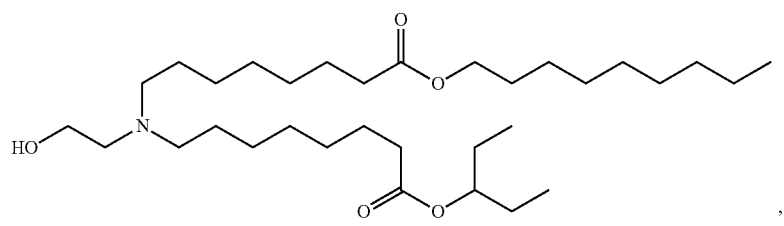
(Compound 59)
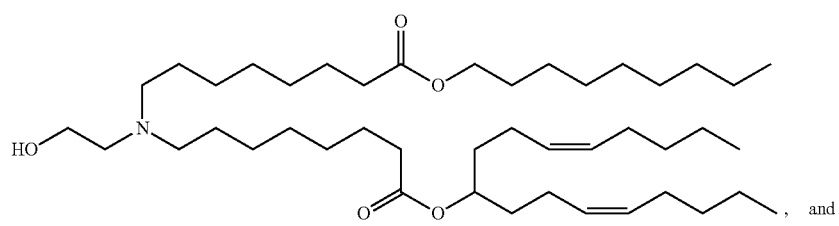
(Compound 60)
, and
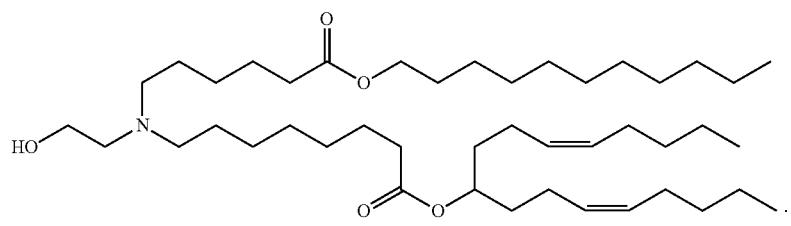
(Compound 61)
.
In further embodiments, the compound of Formula (I) is selected from the group consisting of:
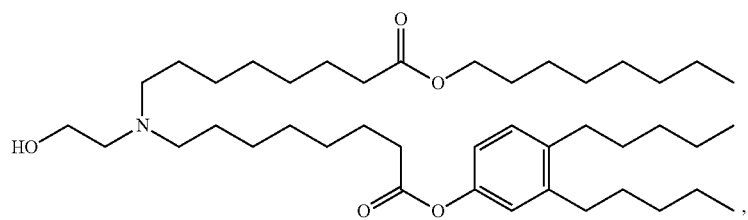
(Compound 62)
, (Compound 63)
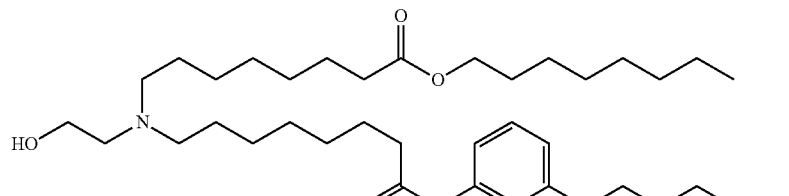
, and
(Compound 64)
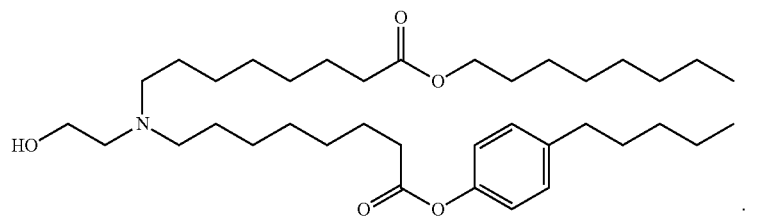
.
In some embodiments, the compound of Formula (I) is selected from the group consisting of:
(Compound 65)
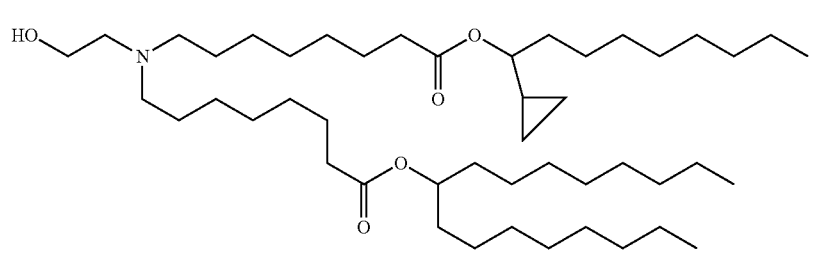
,
(Compound 66)
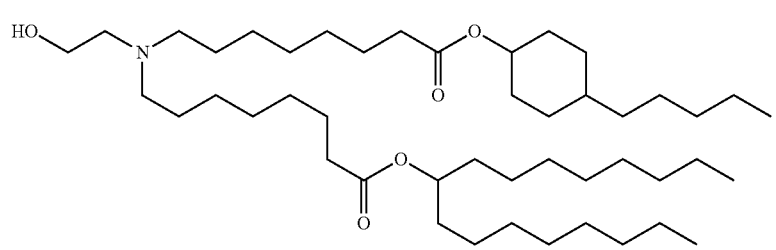
,
(Compound 67)
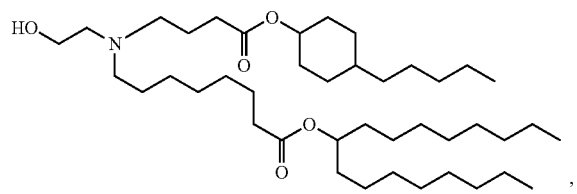
,
(Compound 68)
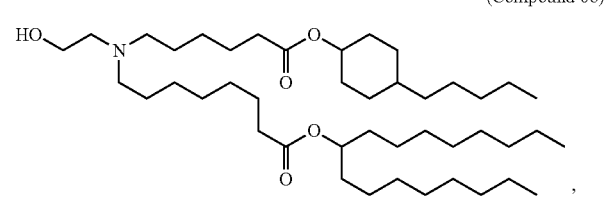
,
(Compound 69)
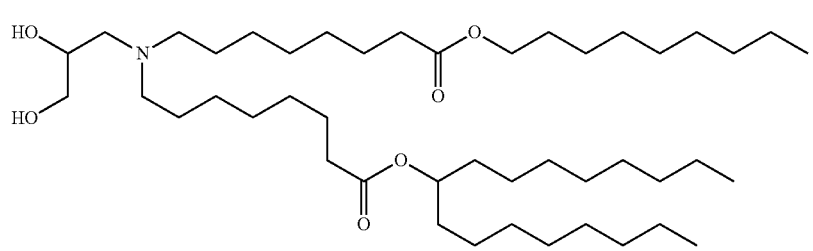
, (Compound 70)
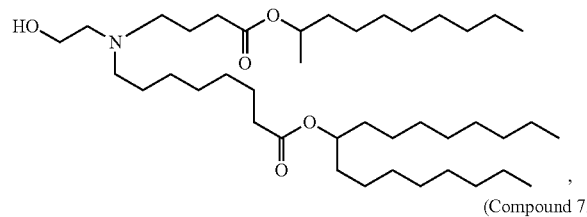
(Compound 71)
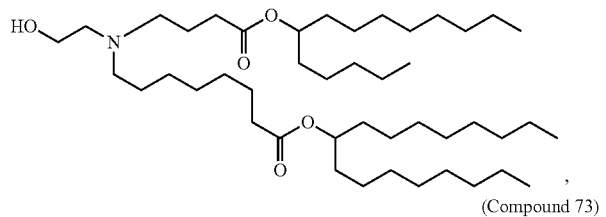
(Compound 72)
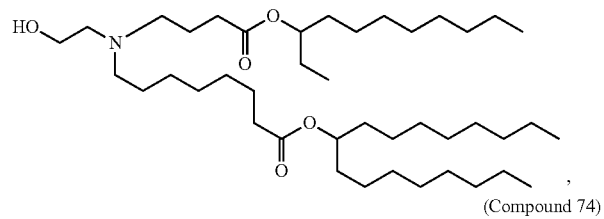
(Compound 73)
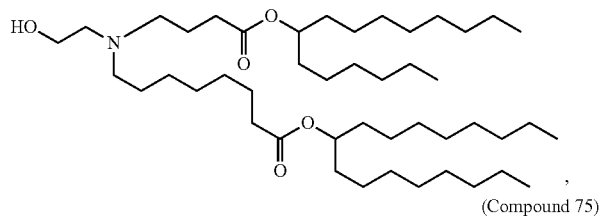
(Compound 74)
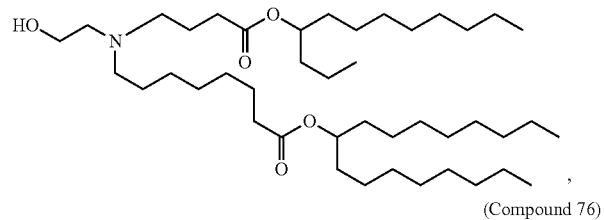
(Compound 75)
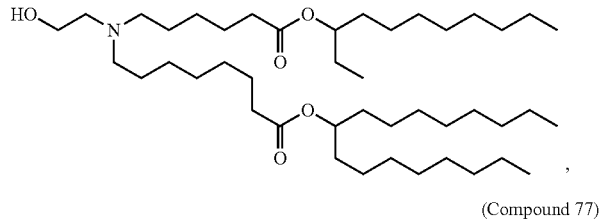
(Compound 76)
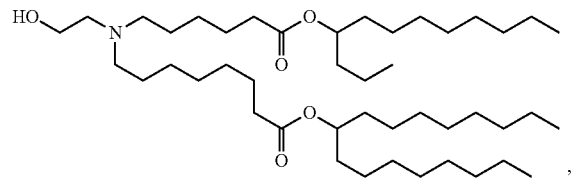
(Compound 77)
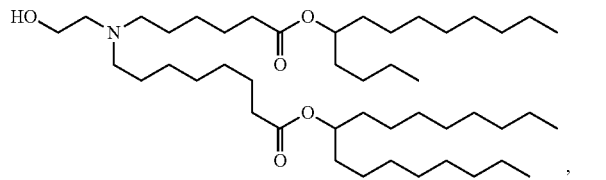
(Compound 78)
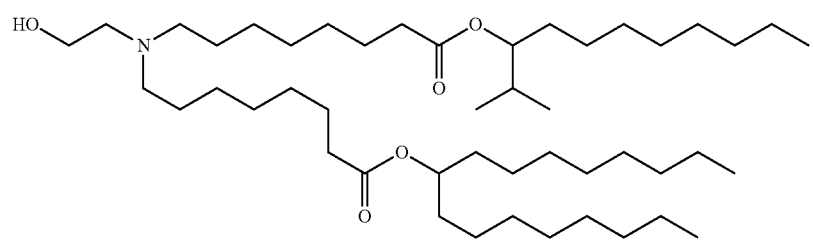
(Compound 79)
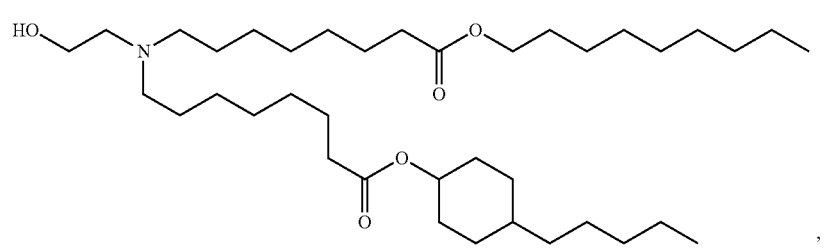
(Compound 80)
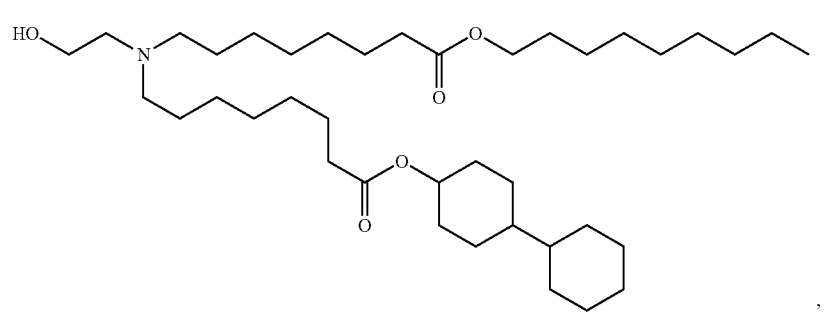

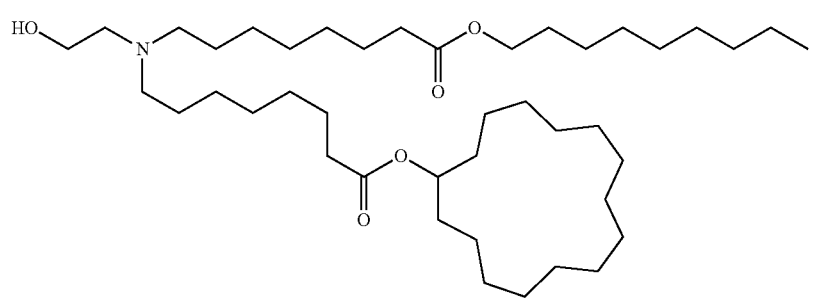
(Compound 81)
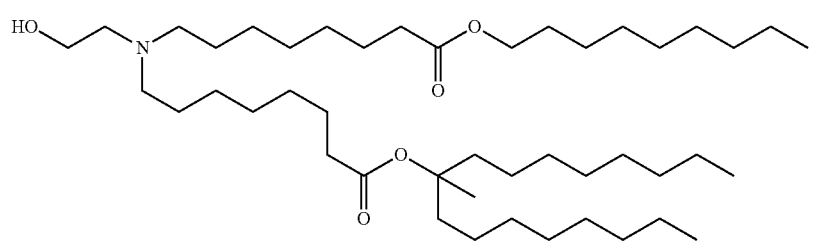
(Compound 82)
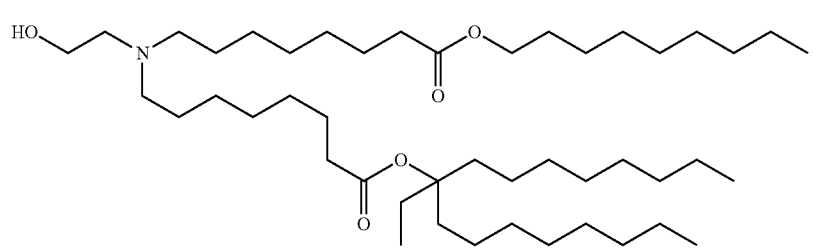
(Compound 83)
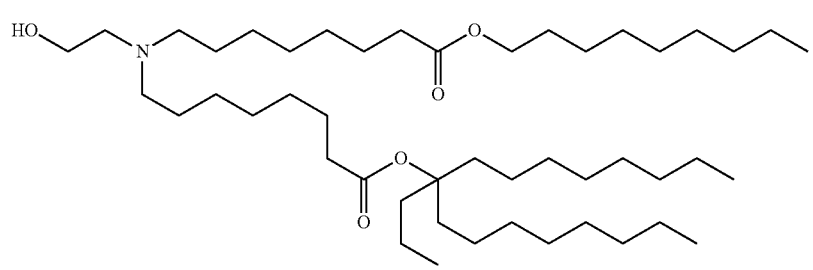
(Compound 84)
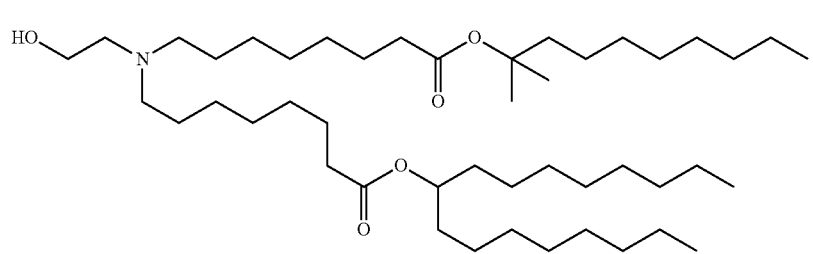
(Compound 85)
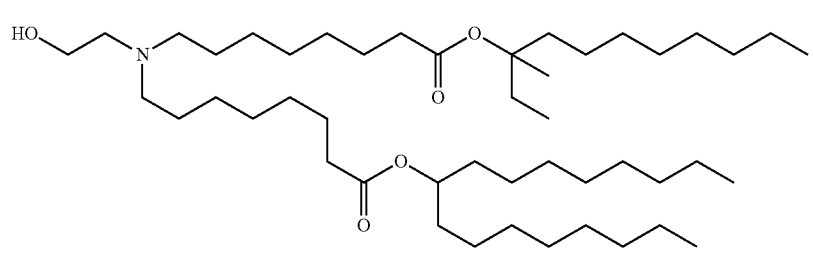
(Compound 86)

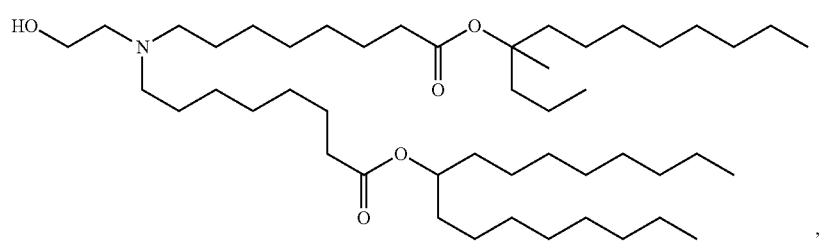
(Compound 87)
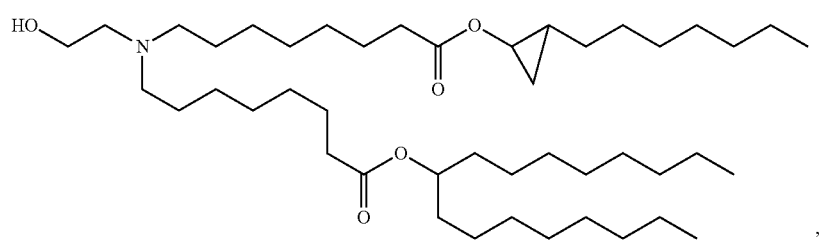
(Compound 88)
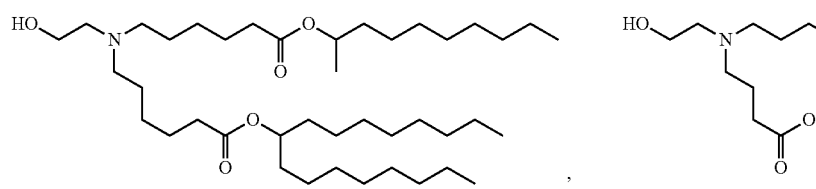
(Compound 89)
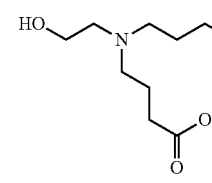
(Compound 90)
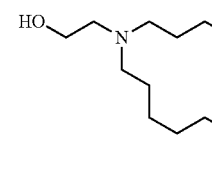
(Compound 91)
(Compound 92)
(Compound 93)
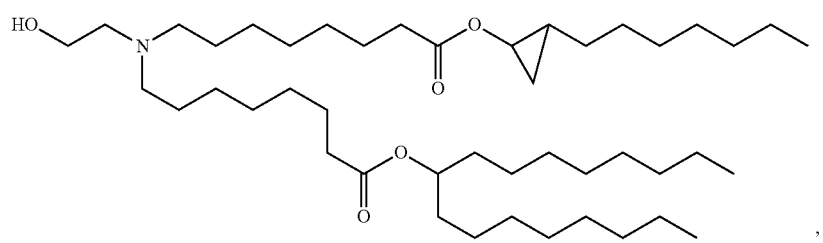
(Compound 94)
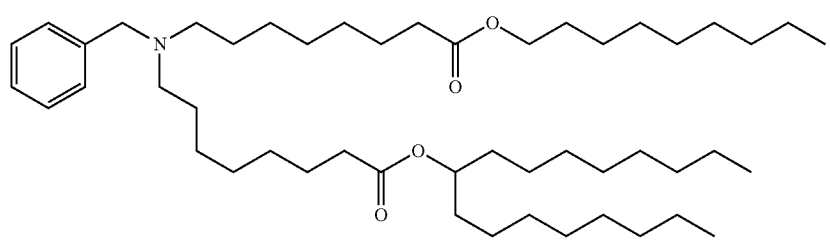
(Compound 95)

-continued
(Compound 96)
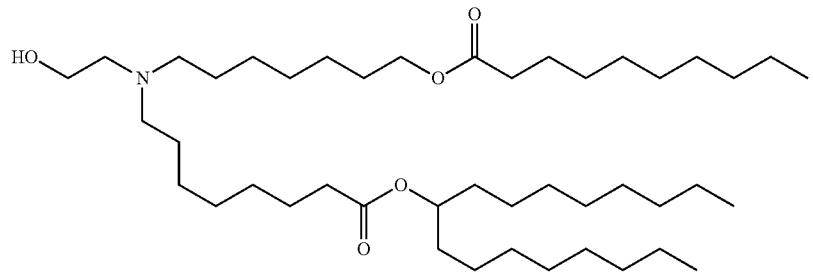
(Compound 97)
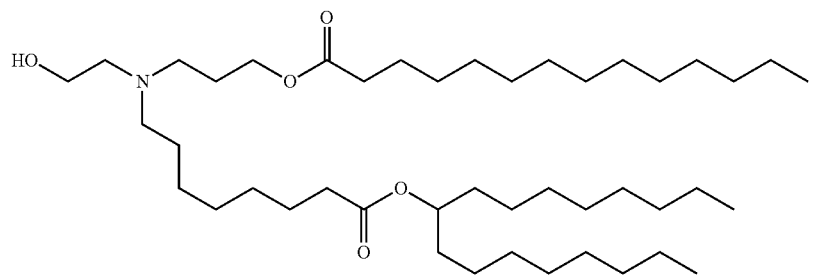
(Compound 98)
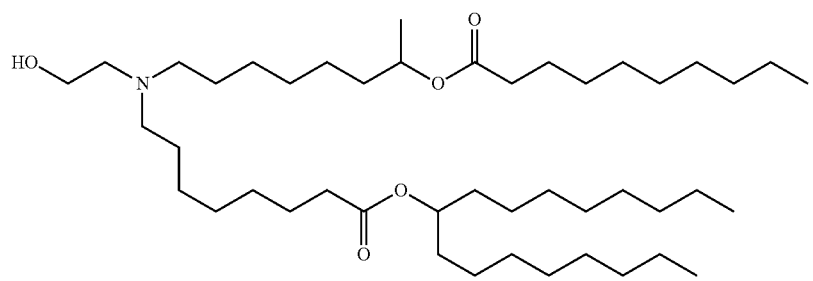
(Compound 99)
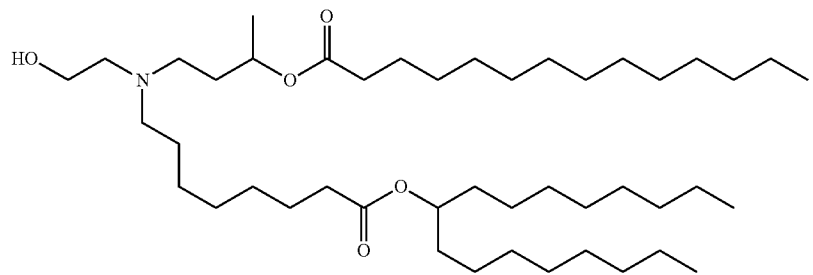
(Compound 100)
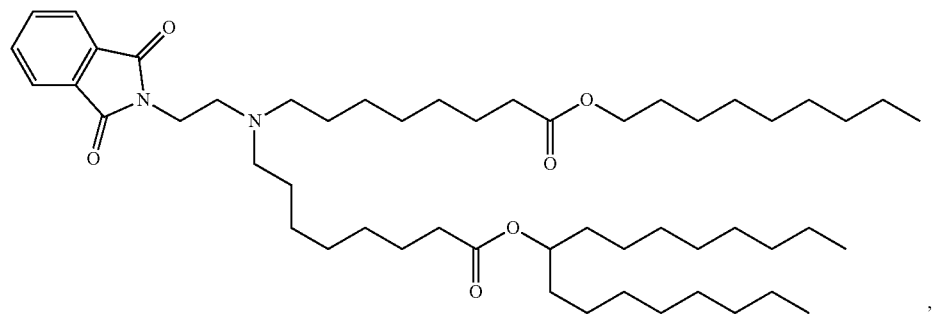

-continued
(Compound 101)
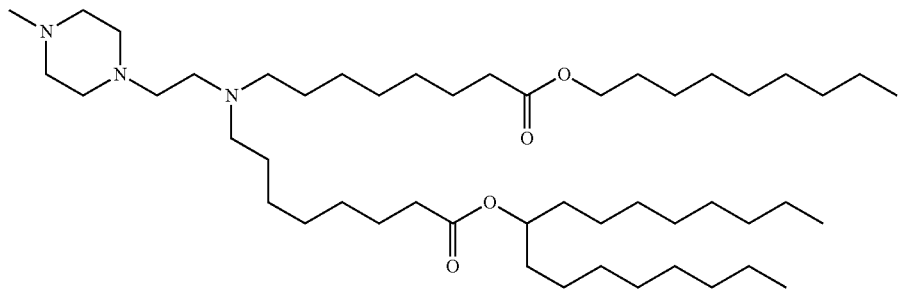
(Compound 102)
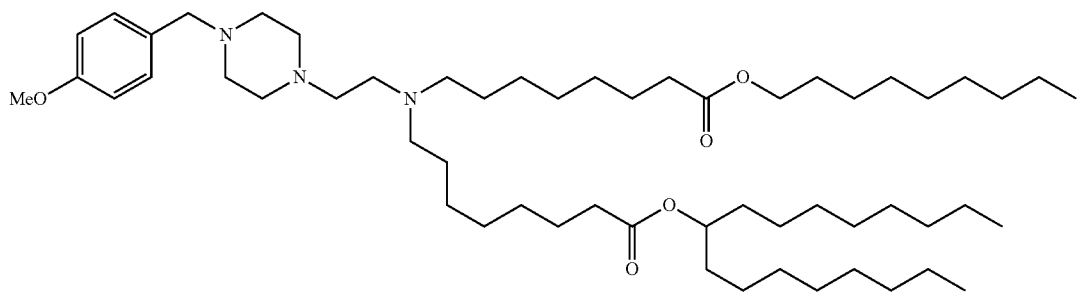
(Compound 103)
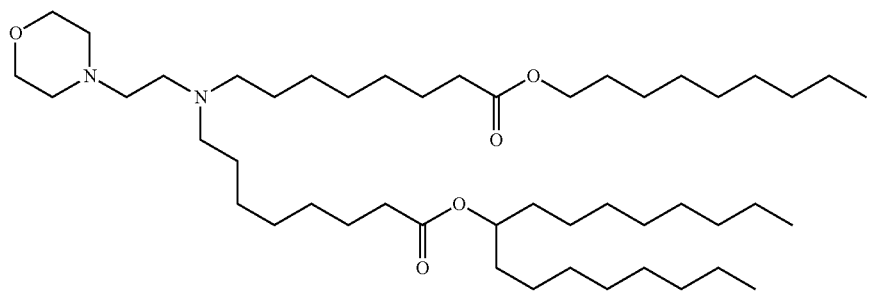
(Compound 104)
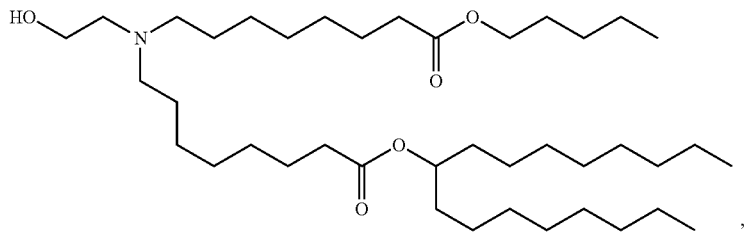
(Compound 105)
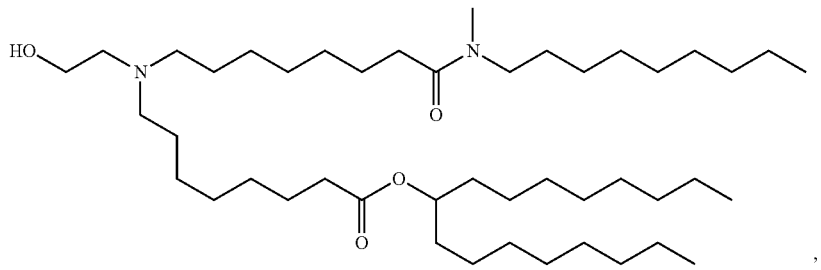

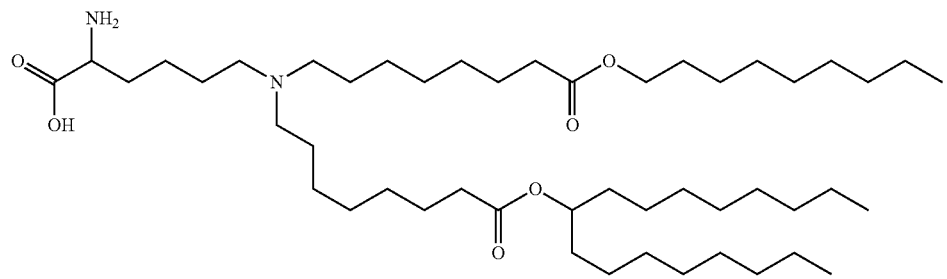
(Compound 106)
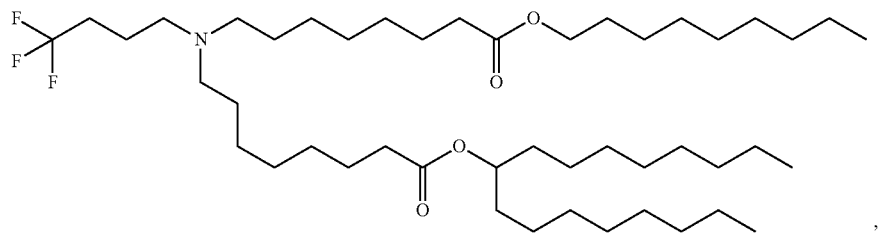
(Compound 107)
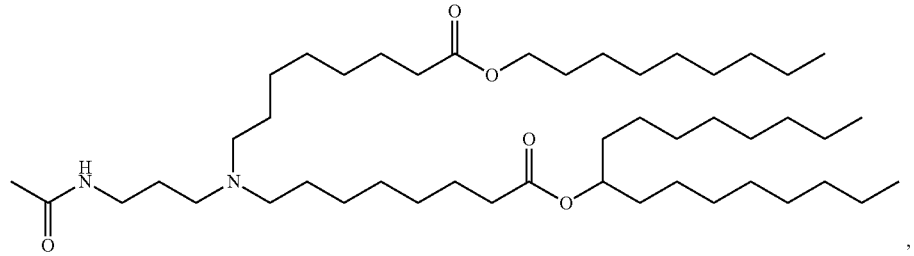
(Compound 108)
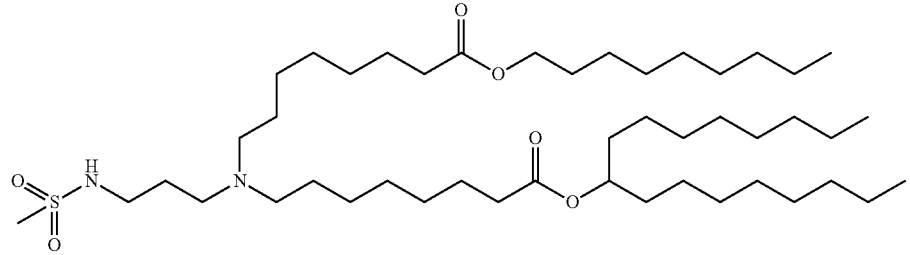
(Compound 109)
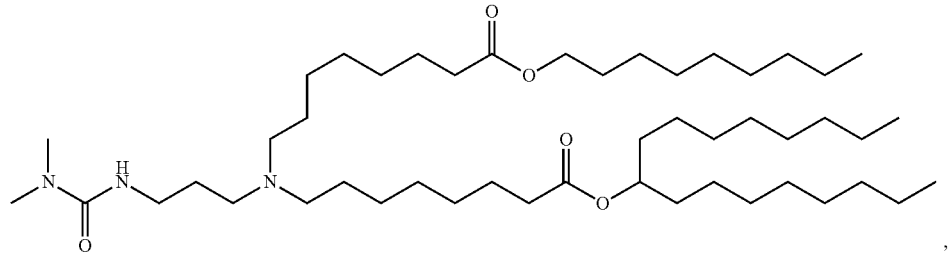
(Compound 110)
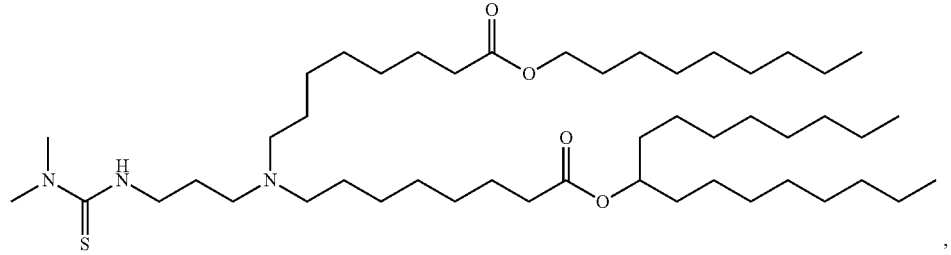
(Compound 111)

(Compound 112)
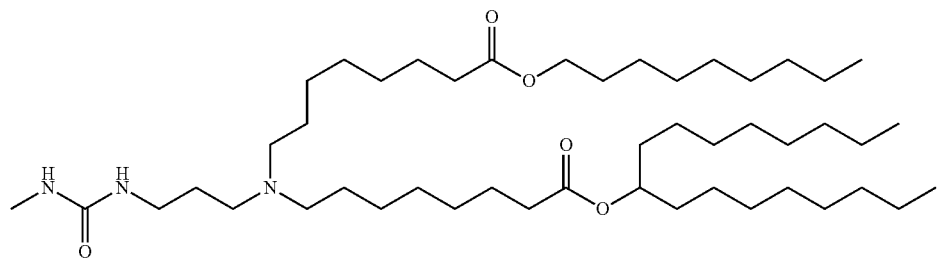
(Compound 113)
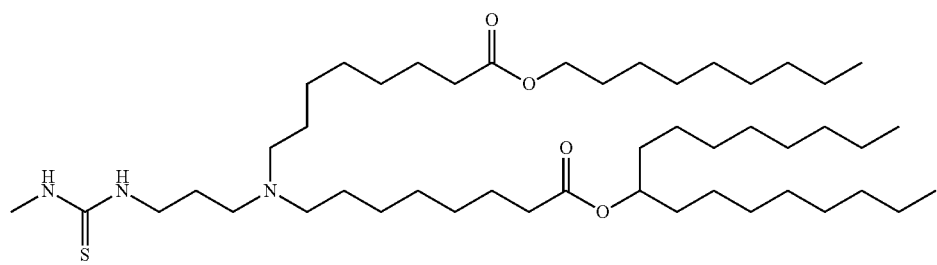
(Compound 114)
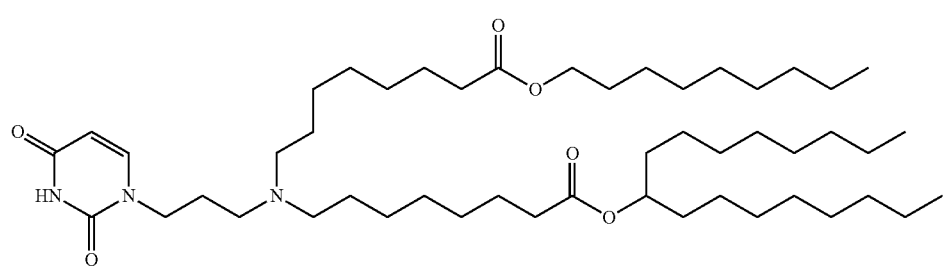
(Compound 115)
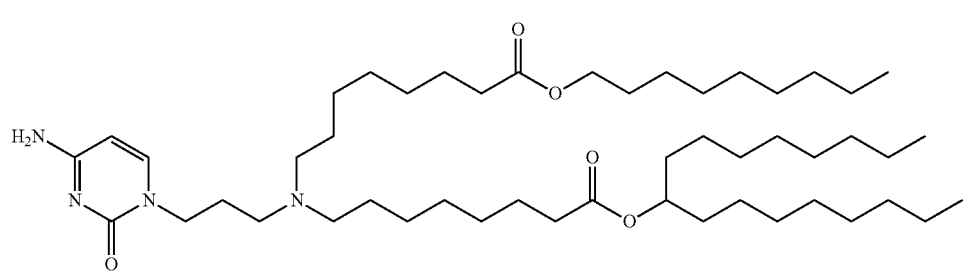
(Compound 116)
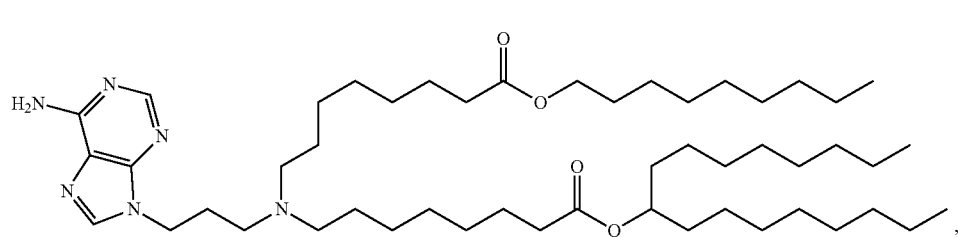
(Compound 117)
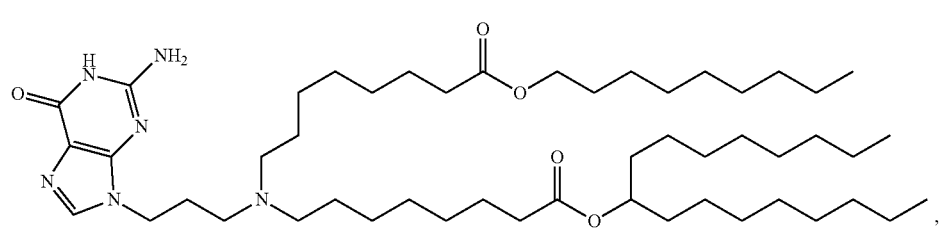

-continued
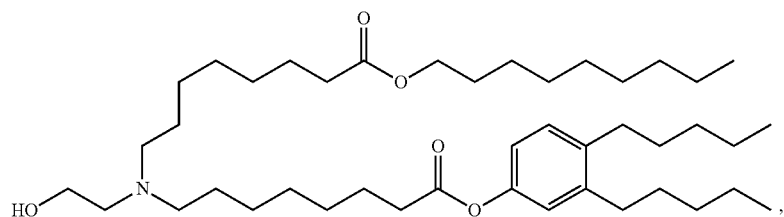
(Compound 118)
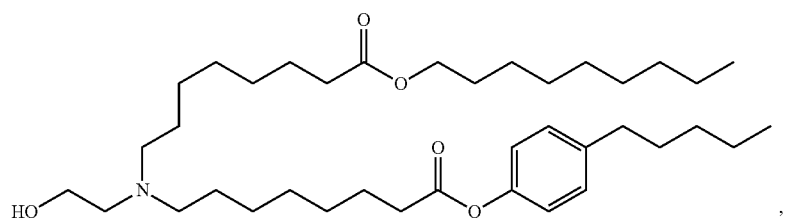
(Compound 119)
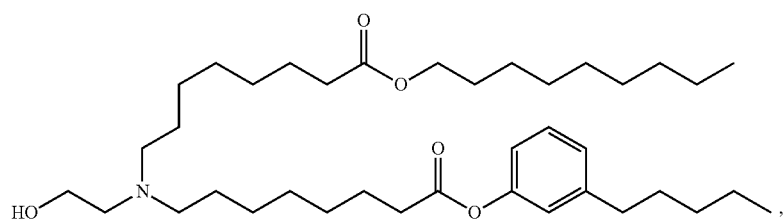
(Compound 120)
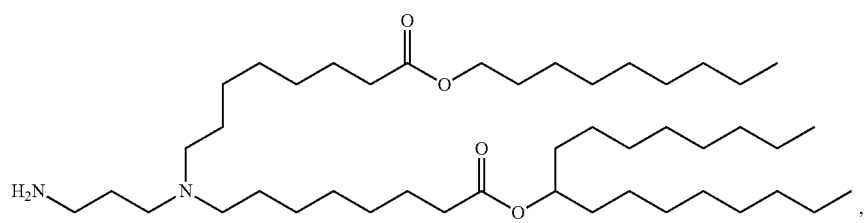
(Compound 121)
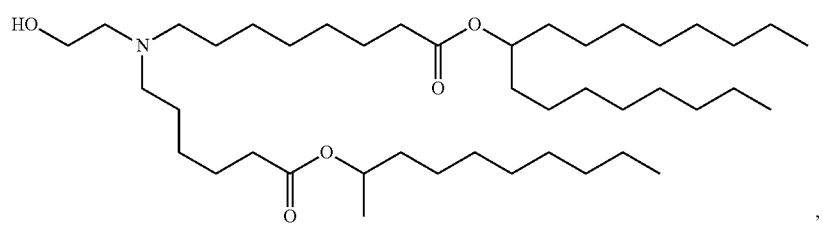
(Compound 122)
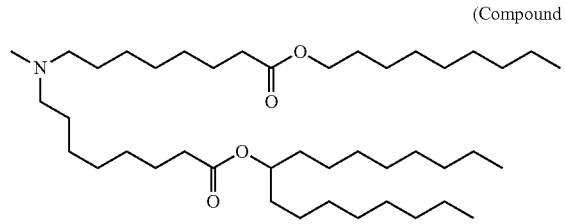
(Compound 123)
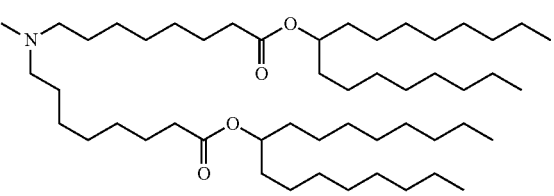
(Compound 124)
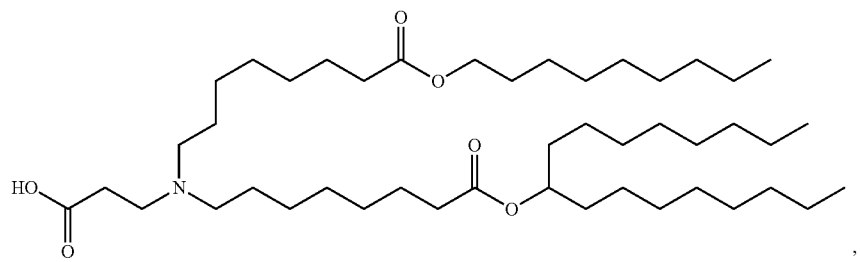
(Compound 125)

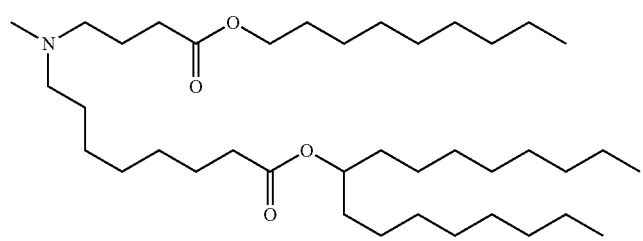
(Compound 126)
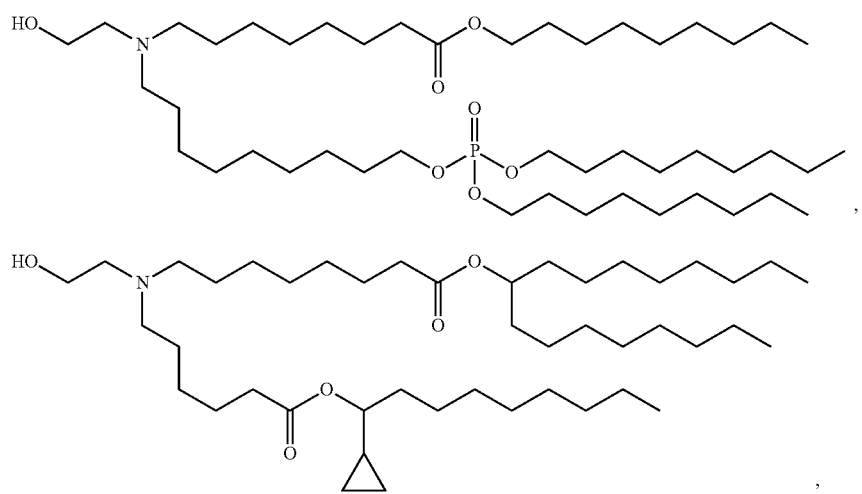
(Compound 127)
(Compound 128)
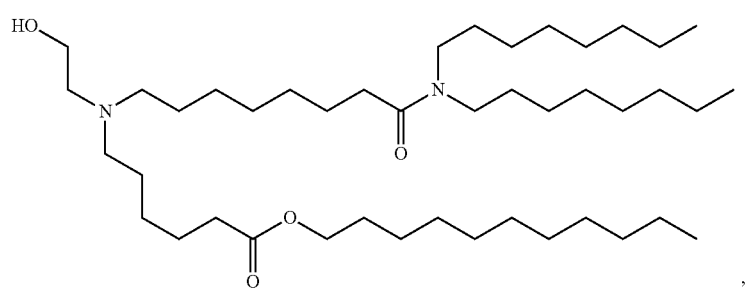
(Compound 129)
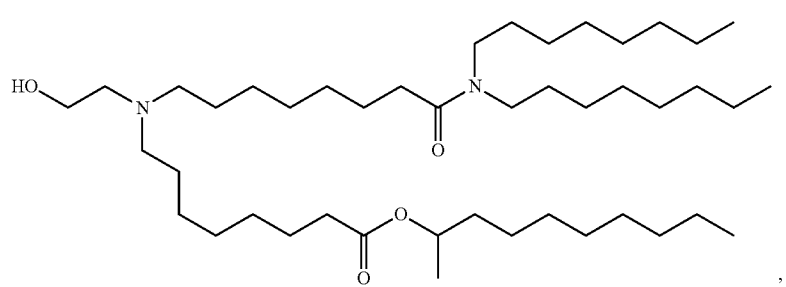
(Compound 130)
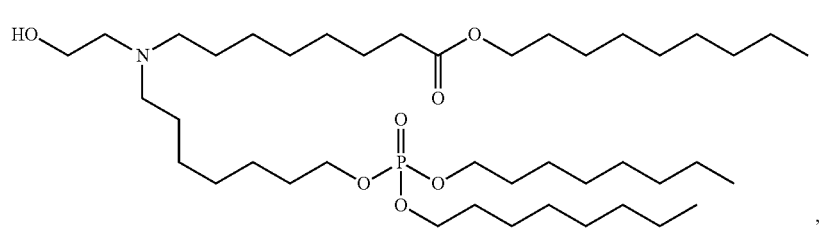
(Compound 131)

-continued
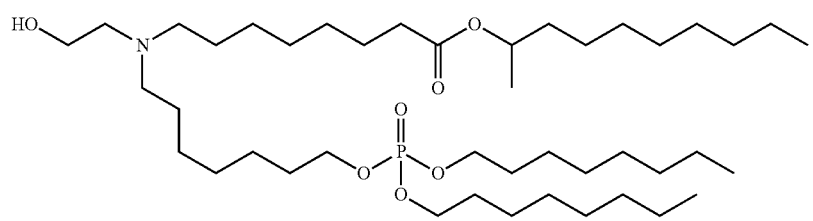
(Compound 132)
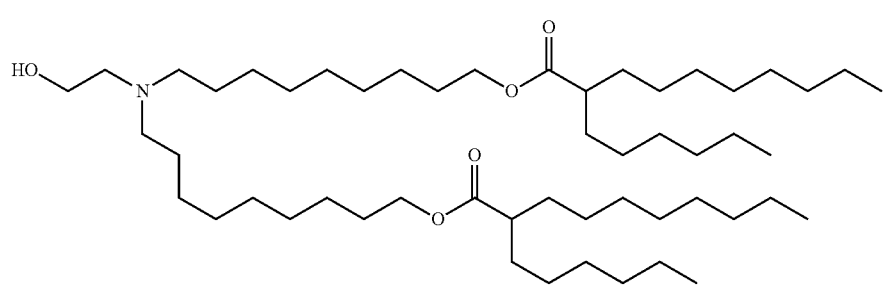
(Compound 133)
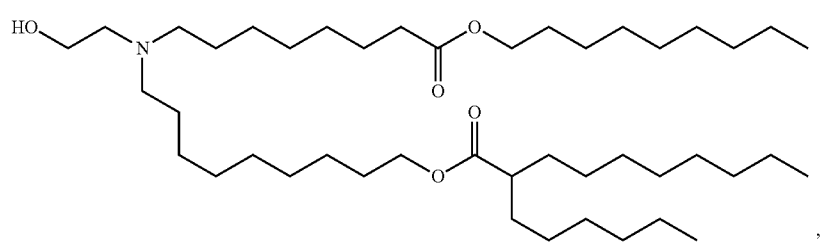
(Compound 134)
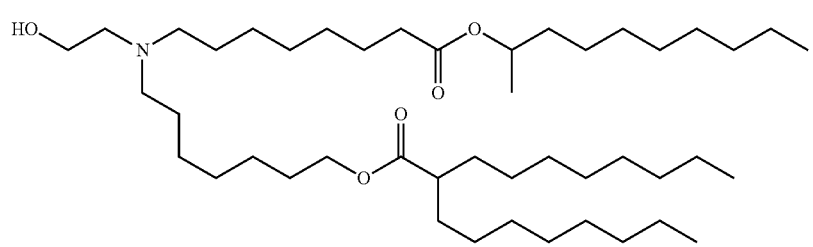
(Compound 135)
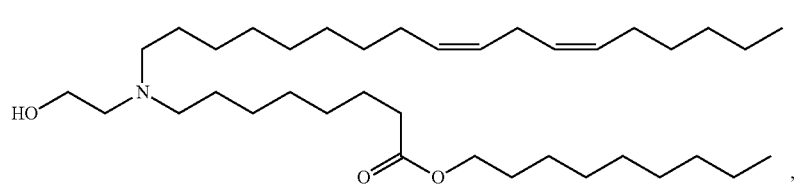
(Compound 136)
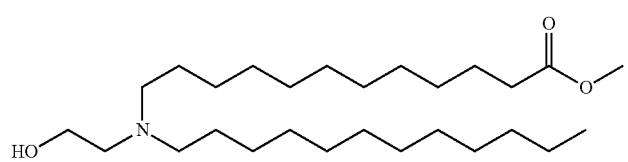
(Compound 137)
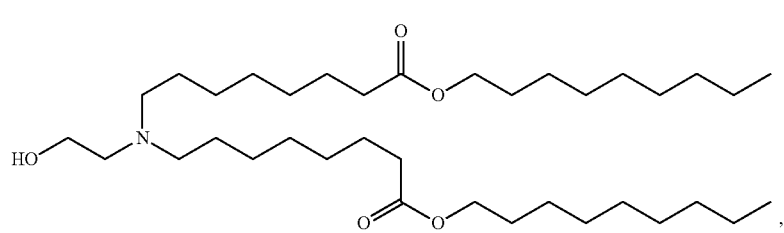
(Compound 138)

-continued
(Compound 139)
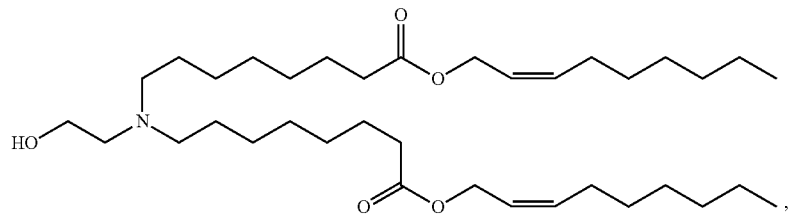
(Compound 140)
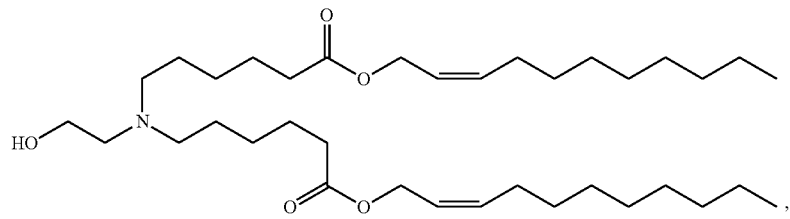
(Compound 141)
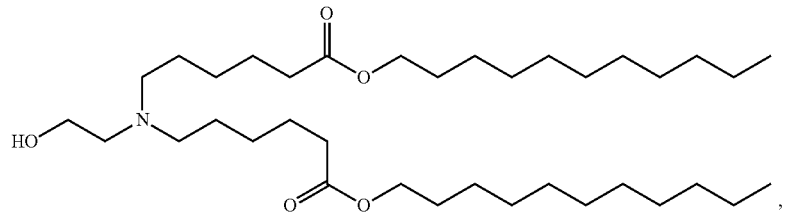
(Compound 142)
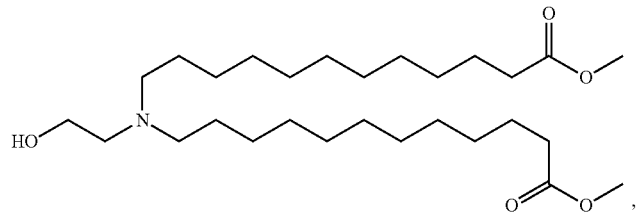
(Compound 143)
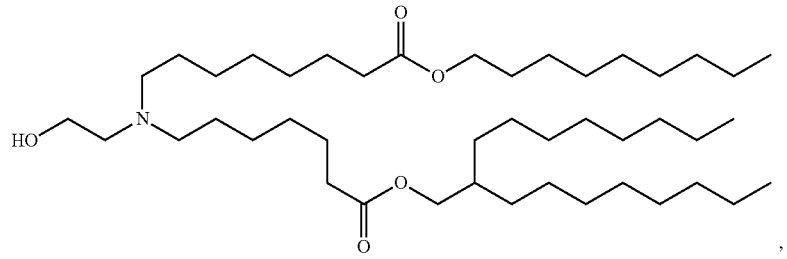
(Compound 144)
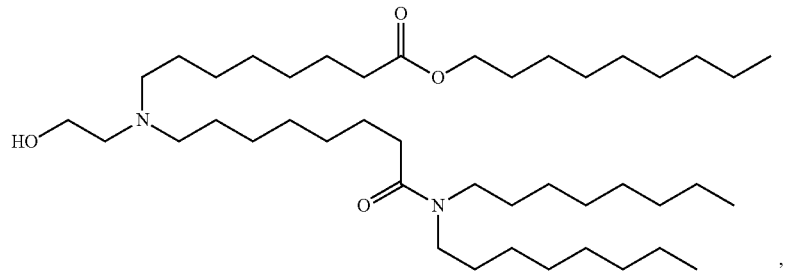

-continued
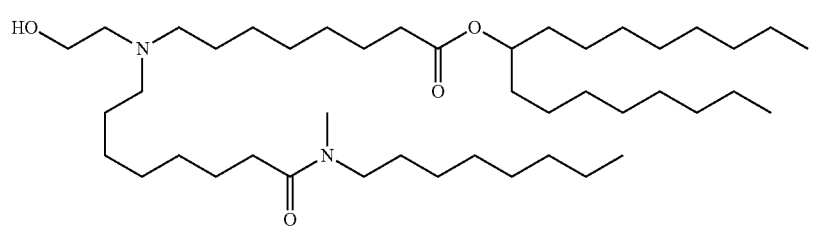
(Compound 145)
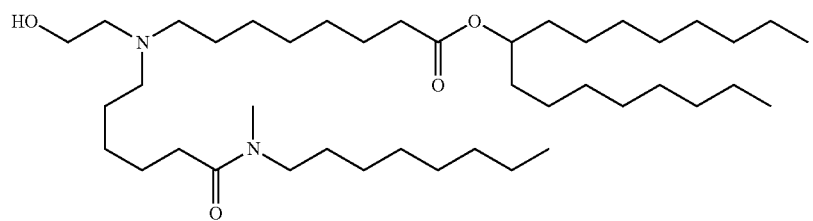
(Compound 146)
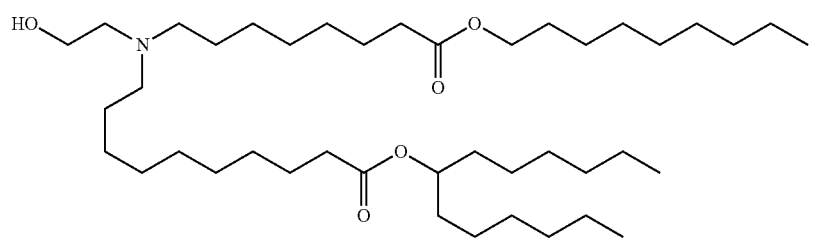
(Compound 147)
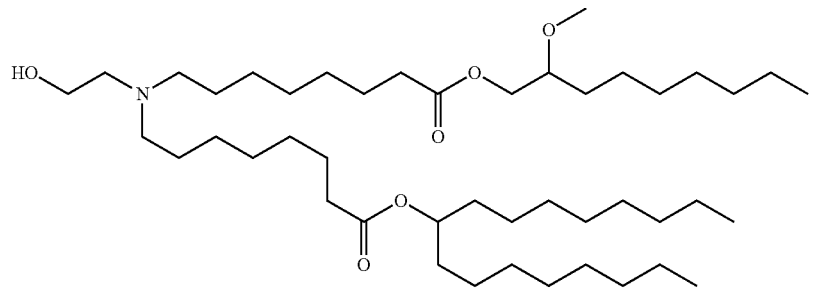
(Compound 148)
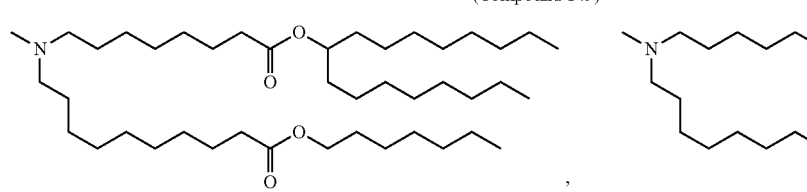
(Compound 149) (Compound 150)
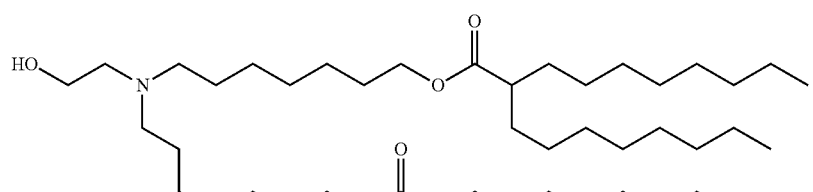
(Compound 151)
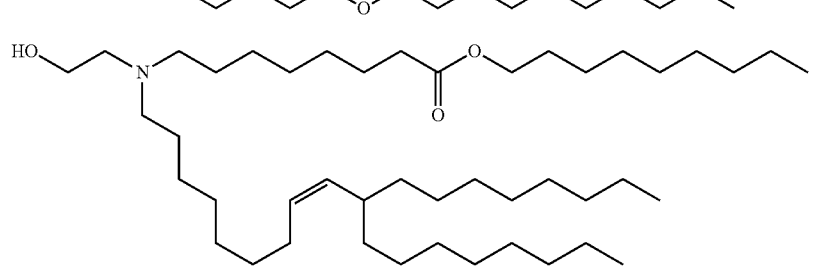
(Compound 152)

-continued
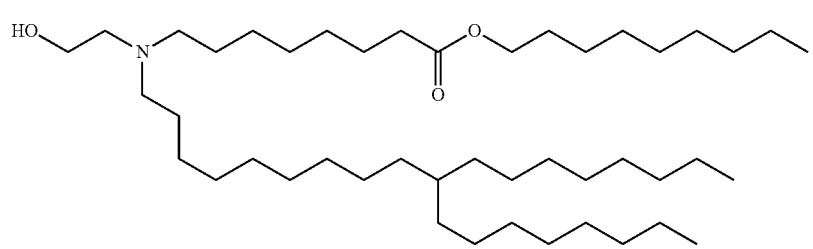
(Compound 153)
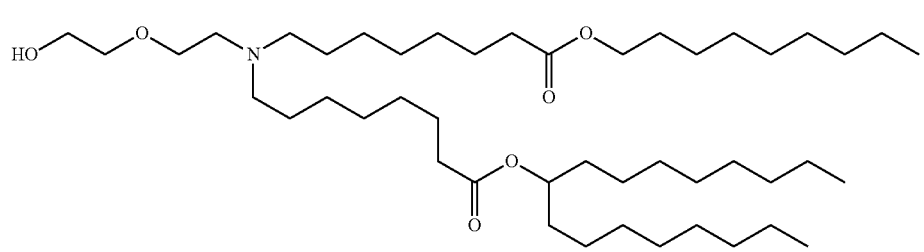
(Compound 154)
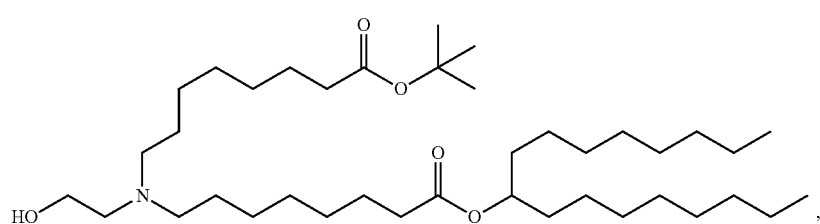
(Compound 155)
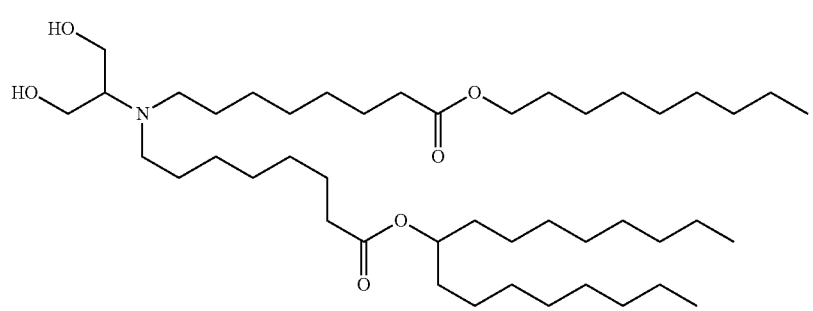
(Compound 156)
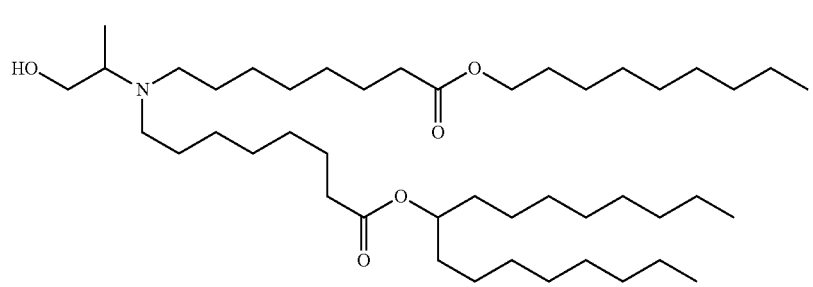
(Compound 157)
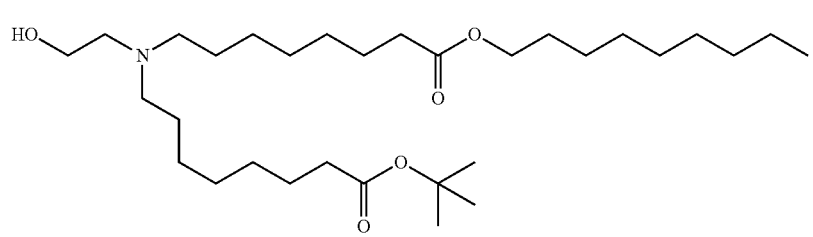
(Compound 158)

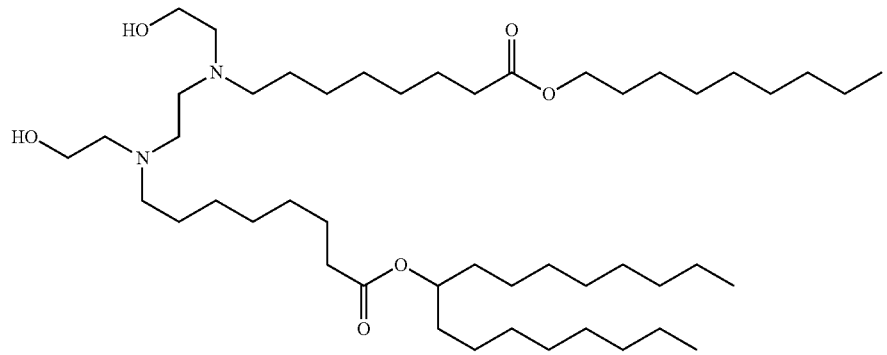
(Compound 159)
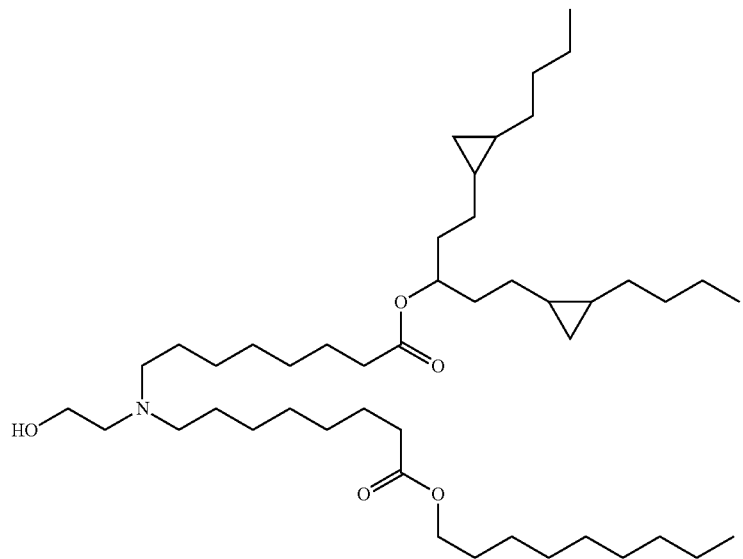
(Compound 160)
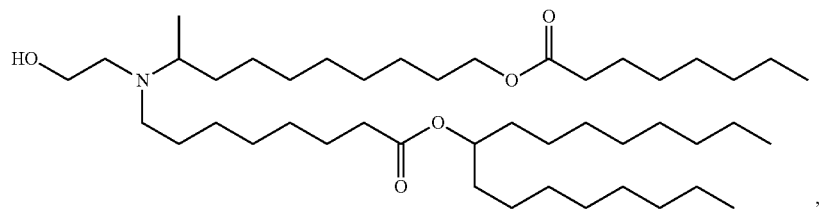
(Compound 161)
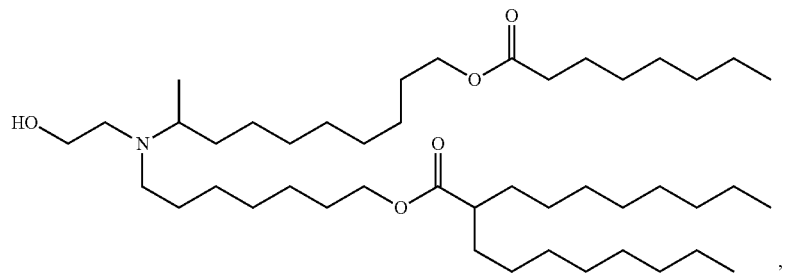
(Compound 162)

-continued
(Compound 163)
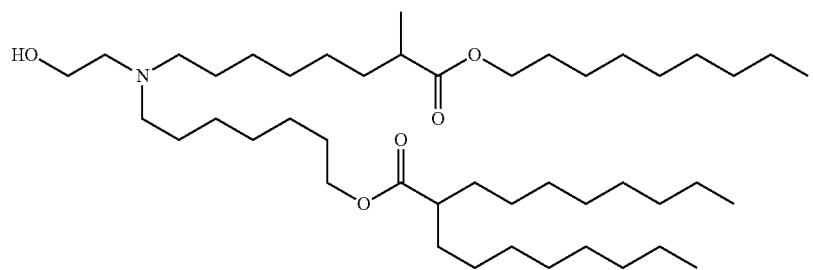
(Compound 164)
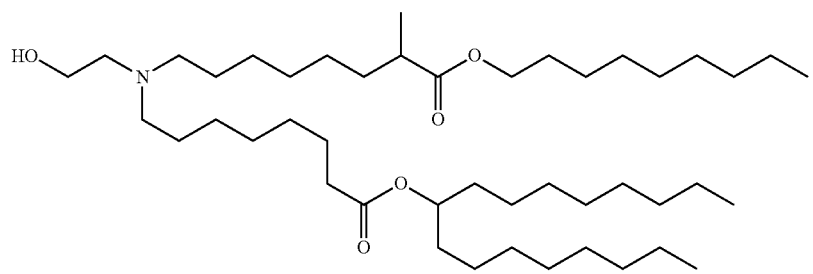
(Compound 165)
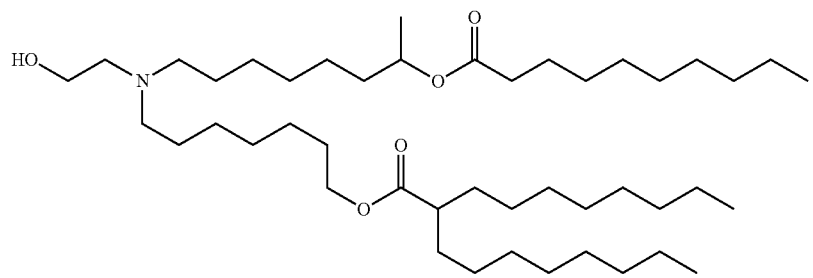
(Compound 166)
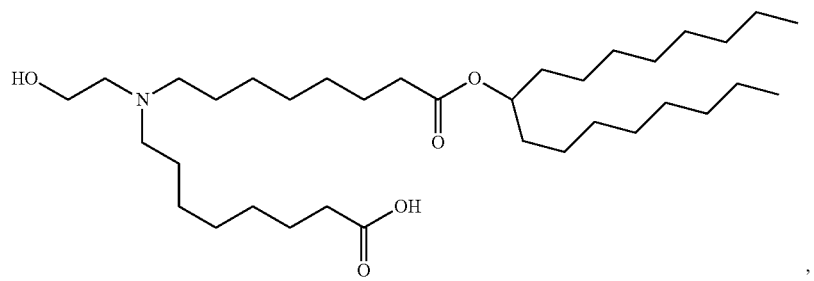
(Compound 167)
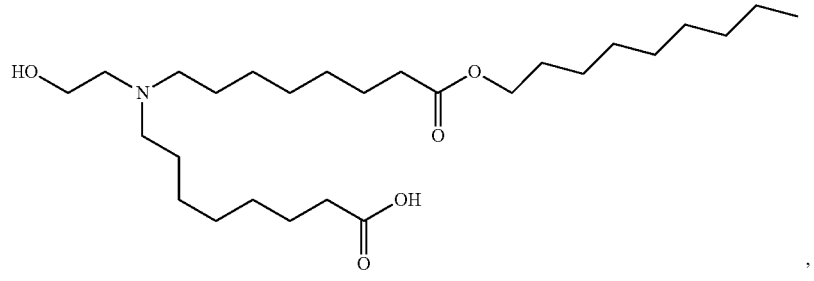

(Compound 168)
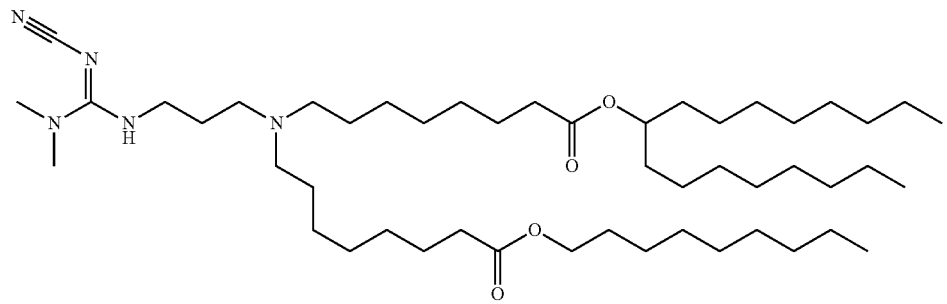
(Compound 169)
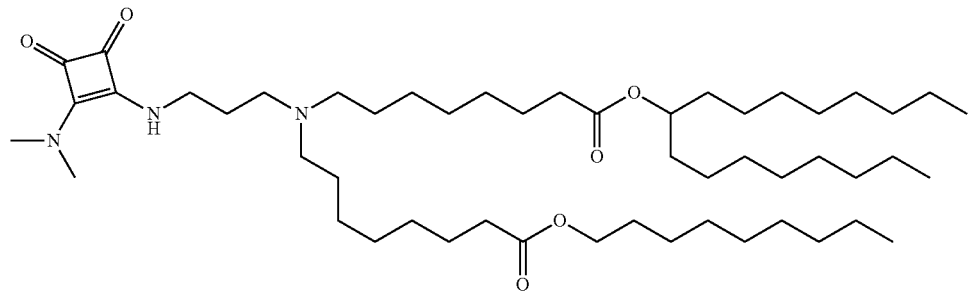
(Compound 170)
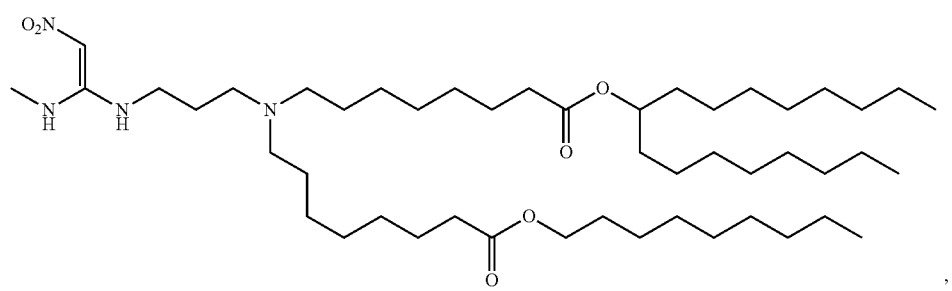
(Compound 171)
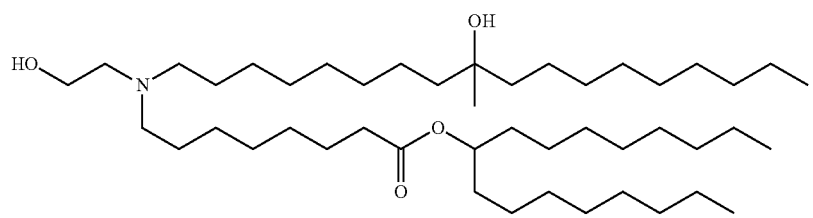
(Compound 172)
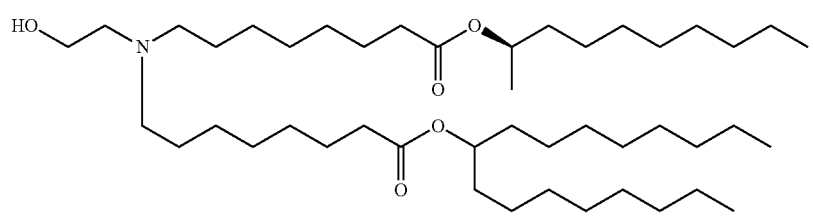
(Compound 173)
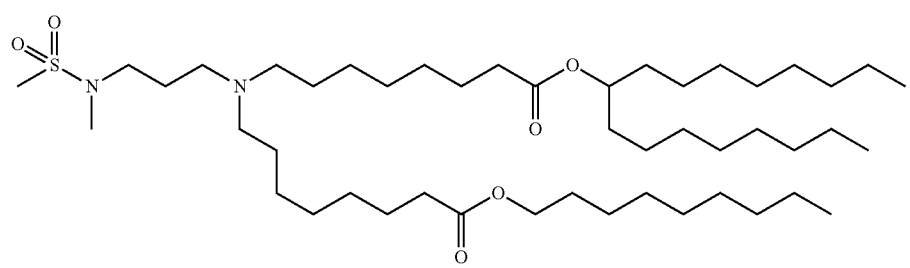

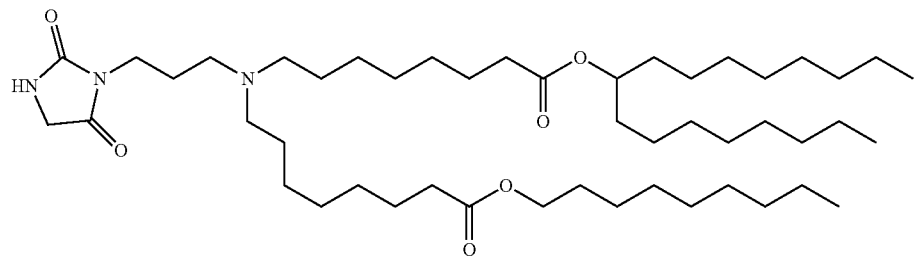
(Compound 174)
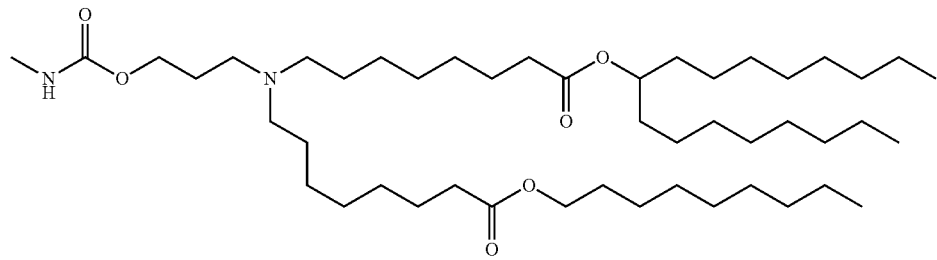
(Compound 175)
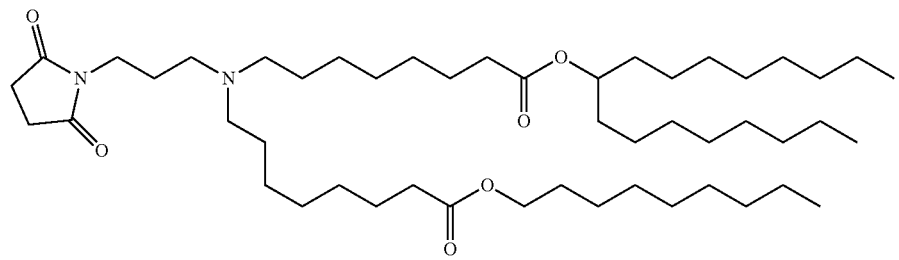
(Compound 176)
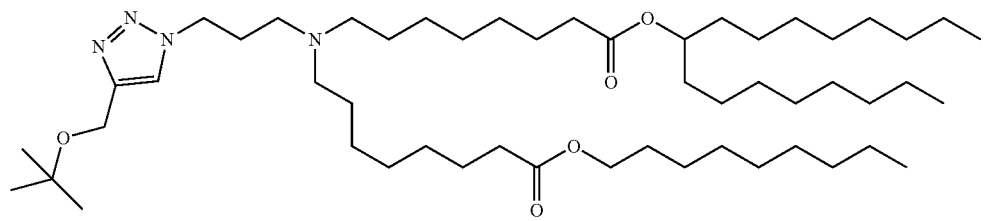
(Compound 177)
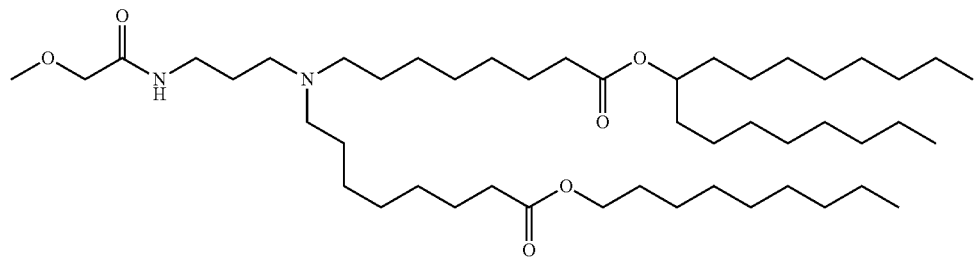
(Compound 178)
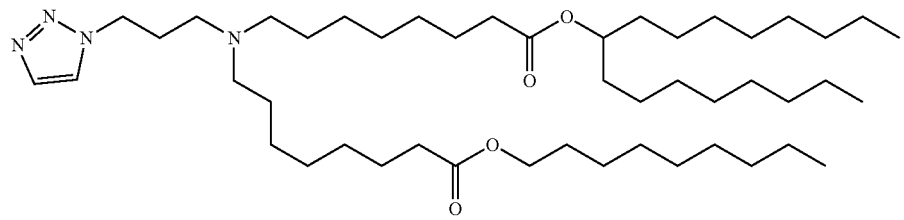
(Compound 179)

(Compound 180)
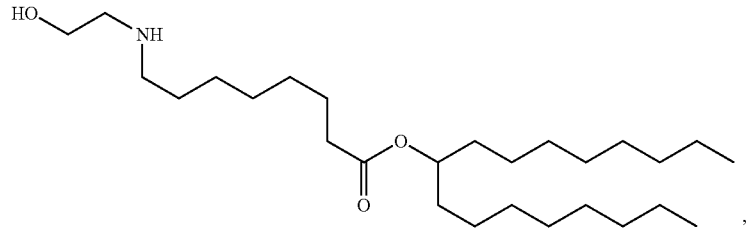
(Compound 181)
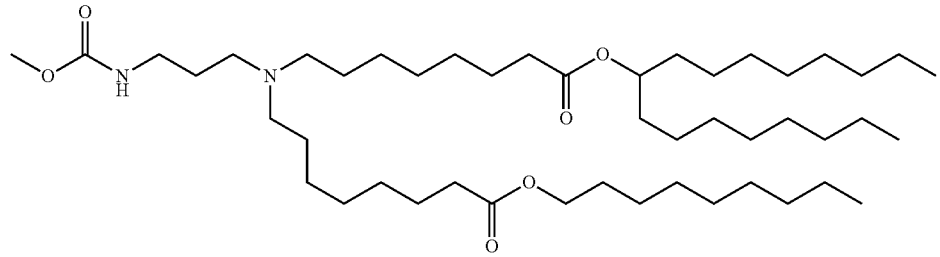
(Compound 182)
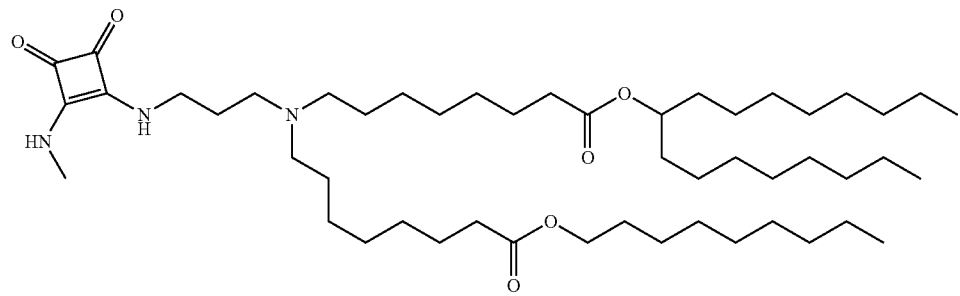
(Compound 183)
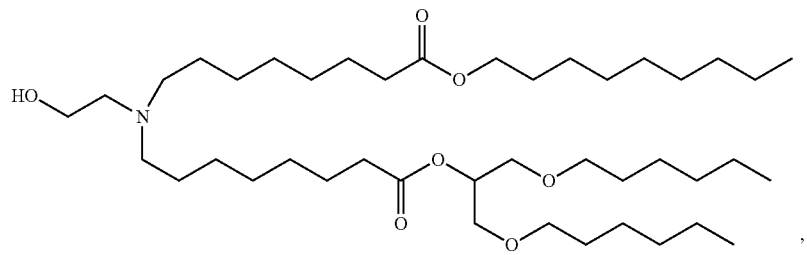
(Compound 184)
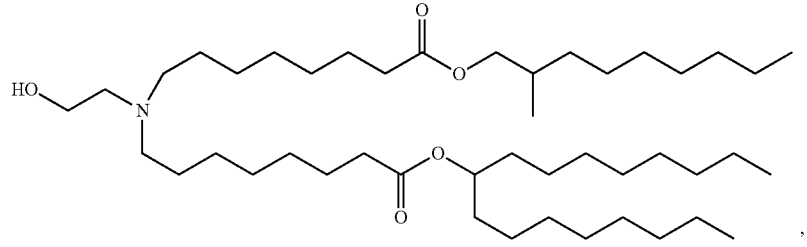
(Compound 185)
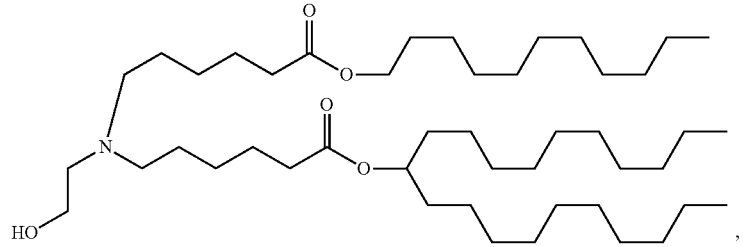

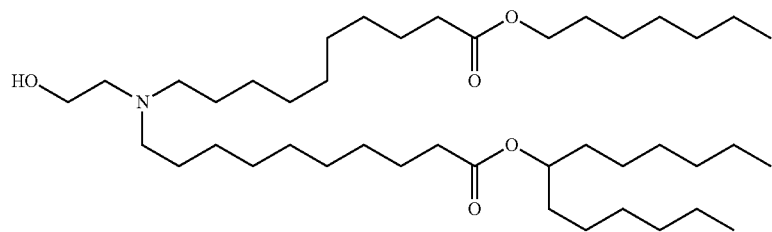
(Compound 186)
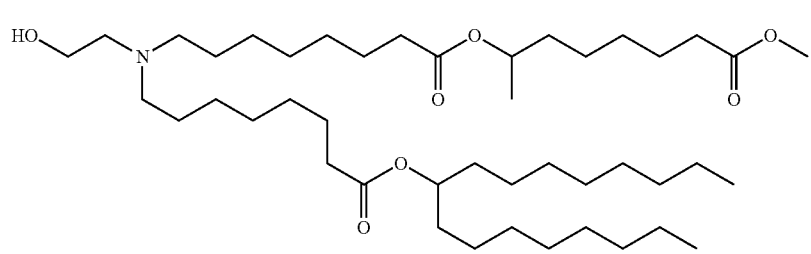
(Compound 187)
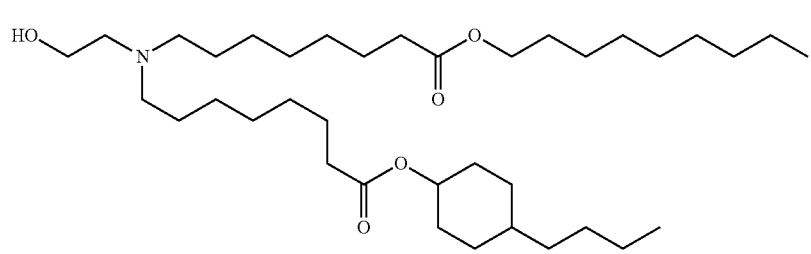
(Compound 188)
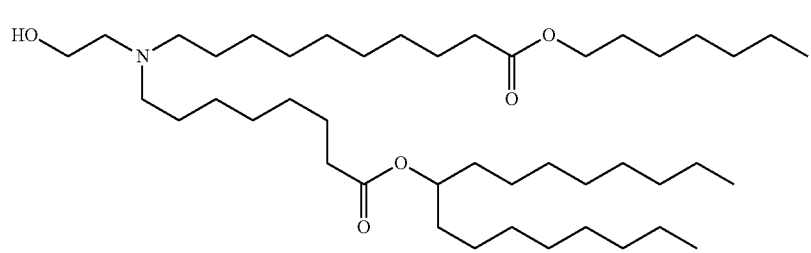
(Compound 189)
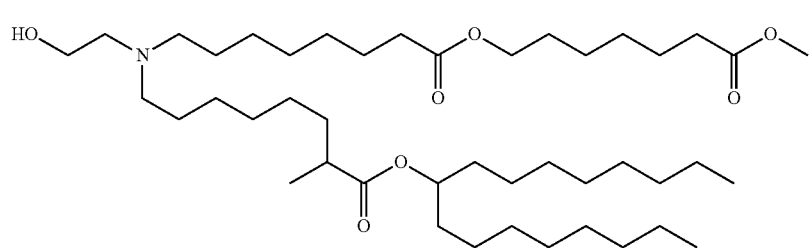
(Compound 190)
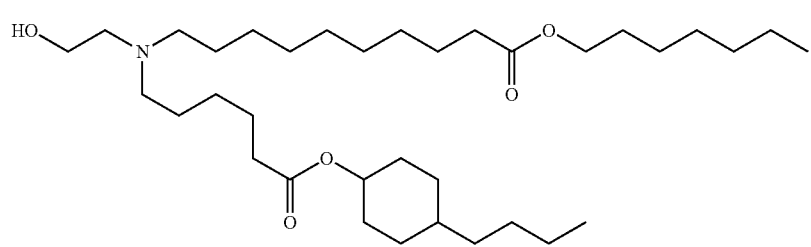
(Compound 191)

-continued
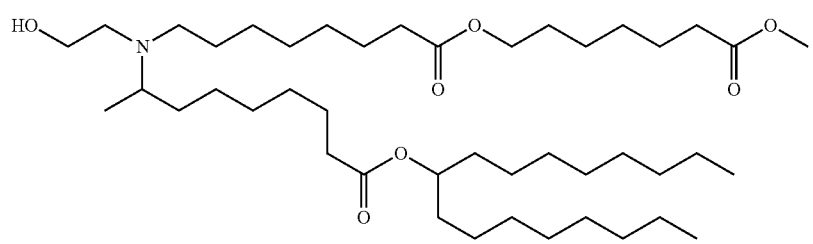
(Compound 192)
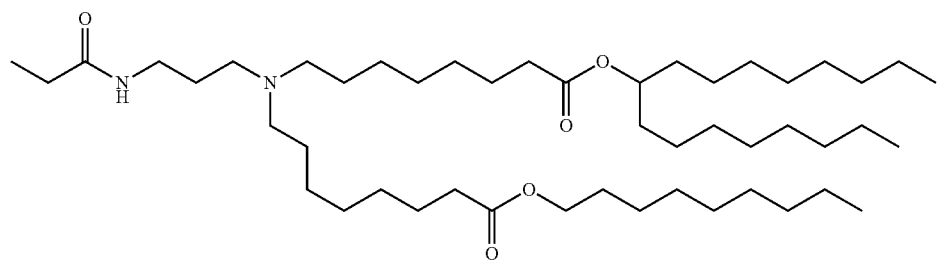
(Compound 193)
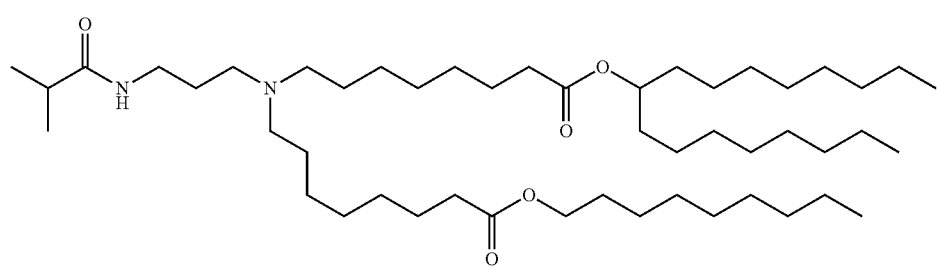
(Compound 194)
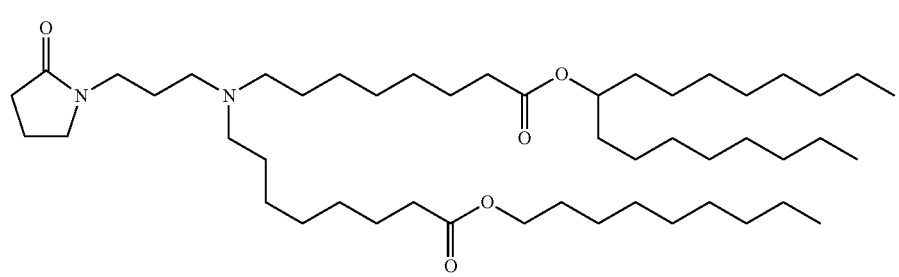
(Compound 195)
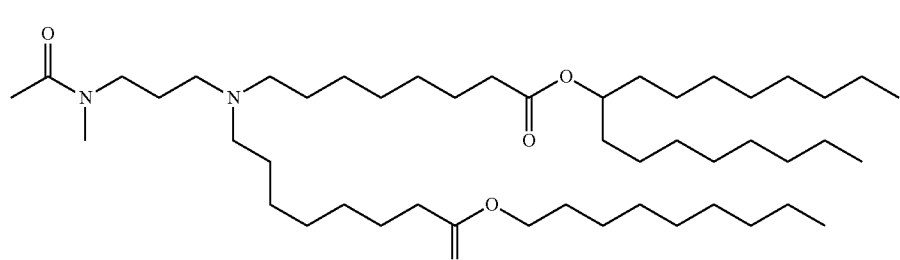
(Compound 196)
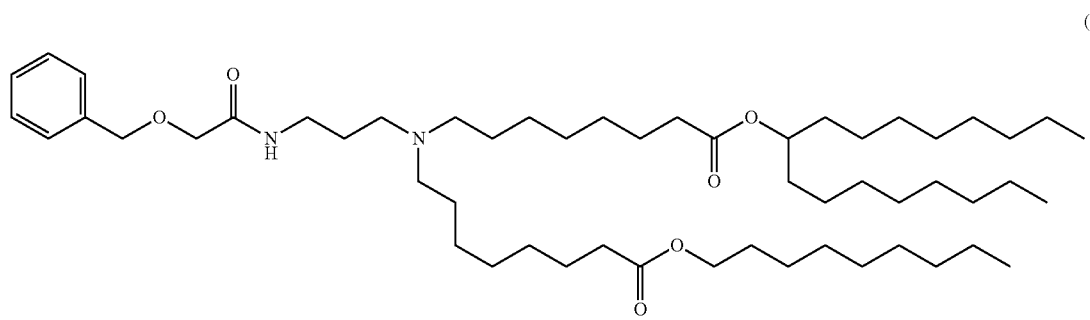
(Compound 197)

-continued
(Compound 198)
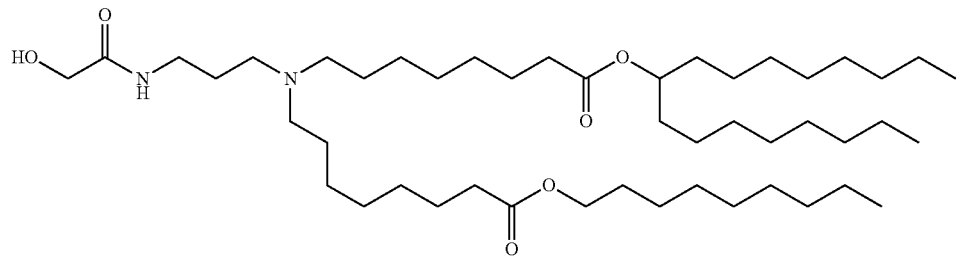
(Compound 199)
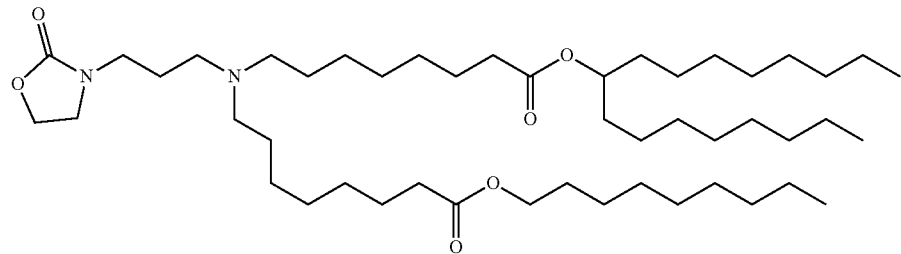
(Compound 200)
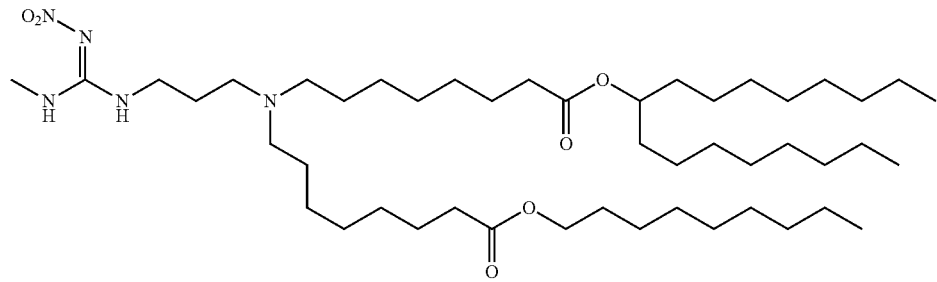
(Compound 201)
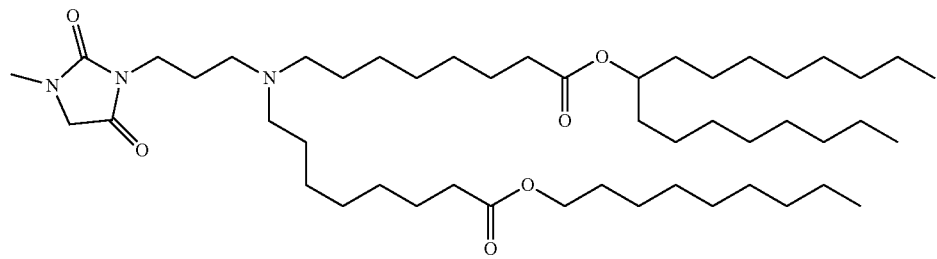
(Compound 202)
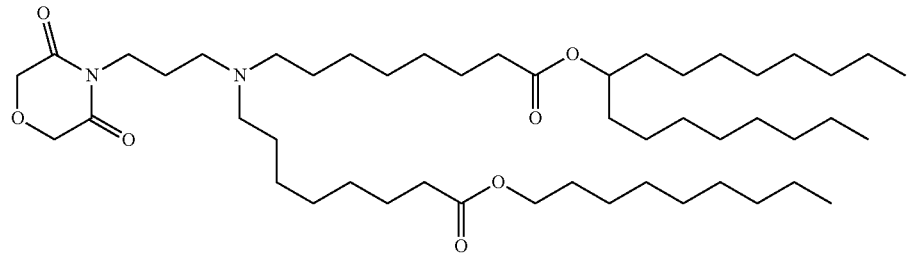
(Compound 203)
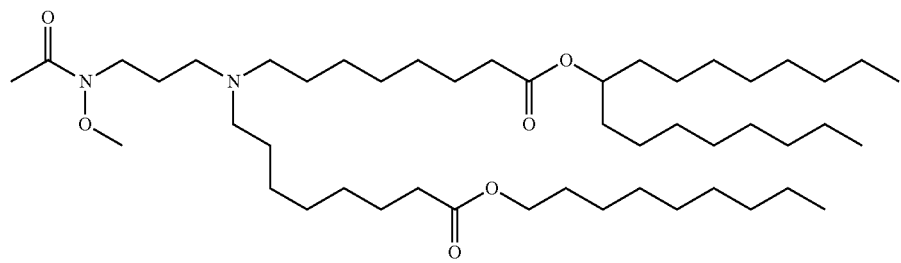

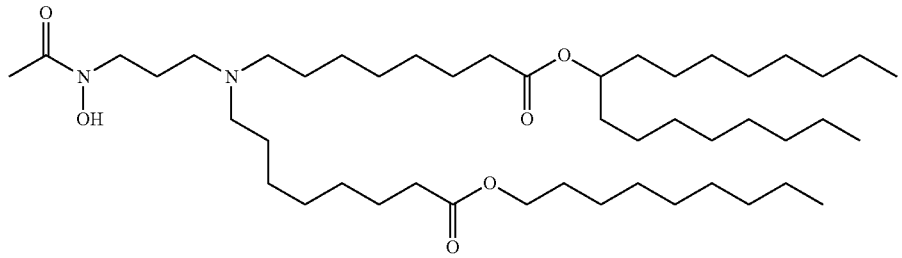
(Compound 204)
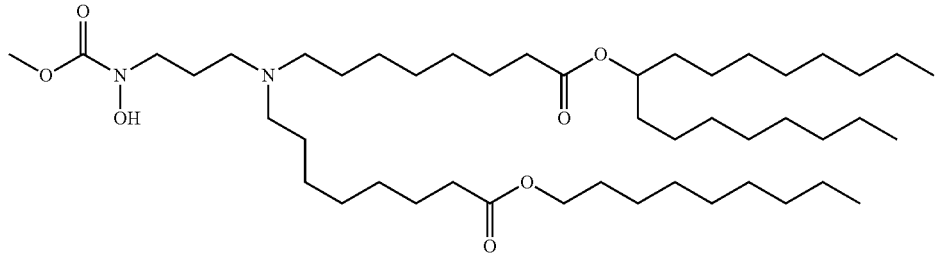
(Compound 205)
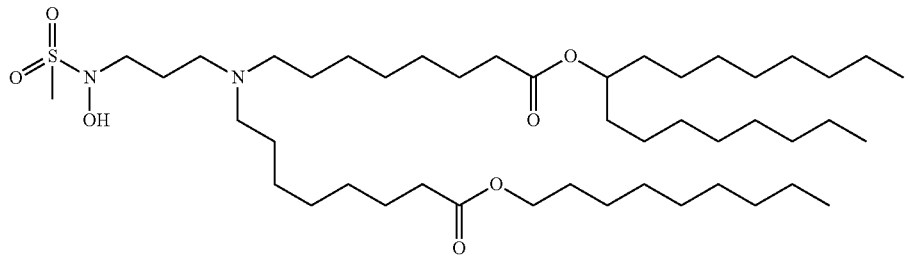
(Compound 206)
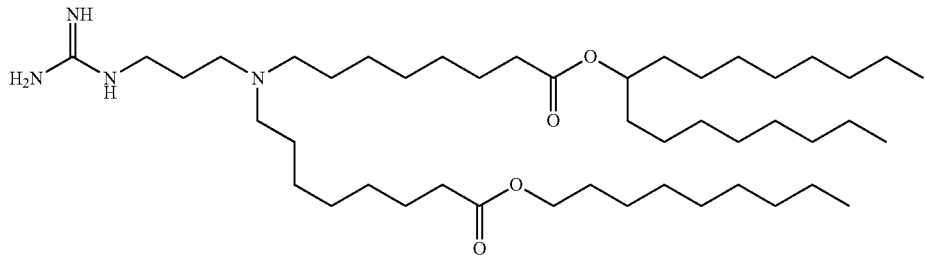
(Compound 207)
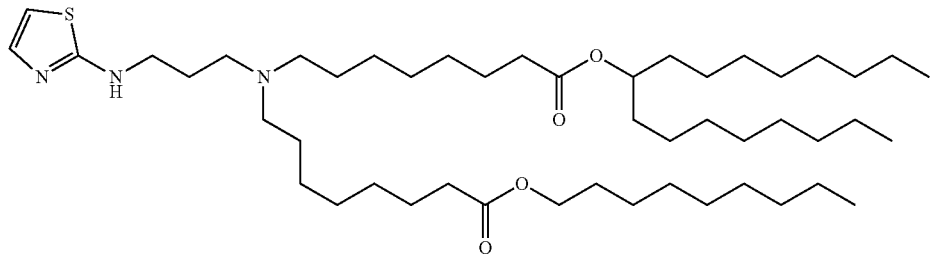
(Compound 208)
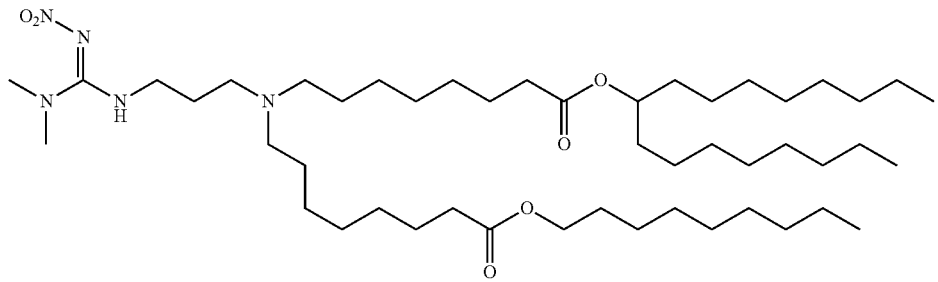
(Compound 209)

(Compound 210)
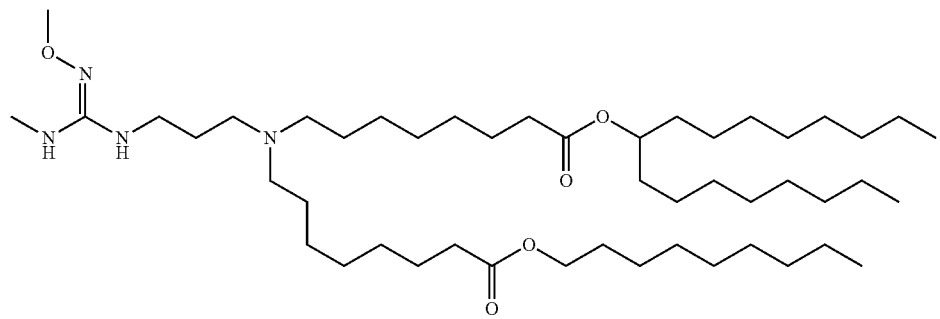
(Compound 211)
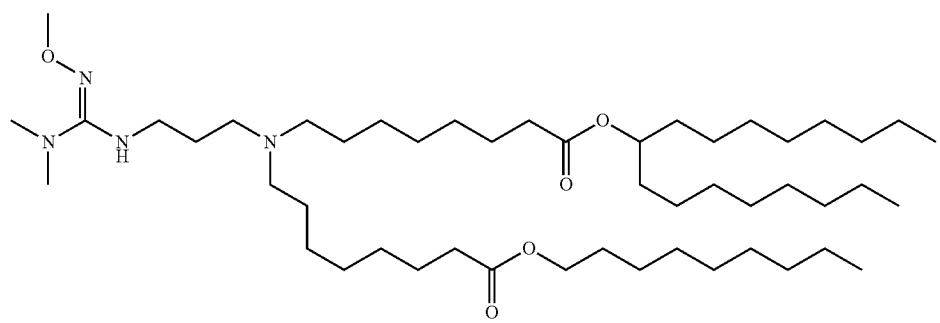
(Compound 212)
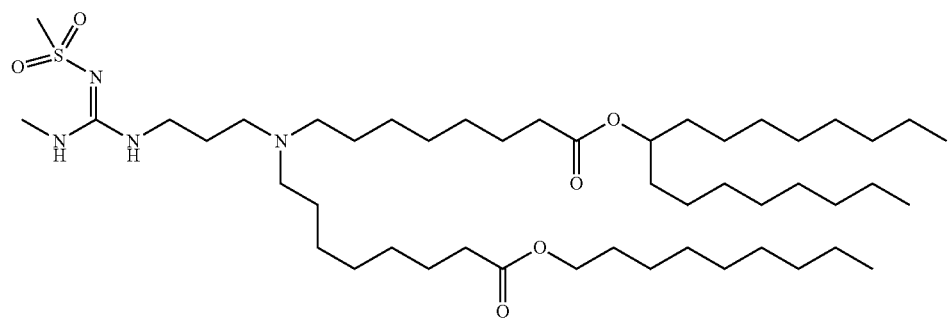
(Compound 213)
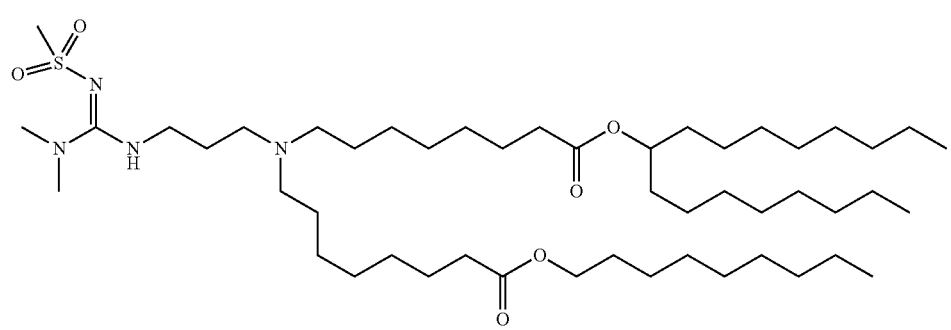
(Compound 214)
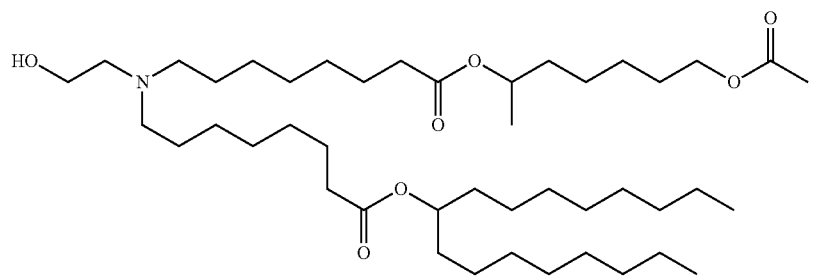

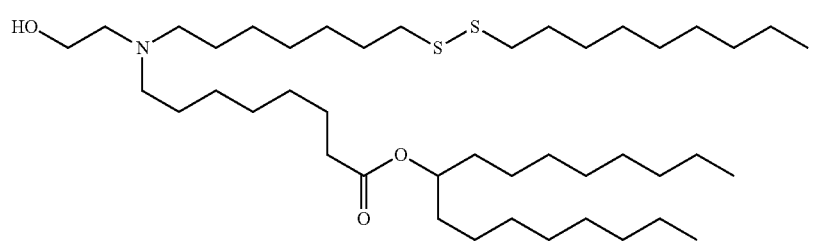
(Compound 215)
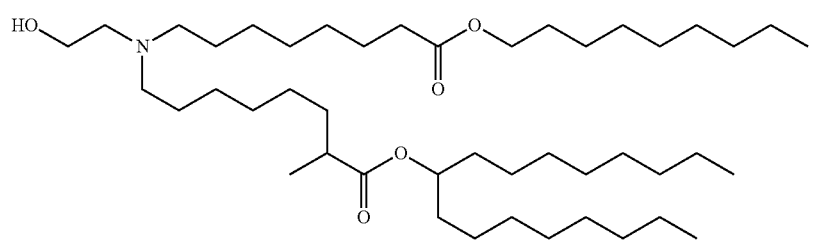
(Compound 216)
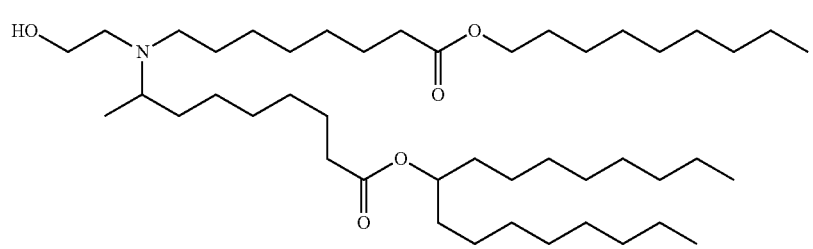
(Compound 217)
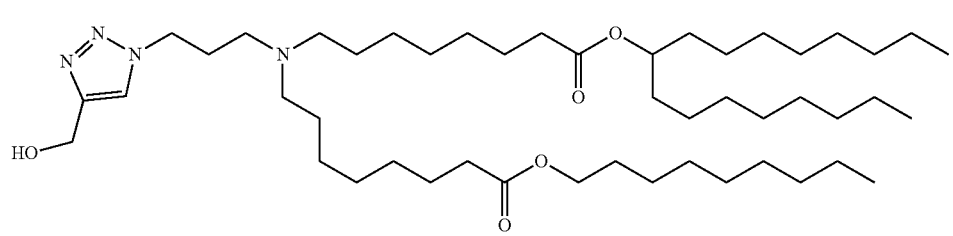
(Compound 218)
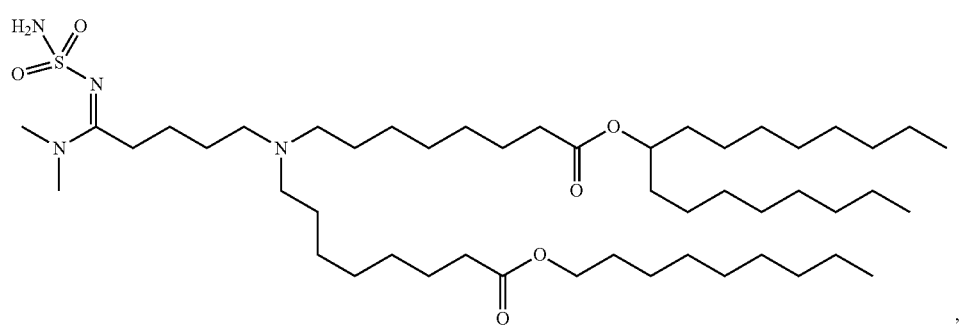
(Compound 219)
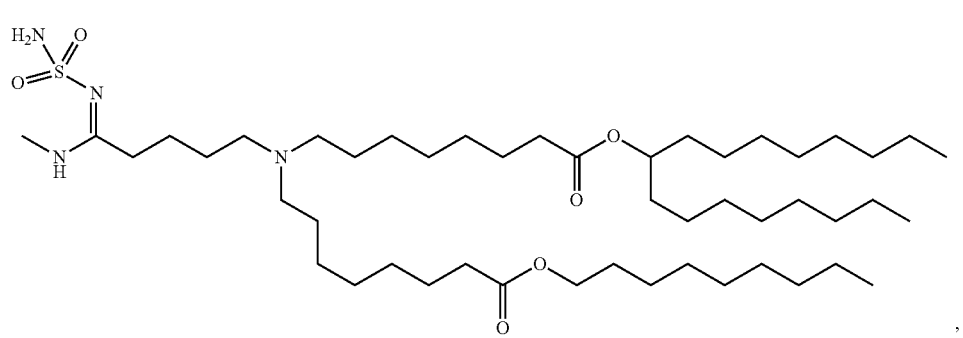
(Compound 220)

-continued
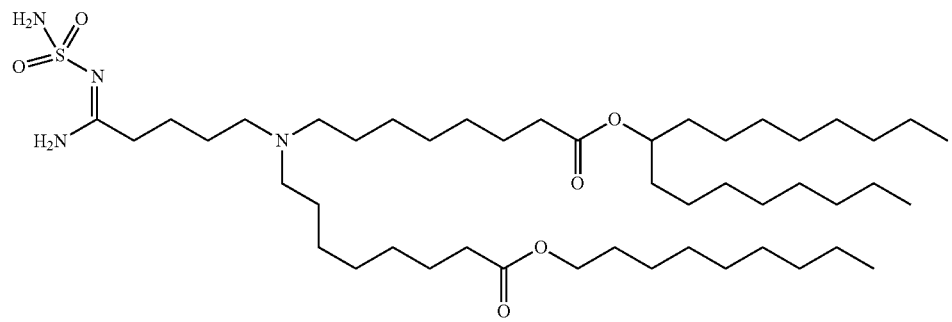
(Compound 221)
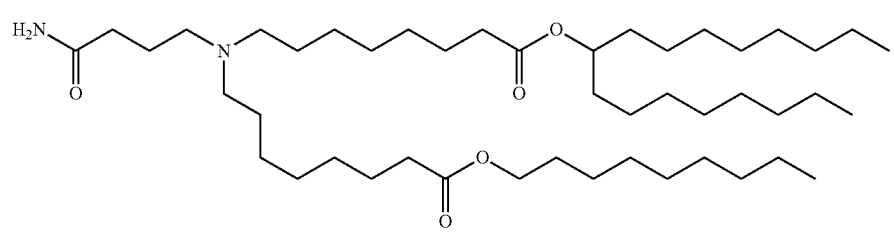
(Compound 222)
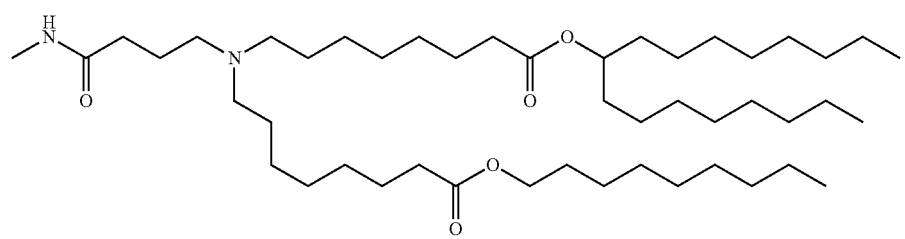
(Compound 223)
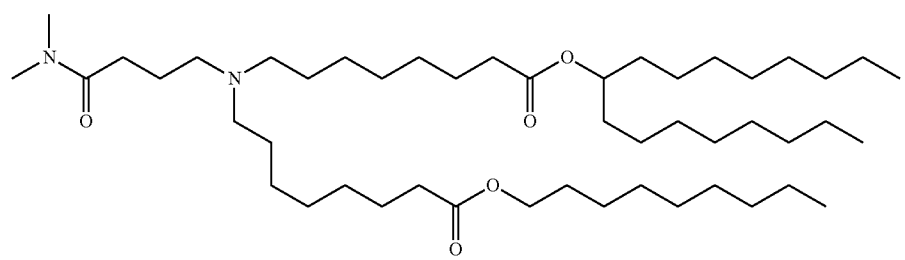
(Compound 224)
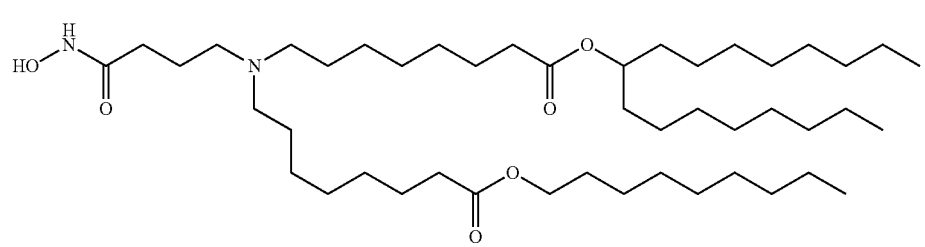
(Compound 225)
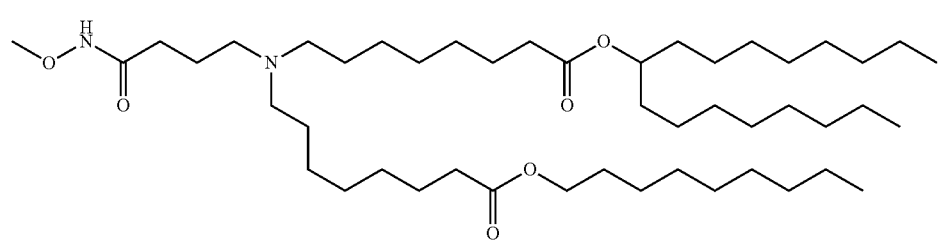
(Compound 226)

-continued
(Compound 227)
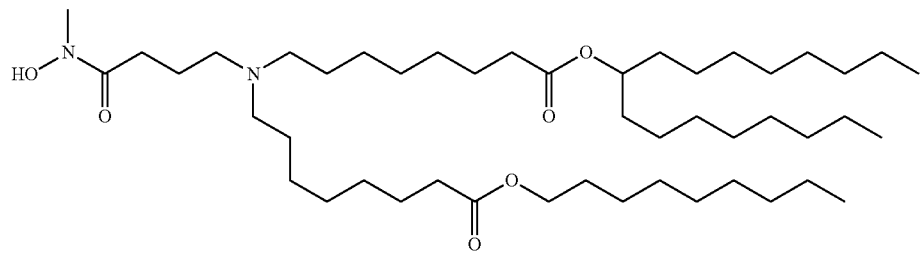
(Compound 228)
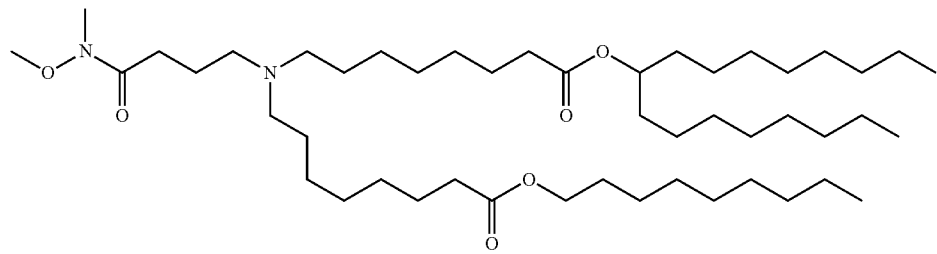
(Compound 229)
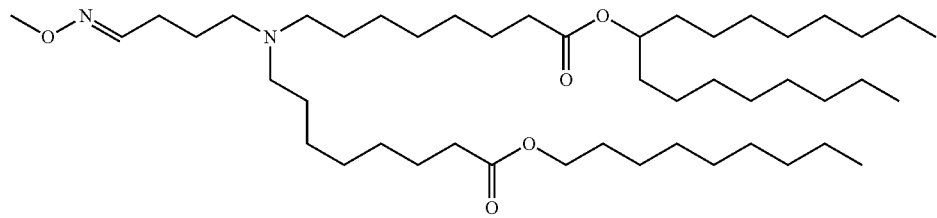
(Compound 230)
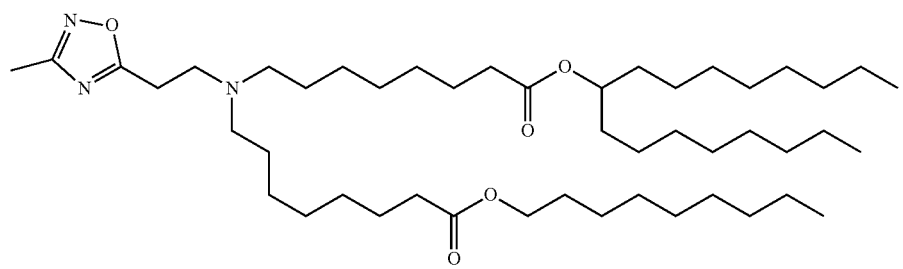
(Compound 231)
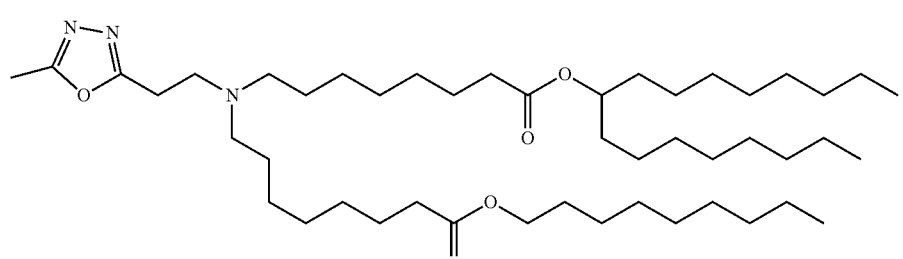
(Compound 232)
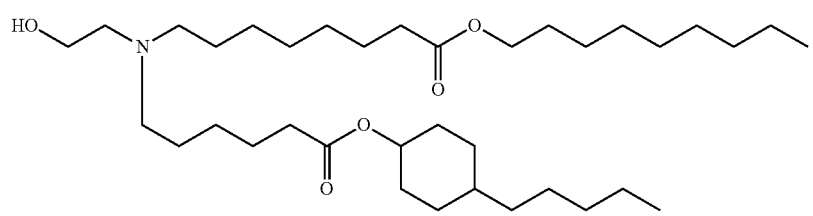
and salts and isomers thereof.

In some embodiments, a nanoparticle comprises the following compound:

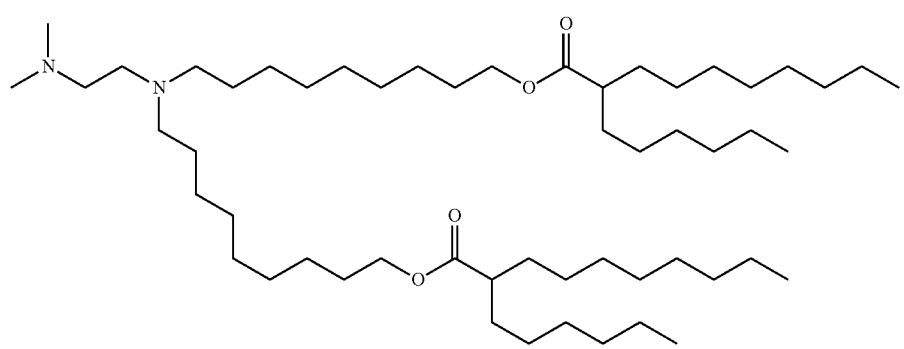

(Compound 233)

or salts and isomers thereof.

In some embodiments, a lipid nanoparticle comprises Compounds 3, 18, 20, 25, 26, 29, 30, 60, 108-112, or 122.

In some embodiments, the nanoparticle has a polydispersity value of less than 0.4 (e.g., less than 0.3, 0.2 or 0.1).

In some embodiments, the nanoparticle has a net neutral charge at a neutral pH value.

The following examples are intended to be illustrative of certain embodiments and are non-limiting. The entire contents of all of the references (including literature references, issued patents, published patent applications, and co pending patent applications) cited throughout this application are hereby expressly incorporated by reference.

EXAMPLES

Example 1

*Thermotoga maritima* RNase III (TmR3) Purification

Initial affinity purification experiments using immobilized wild-type *Escherichia coli* (*E. coli*) RNase III resulted in non-specific degradation of the RNA, which was attributed to the structure of the mRNA. To address the problem of non-specific degradation, additional affinity purification experiments were performed at elevated temperatures using a hardier, thermostable *Thermotoga maritima* RNase III (TmR3), which has high sequence homology to *E. coli* RNase III (Protein BLAST (NCBI) E value of $2^{-50}$; sequence alignment shown in FIG. 6). A catalytically-inactive form of TmR3 was also used. The mutation in the catalytically-essential glutamic acid residue in the TmR3 protein, which renders the TmR3 catalytically inactive, does not alter its binding affinity (e.g., indicated by $K_M$) to dsRNA (e.g., Nicholson et al., Wiley Interdiscip Rev RNA. 2014 January; 5(1): 31-48).

The coding sequence for TmR3 was cloned into a bacterial expression vector under the control of an IPTG inducible promoter. Expression of TmR3 was induced by isopropyl β-D-1-thiogalactopyranoside (IPTG) at 37° C., resulting in soluble TmR3 expression. TmR3 protein was purified by Ni-NTA affinity purification, and TmR3 having a purity of greater than 99% was obtained. A total of 30 mg of TmR3 was purified from 4 liters of bacterial culture. The purified TmR3 was stored as a solution having a concentration of 2 mg/ml. The purified TmR3 (MW=28.5 kDA) was resolved in the polyacrylamide gel shown in FIG. 1.

The protein sequence of the recombinant TmR3 is identified by SEQ ID NO: 7.

TMR3 protein sequence with 8xHis tag
{SEQ ID NO: 7}
MHHHHHHHHNESERKIVEEFQKETGINFKNEELLFRALCHSSYANEQNQA

GRKDVESNEKLEFLGDAVLELFVCEILYKKYPEAEVGDLARVKSAAASEE

VLAMVSRKMNLGKFLFLGKGEEKTGGRDRDSILADAFEALLAAIYLDQGY

EKIKELFEQEFEFYIEKIMKGEMLFDYKTALQEIVQSEHKVPPEYILVRT

EKNDGDRIFVVEVRVNGKTIATGKGRTKKEAEKEAARIAYEKLLKERS
(underlined sequence: 8xHis tag; bolded amino acid: glutamic acid residue critical for catalytic activity)

Example 2

*Thermotoga maritima* RNase III (TmR3) Temperature Study

To assess whether use of immobilized TmR3 in an affinity purification method results in non-specific degradation of RNA (e.g., mRNA) to be purified, synthetic mRNA was incubated with the purified TmR3 described in Example 1 at different temperatures (37° C., 45° C., or 65° C.) and non-specific degradation of the mRNA was analyzed on a size-exclusion column. mRNA having different 5'cap structures were also tested.

A human erythropoietin (hEPO) mRNA containing a natural 5' cap (G0) (FIGS. 2A-2D) or a 5' cap analog 7mG(5')ppp(5')NlmpNp (G5) (FIGS. 3A-3D) was incubated in reaction mixtures containing purified TmR3 at room temperature, 37° C., 45° C., or 65° C., and non-specific degradation products were observed at all temperatures, with most degraded fragments of the mRNA observed at 65° C.

A luciferase (Luc) mRNA containing a natural 5' cap (G0) (FIGS. 4A-4D) or a 5' cap analog 7mG(5')ppp(5')NlmpNp (G5) (FIGS. 5A-5D) was incubated in reaction mixtures containing purified TmR3 at room temperature, 37° C., 45° C., or 65° C., and the mixtures were analyzed on a size exclusion column. Non-specific degradation products were observed at almost all temperatures, with most degraded fragments of the mRNA observed at 65° C.

Example 3

Catalytically-Inactive 7TmR3

Results herein show that catalytically-inactive TmR3 reduces the non-specific RNA degradation observed in Example 2 (FIGS. 2A-5D). A E117K mutation abolished the catalytic activity of *E. coli* RNase III. The cognate mutation in TmR3 is E130K (FIG. 6). The TmR3-E130K mutant was expressed and purified. The expression and purification conditions and the yield are shown in Table 2.

TABLE 2

| Expression and Purification of TmR3-E130K Summary Information | |
|---|---|
| Expression Scale | 2 × 1 L |
| Enrichment | IMAC |
| Protein Conc. (mg/ml) | 1.09 mg/mL |
| Total Volume (ml) | 63 mL |
| Total Protein | 68.7 mg |
| Aliquot Size | 63 × 1 mL |
| Buffer Formulation | 30 mM Tris pH 8, 500 mM NaCl, 0.5 mM TCEP, 0.5 mM EOTA, 50% glycerol |
| Storage Temperate (° C.) | −20 C. |

To detect whether the purified TmR3 contains any non-specific RNase contamination, 20 µg of hEPO mRNA with a G5 cap was incubated with different amounts of TmR3 or TmR3-E130K in the buffer specified in Table 1. A reaction containing no added RNase was also used as a negative control. The reaction mixtures were incubated at room temperature for 1 hour, before the mixtures were subjected to the size exclusion analysis as described in Example 2. No detectable non-specific RNA contamination was observed (FIG. 7).

Further, a RNaseAlert test kit (ThermoFisher) was used to detect any non-specific RNase contamination in the purified TmR3. 5 µg of enzyme (TmR3, TmR3-E130K, Viv PAP, or RNase A) were incubated at 37° C. for 1 hour with a test buffer containing a RNA substrate tagged with a fluorescent reporter molecule (fluor) on one end and a quencher on the other. Degradation of the RNA substrate separates the quencher and the fluor, producing green fluorescence when excited by light of appropriate wavelength. Green fluorescence was not observed for TmR3 or TmR3-E130K, indicating the absence of a contaminating non-specific RNase.

Example 4

TmR3-E130K Mutant for RNA Purification (Prophetic)

The TmR3-E130K mutant protein is suitable for use in RNA purification. For example, in an in vitro transcription reaction where a mRNA is being produced, there often are short, double stranded RNA contaminants. Removing the dsRNA contaminants would yield pure mRNA. To be used for RNA purification, the TmR3 protein (e.g., TmR3-E130K) may be purified in large quantity and immobilized on a carboxy-reactive resin or amino reactive resin. Carboxy-reactive resins and amino reactive resins are familiar to the skilled artisan and are commercially available. The coupling procedure are also familiar to the skilled artisan. Different protein loading levels may be tested.

To use the resin for RNA purification, the resin may be packed into a column and equilibrated in appropriate buffer before the RNA sample (e.g., an in vitro transcription reaction mixture) is loaded to the resin. The dsRNA contaminants will be bound by the TmR3-E130K protein, while single-stranded mRNA is flowed through and collected. The quality (e.g., purity and integrity) of the mRNA collected is then analyzed by gel electrophoresis, size exclusion column, or in functional assays.

Example 5

Immobilizing WT TmR3 and TmR3-E130K Proteins

The instant study was designed to immobilize the TmR3 (wild type and E130K variant) to different types of resins. Resins tested are N-hydroxysuccinimide (NHS) activated resins (e.g., from ThermoFisher Scientific) and CarboxyLink™ resins (e.g., from ThermoFisher Scientific).

For resin coupling, protein samples were dialyzed against 0.1 M sodium phosphate buffer with 150 mM NaCl and 0.1 M MES with 0.9% NaCl for NHS activated and CarboxyLink™ slurry, respectively. Binding of protein was performed by mixing top to bottom for 3 hours at room temperature. Unbound proteins were extracted by flow through, and resin were stored in sodium phosphate buffer with 0.05% azide. For coupling to CarboxyLink™ resin, 1-ethyl-3-(3-dimethylaminopropyl)carbodiimide hydrochloride (EDC) was added as a crosslinker to conjugate protein to the resin.

For NHS resin, 1.86, 3.71 and 7.43 ml of WT TmR3 or 2.21, 4.43 and 8.86 ml of E130K TmR3 after dialysis were added to achieve 0.5×, 1.0× and 2.0× protein binding to 1 ml slurry. SDA-PAGE analysis and Bradford assays show that the both WT TmR3 and E130K TmR3 were efficiently coupled to NHS resin and the higher level of efficiency was achieved at 0.5× (FIGS. 8A-8B, and Tables 3-4).

Figure 9A:
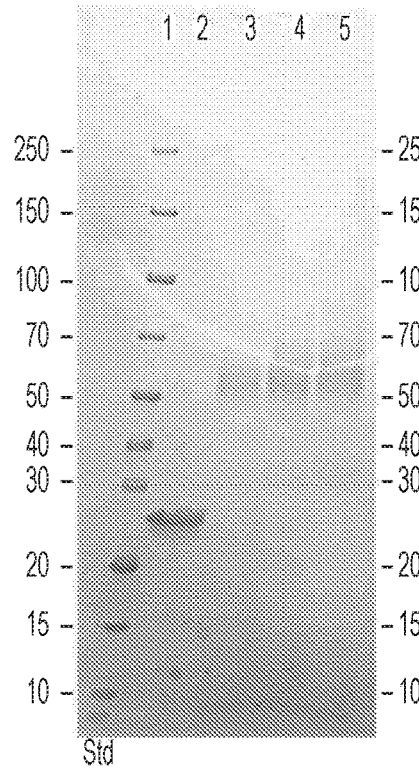
FIGS. 9A-9B are gels showing the results of coupling wild type TmR3 (FIG. 9A) and E130K TmR3 variant (FIG. 9B) to CarboxyLink™ Coupling Resin. The coupling efficiency was analyzed using SDS-PAGE and Bradford assays. The coupling efficiency for the CarboxyLink™ resin was less than that of the NHS resin.
Figure 9B:
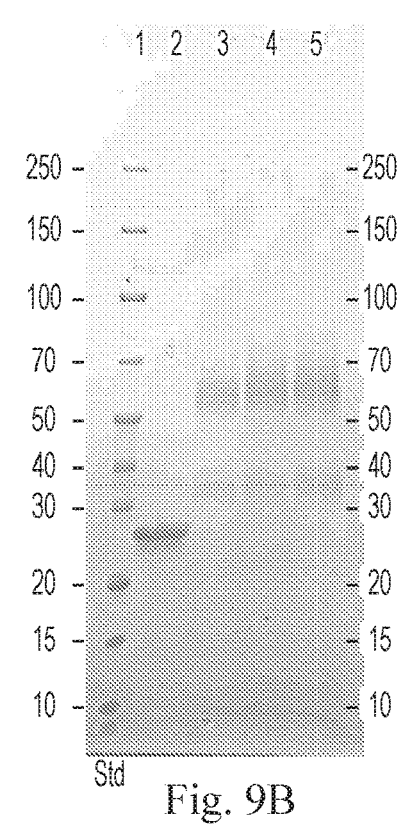

For CarboxyLink™ resin 1.71, 3.43 and 6.85 ml of WT TmR3 or 2, 4 and 8 ml of E310K TmR3 were added to achieve 0.5×, 1.0× and 2.0× protein binding to 1 ml slurry. SDA-PAGE analysis and Bradford assays showed that the crosslinking efficiency was less than that for the NHS resin at all concentrations for both WT TmR3 and E130K TmR3 (FIGS. 9A-9B, and Tables 5-6). Without being bound by theory, it is possible that the TmR3 proteins were crosslinked in solution and only a small percentage of the protein pool was able to successfully couple to the resin.

TABLE 3

Figure 8A:
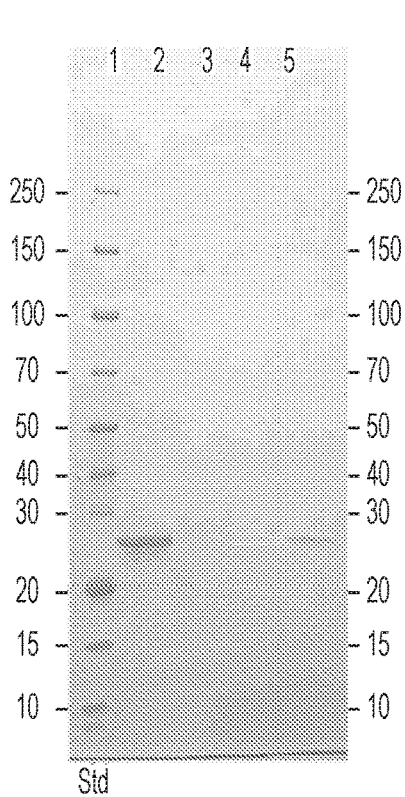
FIGS. 8A-8B are gels showing the results of coupling wild type TmRNase III (TmR3) (FIG. 8A) and E130K TmR3 variant (FIG. 8B) to N-hydroxysuccinimide (NHS) resin. The coupling efficiency was analyzed using SDS-PAGE and Bradford assays, TmR3 proteins were efficiently coupled to the NHS resin.
Figure 8B:
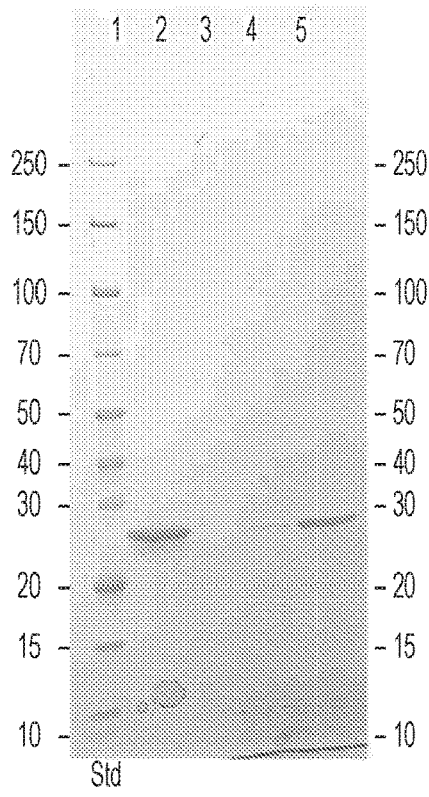

| Coupling WT TmR3 to NHS Resin | | | | |
|---|---|---|---|---|
| Lanes of FIG. 8A | Protein | Resin | Volume Loaded (µl) | Binding Efficiency (Bradford Assay) |
| 1 | Fermentas Marker | no resin | 4 | NA |
| 2 | WT TmR3 | no resin | 15 | NA |
| 3 | WT TmR3 0.5 X | NHS | 15 | ~97% |
| 4 | WT TmR3 1.0 X | NHS | 15 | ~92% |
| 5 | WT TmR3 2.0 X | NHS | 15 | ~76% |

TABLE 4

Coupling E130K TmR3 to NHS Resin

| Lanes of FIG. 8B | Protein | Resin | Volume Loaded (μl) | Binding Efficiency (Bradford Assay) |
|---|---|---|---|---|
| 1 | Fermentas Marker | no resin | 4 | NA |
| 2 | E130K TmR3 | no resin | 15 | NA |
| 3 | E130K TmR3 0.5 X | NHS | 15 | ~98% |
| 4 | E130K TmR3 1.0 X | NHS | 15 | ~89% |
| 5 | E130K TmR3 2.0 X | NHS | 15 | ~58% |

TABLE 5

Coupling WT TmR3 to CarboxyLink™ Resin

| Lanes of FIG. 9A | Protein | Resin | Volume Loaded (μl) | Binding Efficiency (Bradford Assay) |
|---|---|---|---|---|
| 1 | Fermentas Marker | no resin | 4 | NA |
| 2 | WT TmR3 | no resin | 15 | NA |
| 3 | WT TmR3 0.5 X | CarboxyLink™ | 15 | ~3% |
| 4 | WT TmR3 1.0 X | CarboxyLink™ | 15 | NA |
| 5 | WT TmR3 2.0 X | CarboxyLink™ | 15 | NA |

TABLE 6

Coupling E130K TmR3 to CarboxyLink™ Resin

| Lanes of FIG. 9B | Protein | Resin | Volume Loaded (μl) | Binding Efficiency (Bradford Assay) |
|---|---|---|---|---|
| 1 | Fermentas Marker | no resin | 4 | NA |
| 2 | E130K TmR3 | no resin | 15 | NA |
| 3 | E130K TmR3 0.5 X | CarboxyLink™ | 15 | ~6% |
| 4 | E130K TmR3 1.0 X | CarboxyLink™ | 15 | ~12% |
| 5 | E130K TmR3 2.0 X | CarboxyLink™ | 15 | NA |

Example 6

Purification of mRNA Encoding Human Erythropoietin (Epo) from IVT

The instant study was designed to demonstrate that the RNA purification methods described herein may be used to remove double-stranded RNA contaminants from single-stranded RNA preparations (e.g., mRNA produced via in vitro transcription).

Figure 10A:
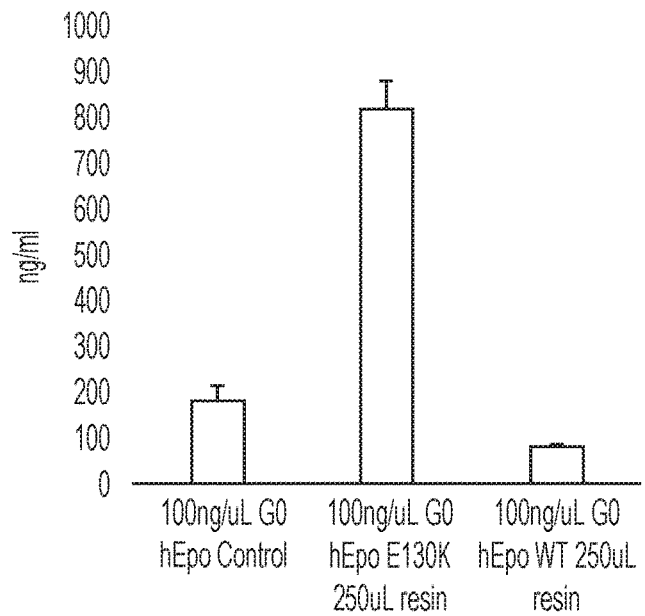
FIGS. 10A-10B are graphs showing the results of an ELISA for human erythropoietin (EPO) expression (FIG. 10A) and INF-beta cytokine expression (FIG. 10B) in BJ fibroblasts 48 hours after transfected with mRNA coding for the human erythropoietin (hEpo) protein and purified using an affinity purification method of the present disclosure.
Figure 10B:
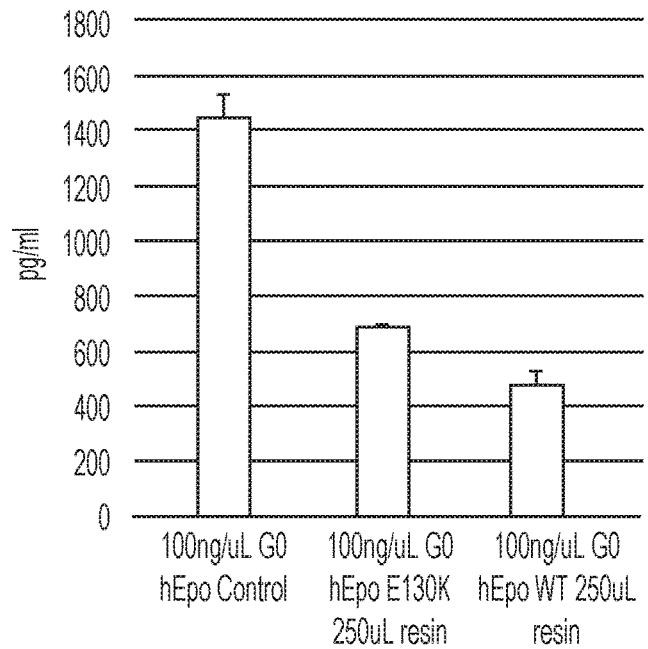

MRNA coding for the human erythropoietin (Epo) protein was made using standard in vitro transcription conditions and purified using polyT affinity chromatography. 100 μg of mRNA was mixed with reaction buffer containing 33 mM Tris-acetate, pH 7.5, 66 mM potassium acetate, 10 mM magnesium acetate, and 0.5 mM TCEP, to a final volume of 250 μl and added to 250 μl of "2.0×" N-hydroxysuccinimide (NHS) resin containing either WT or E130K mutant immobilized RNase III enzyme. The slurry was incubated at room temperature for 30 minutes and then passed through a spin filter to remove the resin. The clarified solution containing mRNA was transfected into BJ fibroblasts using L2000 according to the manufacturer protocol. Forty-eight hours after transfection, the supernatant from the transfection was collected and analyzed by ELISA for human EPO expression (FIG. 10A) and INF-beta cytokine expression (FIG. 10B) and according to their manufacturer protocols.

EQUIVALENTS AND SCOPE

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of purifying a nucleic acid preparation, comprising:
   contacting a nucleic acid preparation comprising messenger ribonucleic acid (mRNA) and double stranded RNA (dsRNA) with an RNase III enzyme that (i) is immobilized on a solid support, (ii) is catalytically inactive, and (iii) can specifically bind to the dsRNA; and
   eluting a purified nucleic acid preparation comprising the mRNA from the solid support.

2. The method of claim 1, wherein the mRNA is an in vitro-transcribed mRNA.

3. The method of claim 1, wherein the RNase III enzyme is a thermostable RNase III enzyme.

4. The method of claim 3, wherein the thermostable RNase III enzyme is a *Thermotoga maritima* RNase III enzyme.

5. The method of claim 1, wherein the RNase III enzyme comprises an amino acid sequence having a modification at an amino acid position corresponding to E130 of the amino acid sequence of SEQ ID NO: 3.

6. The method of claim 5, wherein the RNase III enzyme comprises the amino acid sequence of SEQ ID NO: 4.

7. The method of claim 1, wherein the solid support comprises a carboxy-reactive resin or an amino-reactive resin.

8. The method of claim 1, wherein the catalytically inactive RNase III enzyme has at least one amino acid mutation relative to a corresponding wild-type RNase III enzyme.

9. The method of claim 1, wherein the purification is performed at a temperature of from 40° C. to 70° C.

10. The method of claim 1, wherein the RNase III enzyme comprises the amino acid sequence of SEQ ID NO: 2 or SEQ ID NO: 6.

11. An affinity purification method comprising:
   passing a nucleic acid preparation over an affinity purification column to which an RNase III enzyme is immobilized, wherein the nucleic acid preparation comprises messenger ribonucleic acid (mRNA) and double stranded RNA (dsRNA), and wherein the RNase III enzyme is catalytically inactive and can specifically bind to the dsRNA; and
   eluting a purified nucleic acid preparation comprising the mRNA from the solid support.

12. The method of claim 11, wherein the RNase III enzyme is a thermostable RNase III enzyme.

13. The method of claim 12, wherein the thermostable RNase III enzyme is a *Thermotoga maritima* RNase III enzyme.

14. The method of claim 13, wherein the RNase III enzyme comprises an amino acid sequence having a modification at an amino acid position corresponding to E130 of the amino acid sequence of SEQ ID NO: 3.

15. The method of claim 11, wherein the RNase III enzyme comprises the amino acid sequence of SEQ ID NO: 2, SEQ ID NO: 4, or SEQ ID NO: 6.

16. The method of claim 11, wherein the solid support comprises a carboxy-reactive resin or an amino-reactive resin.

17. The method of claim 11, wherein the catalytically inactive RNase III enzyme has at least one amino acid mutation relative to a corresponding wild-type RNase III enzyme.

18. The method of claim 11, wherein the purification is performed at a temperature of from 40° C. to 70° C.

* * * * *

SEQUENCE LISTING

<160> NUMBER OF SEQ ID NOS: 7

<210> SEQ ID NO 1
<211> LENGTH: 226
<212> TYPE: PRT
<213> ORGANISM: Escherichia coli

<400> SEQUENCE: 1

```
Met Asn Pro Ile Val Ile Asn Arg Leu Gln Arg Lys Leu Gly Tyr Thr
1               5                   10                  15

Phe Asn His Gln Glu Leu Leu Gln Gln Ala Leu Thr His Arg Ser Ala
            20                  25                  30

Ser Ser Lys His Asn Glu Arg Leu Glu Phe Leu Gly Asp Ser Ile Leu
        35                  40                  45
```

-continued

```
Ser Tyr Val Ile Ala Asn Ala Leu Tyr His Arg Phe Pro Arg Val Asp
 50                  55                  60

Glu Gly Asp Met Ser Arg Met Arg Ala Thr Leu Val Arg Gly Asn Thr
 65                  70                  75                  80

Leu Ala Glu Leu Ala Arg Glu Phe Glu Leu Gly Glu Cys Leu Arg Leu
                 85                  90                  95

Gly Pro Gly Glu Leu Lys Ser Gly Gly Phe Arg Arg Glu Ser Ile Leu
                100                 105                 110

Ala Asp Thr Val Glu Ala Leu Ile Gly Gly Val Phe Leu Asp Ser Asp
                115                 120                 125

Ile Gln Thr Val Glu Lys Leu Ile Leu Asn Trp Tyr Gln Thr Arg Leu
            130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Thr Tyr Leu Val
                165                 170                 175

Val Gln Val Arg Gly Glu Ala His Asp Gln Glu Phe Thr Ile His Cys
            180                 185                 190

Gln Val Ser Gly Leu Ser Glu Pro Val Val Gly Thr Gly Ser Ser Arg
        195                 200                 205

Arg Lys Ala Glu Gln Ala Ala Glu Gln Ala Leu Lys Lys Leu Glu
    210                 215                 220

Leu Glu
225

<210> SEQ ID NO 2
<211> LENGTH: 226
<212> TYPE: PRT
<213> ORGANISM: Escherichia coli

<400> SEQUENCE: 2

Met Asn Pro Ile Val Ile Asn Arg Leu Gln Arg Lys Leu Gly Tyr Thr
 1               5                  10                  15

Phe Asn His Gln Glu Leu Leu Gln Gln Ala Leu Thr His Arg Ser Ala
                 20                  25                  30

Ser Ser Lys His Asn Glu Arg Leu Glu Phe Leu Gly Asp Ser Ile Leu
             35                  40                  45

Ser Tyr Val Ile Ala Asn Ala Leu Tyr His Arg Phe Pro Arg Val Asp
 50                  55                  60

Glu Gly Asp Met Ser Arg Met Arg Ala Thr Leu Val Arg Gly Asn Thr
 65                  70                  75                  80

Leu Ala Glu Leu Ala Arg Glu Phe Glu Leu Gly Glu Cys Leu Arg Leu
                 85                  90                  95

Gly Pro Gly Glu Leu Lys Ser Gly Gly Phe Arg Arg Glu Ser Ile Leu
                100                 105                 110

Ala Asp Thr Val Lys Ala Leu Ile Gly Gly Val Phe Leu Asp Ser Asp
                115                 120                 125

Ile Gln Thr Val Glu Lys Leu Ile Leu Asn Trp Tyr Gln Thr Arg Leu
            130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Thr Tyr Leu Val
                165                 170                 175

Val Gln Val Arg Gly Glu Ala His Asp Gln Glu Phe Thr Ile His Cys
```

```
                    180                 185                 190
Gln Val Ser Gly Leu Ser Glu Pro Val Val Gly Thr Gly Ser Ser Arg
                195                 200                 205

Arg Lys Ala Glu Gln Ala Ala Glu Gln Ala Leu Lys Lys Leu Glu
    210                 215                 220

Leu Glu
225

<210> SEQ ID NO 3
<211> LENGTH: 240
<212> TYPE: PRT
<213> ORGANISM: Thermotoga maritima

<400> SEQUENCE: 3

Met Asn Glu Ser Glu Arg Lys Ile Val Glu Glu Phe Gln Lys Glu Thr
1               5                   10                  15

Gly Ile Asn Phe Lys Asn Glu Glu Leu Leu Phe Arg Ala Leu Cys His
                20                  25                  30

Ser Ser Tyr Ala Asn Glu Gln Asn Gln Ala Gly Arg Lys Asp Val Glu
            35                  40                  45

Ser Asn Glu Lys Leu Glu Phe Leu Gly Asp Ala Val Leu Glu Leu Phe
        50                  55                  60

Val Cys Glu Ile Leu Tyr Lys Lys Tyr Pro Glu Ala Glu Val Gly Asp
65                  70                  75                  80

Leu Ala Arg Val Lys Ser Ala Ala Ser Glu Glu Val Leu Ala Met
                85                  90                  95

Val Ser Arg Lys Met Asn Leu Gly Lys Phe Leu Phe Leu Gly Lys Gly
                100                 105                 110

Glu Glu Lys Thr Gly Gly Arg Asp Arg Asp Ser Ile Leu Ala Asp Ala
            115                 120                 125

Phe Glu Ala Leu Leu Ala Ala Ile Tyr Leu Asp Gln Gly Tyr Glu Lys
130                 135                 140

Ile Lys Glu Leu Phe Glu Gln Glu Phe Glu Phe Tyr Ile Glu Lys Ile
145                 150                 155                 160

Met Lys Gly Glu Met Leu Phe Asp Tyr Lys Thr Ala Leu Gln Glu Ile
                165                 170                 175

Val Gln Ser Glu His Lys Val Pro Pro Glu Tyr Ile Leu Val Arg Thr
            180                 185                 190

Glu Lys Asn Asp Gly Asp Arg Ile Phe Val Glu Val Arg Val Asn
        195                 200                 205

Gly Lys Thr Ile Ala Thr Gly Lys Gly Arg Thr Lys Lys Glu Ala Glu
        210                 215                 220

Lys Glu Ala Ala Arg Ile Ala Tyr Glu Lys Leu Leu Lys Glu Arg Ser
225                 230                 235                 240

<210> SEQ ID NO 4
<211> LENGTH: 240
<212> TYPE: PRT
<213> ORGANISM: Thermotoga maritima

<400> SEQUENCE: 4

Met Asn Glu Ser Glu Arg Lys Ile Val Glu Glu Phe Gln Lys Glu Thr
1               5                   10                  15

Gly Ile Asn Phe Lys Asn Glu Glu Leu Leu Phe Arg Ala Leu Cys His
                20                  25                  30

Ser Ser Tyr Ala Asn Glu Gln Asn Gln Ala Gly Arg Lys Asp Val Glu
```

```
               35                  40                  45
Ser Asn Glu Lys Leu Glu Phe Leu Gly Asp Ala Val Leu Glu Leu Phe
 50                  55                  60

Val Cys Glu Ile Leu Tyr Lys Lys Tyr Pro Glu Ala Glu Val Gly Asp
 65                  70                  75                  80

Leu Ala Arg Val Lys Ser Ala Ala Ser Glu Glu Val Leu Ala Met
                 85                  90                  95

Val Ser Arg Lys Met Asn Leu Gly Lys Phe Leu Phe Leu Gly Lys Gly
                100                 105                 110

Glu Glu Lys Thr Gly Gly Arg Asp Arg Asp Ser Ile Leu Ala Asp Ala
                115                 120                 125

Phe Lys Ala Leu Leu Ala Ala Ile Tyr Leu Asp Gln Gly Tyr Glu Lys
        130                 135                 140

Ile Lys Glu Leu Phe Glu Gln Glu Phe Glu Phe Tyr Ile Glu Lys Ile
145                 150                 155                 160

Met Lys Gly Glu Met Leu Phe Asp Tyr Lys Thr Ala Leu Gln Glu Ile
                165                 170                 175

Val Gln Ser Glu His Lys Val Pro Pro Glu Tyr Ile Leu Val Arg Thr
                180                 185                 190

Glu Lys Asn Asp Gly Asp Arg Ile Phe Val Val Glu Val Arg Val Asn
        195                 200                 205

Gly Lys Thr Ile Ala Thr Gly Lys Gly Arg Thr Lys Lys Glu Ala Glu
210                 215                 220

Lys Glu Ala Ala Arg Ile Ala Tyr Glu Lys Leu Leu Lys Glu Arg Ser
225                 230                 235                 240

<210> SEQ ID NO 5
<211> LENGTH: 221
<212> TYPE: PRT
<213> ORGANISM: Aquifex aeolicus

<400> SEQUENCE: 5

Met Lys Met Leu Glu Gln Leu Glu Lys Lys Leu Gly Tyr Thr Phe Lys
 1                   5                  10                  15

Asp Lys Ser Leu Leu Glu Lys Ala Leu Thr His Val Ser Tyr Ser Lys
                 20                  25                  30

Lys Glu His Tyr Glu Thr Leu Glu Phe Leu Gly Asp Ala Leu Val Asn
            35                  40                  45

Phe Phe Ile Val Asp Leu Leu Val Gln Tyr Ser Pro Asn Lys Arg Glu
 50                  55                  60

Gly Phe Leu Ser Pro Leu Lys Ala Tyr Leu Ile Ser Glu Glu Phe Phe
 65                  70                  75                  80

Asn Leu Leu Ala Gln Lys Leu Glu Leu His Lys Phe Ile Arg Ile Lys
                 85                  90                  95

Arg Gly Lys Ile Asn Glu Thr Ile Ile Gly Asp Val Phe Glu Ala Leu
                100                 105                 110

Trp Ala Ala Val Tyr Ile Asp Ser Gly Arg Asp Ala Asn Phe Thr Arg
        115                 120                 125

Glu Leu Phe Tyr Lys Leu Phe Lys Glu Asp Ile Leu Ser Ala Ile Lys
    130                 135                 140

Glu Gly Arg Val Lys Lys Asp Tyr Lys Thr Ile Leu Gln Glu Ile Thr
145                 150                 155                 160

Gln Lys Arg Trp Lys Glu Arg Pro Glu Tyr Arg Leu Ile Ser Val Glu
                165                 170                 175
```

```
Gly Pro His His Lys Lys Lys Phe Ile Val Glu Ala Lys Ile Lys Glu
            180                 185                 190

Tyr Arg Thr Leu Gly Glu Gly Lys Ser Lys Lys Glu Ala Glu Gln Arg
            195                 200                 205

Ala Ala Glu Glu Leu Ile Lys Leu Leu Glu Glu Ser Glu
210                 215                 220

<210> SEQ ID NO 6
<211> LENGTH: 221
<212> TYPE: PRT
<213> ORGANISM: Aquifex aeolicus

<400> SEQUENCE: 6

Met Lys Met Leu Glu Gln Leu Glu Lys Lys Leu Gly Tyr Thr Phe Lys
1               5                   10                  15

Asp Lys Ser Leu Leu Glu Lys Ala Leu Thr His Val Ser Tyr Ser Lys
            20                  25                  30

Lys Glu His Tyr Glu Thr Leu Glu Phe Leu Gly Asp Ala Leu Val Asn
        35                  40                  45

Phe Phe Ile Val Asp Leu Leu Val Gln Tyr Ser Pro Asn Lys Arg Glu
    50                  55                  60

Gly Phe Leu Ser Pro Leu Lys Ala Tyr Leu Ile Ser Glu Glu Phe Phe
65                  70                  75                  80

Asn Leu Leu Ala Gln Lys Leu Glu Leu His Lys Phe Ile Arg Ile Lys
                85                  90                  95

Arg Gly Lys Ile Asn Glu Thr Ile Ile Gly Asp Val Phe Lys Ala Leu
            100                 105                 110

Trp Ala Ala Val Tyr Ile Asp Ser Gly Arg Asp Ala Asn Phe Thr Arg
        115                 120                 125

Glu Leu Phe Tyr Lys Leu Phe Lys Glu Asp Ile Leu Ser Ala Ile Lys
    130                 135                 140

Glu Gly Arg Val Lys Lys Asp Tyr Lys Thr Ile Leu Gln Glu Ile Thr
145                 150                 155                 160

Gln Lys Arg Trp Lys Glu Arg Pro Glu Tyr Arg Leu Ile Ser Val Glu
                165                 170                 175

Gly Pro His His Lys Lys Lys Phe Ile Val Glu Ala Lys Ile Lys Glu
            180                 185                 190

Tyr Arg Thr Leu Gly Glu Gly Lys Ser Lys Lys Glu Ala Glu Gln Arg
            195                 200                 205

Ala Ala Glu Glu Leu Ile Lys Leu Leu Glu Glu Ser Glu
210                 215                 220

<210> SEQ ID NO 7
<211> LENGTH: 248
<212> TYPE: PRT
<213> ORGANISM: Artificial Sequence
<220> FEATURE:
<223> OTHER INFORMATION: Synthetic polypeptide

<400> SEQUENCE: 7

Met His His His His His His His Asn Glu Ser Glu Arg Lys Ile
1               5                   10                  15

Val Glu Glu Phe Gln Lys Glu Thr Gly Ile Asn Phe Lys Asn Glu Glu
            20                  25                  30

Leu Leu Phe Arg Ala Leu Cys His Ser Ser Tyr Ala Asn Glu Gln Asn
        35                  40                  45

Gln Ala Gly Arg Lys Asp Val Glu Ser Asn Glu Lys Leu Glu Phe Leu
```

-continued

```
         50                  55                  60
Gly Asp Ala Val Leu Glu Leu Phe Val Cys Glu Ile Leu Tyr Lys Lys
 65                  70                  75                  80

Tyr Pro Glu Ala Glu Val Gly Asp Leu Ala Arg Val Lys Ser Ala Ala
                 85                  90                  95

Ala Ser Glu Glu Val Leu Ala Met Val Ser Arg Lys Met Asn Leu Gly
                100                 105                 110

Lys Phe Leu Phe Leu Gly Lys Gly Glu Lys Thr Gly Gly Arg Asp
                115                 120                 125

Arg Asp Ser Ile Leu Ala Asp Ala Phe Glu Ala Leu Leu Ala Ala Ile
                130                 135                 140

Tyr Leu Asp Gln Gly Tyr Glu Lys Ile Lys Glu Leu Phe Glu Gln Glu
145                 150                 155                 160

Phe Glu Phe Tyr Ile Glu Lys Ile Met Lys Gly Glu Met Leu Phe Asp
                165                 170                 175

Tyr Lys Thr Ala Leu Gln Glu Ile Val Gln Ser Glu His Lys Val Pro
                180                 185                 190

Pro Glu Tyr Ile Leu Val Arg Thr Glu Lys Asn Asp Gly Asp Arg Ile
                195                 200                 205

Phe Val Val Glu Val Arg Val Asn Gly Lys Thr Ile Ala Thr Gly Lys
                210                 215                 220

Gly Arg Thr Lys Lys Glu Ala Glu Lys Glu Ala Ala Arg Ile Ala Tyr
225                 230                 235                 240

Glu Lys Leu Leu Lys Glu Arg Ser
                245
```